United States Patent
Donnell et al.

(10) Patent No.: US 9,422,331 B2
(45) Date of Patent: Aug. 23, 2016

(54) 2-OXO-2,3,4,5-TETRAHYDRO-1 H-BENZO[B]DIAZEPINES AND THEIR USE IN THE TREATMENT OF CANCER

(71) Applicant: Hoffmann-La Roche Inc., Nutley, NJ (US)

(72) Inventors: Andrew Forrest Donnell, West Windsor, NJ (US); Robert Kester, West Orange, NJ (US); Yan Lou, Pleasanton, CA (US); John Anthony, Bloomfield, NJ (US); Stacy Remiszewski, Washington, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/428,407

(22) PCT Filed: Sep. 16, 2013

(86) PCT No.: PCT/EP2013/069080
§ 371 (c)(1),
(2) Date: Mar. 16, 2015

(87) PCT Pub. No.: WO2014/044622
PCT Pub. Date: Mar. 27, 2014

(65) Prior Publication Data
US 2015/0225449 A1 Aug. 13, 2015

Related U.S. Application Data

(60) Provisional application No. 61/702,765, filed on Sep. 19, 2012.

(51) Int. Cl.
| | |
|---|---|
| *C07D 243/12* | (2006.01) |
| *C07K 5/062* | (2006.01) |
| *C07D 243/26* | (2006.01) |
| *A61K 38/05* | (2006.01) |
| *A61K 31/5513* | (2006.01) |

(52) U.S. Cl.
CPC .............. *C07K 5/06026* (2013.01); *A61K 38/05* (2013.01); *C07D 243/26* (2013.01); *A61K 31/5513* (2013.01)

(58) Field of Classification Search
CPC ..................................................... C07D 243/12
See application file for complete search history.

*Primary Examiner* — Bruck Kifle

(57) ABSTRACT

Disclosed are compounds of Formula I or pharmaceutically acceptable salts thereof, wherein W, Y, Z, R1, R2, R3, R4 and R5 are described herein, and methods of using said compounds in the treatment of cancer.

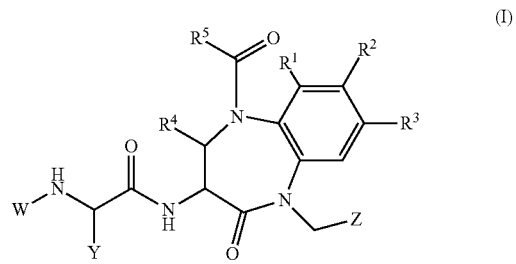

34 Claims, No Drawings

2-OXO-2,3,4,5-TETRAHYDRO-1 H-BENZO[B]DIAZEPINES AND THEIR USE IN THE TREATMENT OF CANCER

CROSS-REFERENCE TO RELATED APPLICATIONS

This application is a National Stage Application of PCT/EP2013/069080 filed Sep. 16, 2013, which claims priority from U.S. Provisional Patent Application No. 61/702,765, filed on Sep. 19, 2012. The priority of both said PCT and U.S. Provisional Patent Application are claimed. Each of the prior mentioned applications is hereby incorporated by reference herein in its entirety.

FIELD OF THE INVENTION

The present invention relates to branched diazepinones which act as inhibitors of SMAC protein binding to Inhibitor of Apoptosis Proteins (IAPs), and/or inhibitors of activated caspase protein binding to IAPs. These molecules are useful in the amelioration, treatment or control of cancer, especially solid tumors.

These compounds bind to the BIR2 and/or BIR3 regions of IAP proteins, including XIAP and cIAP, resulting in activation or reactivation of the caspase cascade and, as such, are useful for the treatment of proliferative diseases, including cancer.

BACKGROUND OF THE INVENTION

Cancer is a disease of uncontrolled cell growth causing local expansion of a tumor and, potentially, distant metastases. One mechanism by which cancer cells grow is by avoidance of apoptosis, or programmed cell death. Alterations in apoptotic pathways have been linked to cancer cells being resistant to standard treatments, e.g., chemotherapeutics or radiation, and to the incidence and progression of cancer. See, e.g., E. Dean et al., "X-linked inhibitor of apoptosis protein as a therapeutic target," Expert Opin. Ther. Targets (2007) 11(11):1459-1471

The two basic pathways for apoptotic cell death are the intrinsic pathway and the extrinsic pathway. The intrinsic apoptotic pathway can be initiated by various mechanisms including cellular stress and drug-induced DNA damage. The extrinsic pathway can be initiated by activation of the death receptors by a chemokine. Initiation of either pathway results in the activation of a family of proteases called caspases. Once activated, the caspases can act to cleave a variety of substrates creating a cascade of events that lead to the activation of the effector caspases 3 and 7 and eventual cell death. The IAP family of proteins can bind to and inhibit the activity of caspases thus inhibiting apoptosis. See, e.g., Dean, supra at 1460.

The IAPs can contain up to three copies of homologous structural domains called baculoviral IAP repeat (BIR) domains, BIR1, BIR2 and BIR3. The BIR3 domain of the prototypical IAPs, cIAP and XIAP, can bind to and inhibit activated caspase 9. The BIR2 domain, in contrast, binds to and inhibits caspases 3 and 7. The proapoptotic protein Smac (also known as DIABLO) can block the BIR2 and BIR3 domains of IAPs competing with activated caspases resulting in release of the activated caspases from the IAPs and completion of the apoptotic program. See, e.g., S. Wang, "Design of Small-Molecule Smac Mimetics as IAP Antagonists," Current Topics in Microbiology and Immunology 348, DOI 10.100782_2010_111, pp. 89-113.

Peptides and small molecules have been reported to bind to the BIR3 region of XIAP and cIAP, mimicking the action of Smac protein and releasing activated caspases. See, e.g., Dean, supra; and M. Gyrd-Hanse et al., "IAPs: From caspase inhibitors to modulators of NF-κB, inflammation and cancer," Nature Review/Cancer, August 2010, Vol 10:561-574.

SUMMARY OF THE INVENTION

One aspect of the present invention is a compound of Formula I

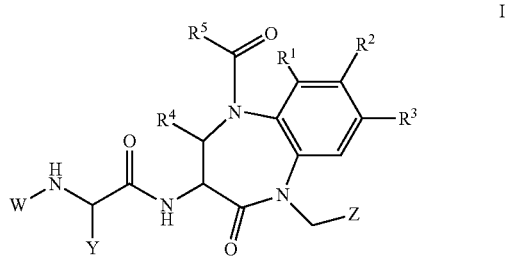

or pharmaceutically acceptable salts thereof, wherein W, Y, Z, R1, R2, R3, R4 and R5 are described in this application.

The present invention also relates to pharmaceutical compositions comprising one or more compounds of the invention, or a pharmaceutically acceptable salt thereof, and a pharmaceutically acceptable carrier or excipient.

The present invention further relates to a method of ameliorating, controlling or treating cancer, including specifically solid tumors, for example lung, pancreatic, colon, breast, bone and prostate cancers in a mammal, specifically a human, comprising administering to said mammal a therapeutically effective amount of a compound according to the invention or a pharmaceutically acceptable salt thereof.

DETAILED DESCRIPTION OF THE INVENTION

Definitions

Unless otherwise defined, all technical and scientific terms used herein have the same meaning as commonly understood by one of ordinary skill in the art to which this invention belongs.

As used herein, the following terms shall have the following definitions.

"Alkyl" means a monovalent linear or branched saturated hydrocarbon of 1 to 12 carbon atoms. In particular embodiments, alkyl has 1 to 6 carbon atoms, and in more particular embodiments 1 to 4 carbon atoms. As used herein, "lower alkyl" denotes an alkyl group having from 1-6 carbon atoms. Examples of alkyl include methyl, ethyl, propyl, isopropyl, butyl (also known as n-butyl), iso-butyl, sec-butyl, tert-butyl, pentyl, hexyl, and the like. The alkyl group can be optionally enriched in deuterium, e.g., —CD3, —CD2CD3 and the like.

"Aryl" means a monovalent aromatic carbocyclic mono-, bi- or tricyclic ring system comprising 6 to 19 carbon ring atoms. Examples of aryl moieties include, but are not limited to, phenyl, naphthyl (or naphathelenyl), tolyl, xylyl, pyridinyl, quinolinyl, pyrimidinyl, imidazolyl, thiazolyl, anthracenyl, tetrazolyl, and fluorenyl.

"Cyano" means —C≡N

"Cycloalkyl" means a substituted on unsubstituted stable monovalent saturated monocyclic, bicyclic or tricyclic system which consists of 3 to 10 ring carbon atoms. In particular embodiments cycloalkyl denotes a monovalent saturated monocyclic hydrocarbon group of 3 to 8 ring carbon atoms. Particular cycloalkyl groups are monocyclic. Examples for monocyclic cycloalkyl are cyclopropyl, cyclobutnyl, cyclopentyl, cyclohexyl or cycloheptyl. Bicyclic means consisting of two saturated carbocycles having one or more carbon atoms in common. Examples for bicyclic cycloalkyl are bicyclo[2.2.1]heptanyl, or bicyclo[2.2.2]octanyl. Tricyclic means consisting of three saturated carbocycles having two or more carbon atoms in common. Examples of tricyclic cycloalkyl include adamantane.

"Fused" when referring to two or more rings, e.g. aryl fused with cycloakyl, means that the rings have at least two atoms in common. An example of aryl fused with cycloalkyl is tetrahydronaphthalenyl. An example of aryl fused with heterocycle is benzopyranyl (or chromenyl).

"Halogen" or "Halo" means at atom selected from F, Cl, Br or I. In particular embodiments Halogen means F and Cl.

"Heteroatom" means at atom selected from N, O or S.

"Heteroaryl" means a substituted or unsubstituted aromatic heterocyclic ring system containing up to two rings, at least one ring of which includes 1, 2, or 3 heteroatoms, the remaining ring atoms being carbon. Examples of heteroaryl groups include, but are not limited to, thienyl (or thiophenyl), furyl (or furanyl), indolyl, pyrrolyl, pyridinyl, pyrazinyl, oxazolyl, isoxazolyl, oxadiazolyl, thiazolyl, quinolinyl, isoquinolinyl, indazolyl, pyrimidinyl, imidazolyl, triazolyl, tetrazolyl, triazinyl, pyrazolyl, benzo[d]isoxazolyl, 2-oxo-2H-chromen-4-yl, benzo[d]isoxazolyl, benzo[b]thiophenyl, naphthyrydinyl and cinnolinyl.

In the case of a heteroaryl that is bicyclic it should be understood that one ring may be aryl while the other is heteroaryl and both may be independently substituted or unsubstituted.

"Heterocyclyl," "heterocycle" or "heterocyclic ring" means a substituted or unsubstituted monovalent saturated or partly unsaturated mono- or bicyclic ring, non-aromatic hydrocarbon system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, tetrahydrofuranyl, piperazinyl, morpholinyl, thiomorpholinyl, 1,1-dioxo-thiomorpholin-4-yl, azepanyl, diazepanyl, homopiperazinyl, or oxazepanyl. Examples of partly unsaturated heterocycloalkyl are dihydrofuryl, imidazolinyl, dihydro-oxazolyl, dihydro-oxadiazolyl, dihydro-triazolyl, tetrahydro-pyridinyl, tetrahydro-triazinyl or dihydropyranyl.

In the case of a heterocycle that is bicyclic it should be understood that one ring may be heterocycle while the other is cycloalkyl, and either or both may be independently substituted. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl.

"IC50" refers to the concentration of a particular compound required to inhibit 50% of a specific measured activity. IC50 can be measured, inter alia, as is described subsequently in Example 55.

"Oxo" or ("Oxy") means =O.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoroacetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

"Substituted," as in substituted alkyl, aryl or heteroaryl means that the substitution (i.e. replacement of one hydrogen atom) can occur at one or more positions and, unless otherwise indicated, that the substituents at each substitution site are independently selected from the specified options. Also, when defining substitutions, "and" includes "or". Thus, "aryl substituted with methyl and Cl" means that the aryl can be substituted with methyl or Cl or methyl and Cl. The term "optionally substituted" refers to the fact that one or more hydrogen atoms of a chemical group (with one or more hydrogen atoms) can be, but does not necessarily have to be, substituted with another substituent.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

As used in this application, if a formula or group appears to be missing a substituent, that is it appears the valence is not complete, it is presumed the missing substituent is an H.

In the structural formulae presented herein a broken bond (a) denotes that the substituent is below the plane of the paper and a wedged bond (b) denotes that the substituent is above the plane of the paper.

In one embodiment, the present invention relates to compounds of Formula I

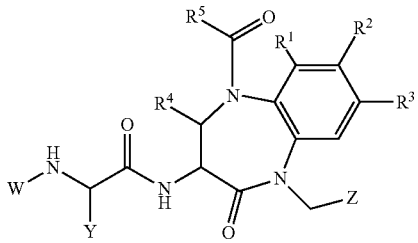

wherein
W is selected from H and lower alkyl that optionally may be substituted with 1-3 deuterium atoms;
Y is lower alkyl that optionally may be substituted with $OR^6$,
$R^1$, $R^2$ and $R^3$ are the same or different and each is independently selected from H and cyano;
$R^4$ is lower alkyl;
$R^5$ is selected from the group
  a) lower alkyl that optionally may be substituted with $SO_2R^6$ and $OR^6$,
  b) heterocyclyl, and
  c) aryl that optionally may be substituted with $C(O)R^7$, halo and cyano;
Z is selected from the group
  a) aryl that optionally may be substituted with lower alkyl, $OR^6$, halogen and aryl that optionally may be substituted with halogen,
  b) heteroaryl that optionally may be substituted with lower alkyl, cycloalkyl, $OR^6$, halogen, oxo and aryl that optionally may substituted with cyano, and
  c) aryl fused with heterocyclyl, wherein the aryl optionally may be substituted with $OR^6$ and halogen, and the heterocyclyl optionally may be substituted with oxo, and
  d) heterocyclyl;
$R^6$ is selected from H, and lower alkyl that optionally may be substituted with halogen and deuterium; and
$R^7$ is lower alkyl;
or a pharmaceutically acceptable salt thereof.

In one embodiment, the present invention relates to compounds of Formula I

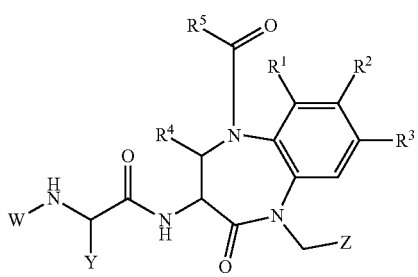

wherein
W is selected from H and $C_{1-6}$-alkyl that optionally may be substituted with 1-3 deuterium atoms;
Y is $C_{1-6}$-alkyl that optionally may be substituted with OR6,
R1, R2 and R3 are the same or different and each is independently selected from H and cyano;
R4 is $C_{1-6}$-alkyl;
R5 is selected from the group
  a) $C_{1-6}$-alkyl that optionally may be substituted with $SO_2R6$ and OR6,
  b) heterocyclyl, and
  c) aryl that optionally may be substituted with C(O)R7, halo and cyano;
Z is selected from the group
  a) aryl that optionally may be substituted with $C_{1-6}$-alkyl, OR6, halogen and aryl that optionally may be substituted with halogen,
  b) heteroaryl that optionally may be substituted with $C_{1-6}$-alkyl, $C_{3-76}$-cycloalkyl, OR6, halogen, oxo and aryl that optionally may substituted with cyano, and
  c) aryl fused with heterocyclyl, wherein the aryl optionally may be substituted with OR6 and halogen, and the heterocyclyl optionally may be substituted with oxo, and
  d) heterocyclyl;
R6 is selected from H, and $C_{1-6}$-alkyl that optionally may be substituted with halogen and deuterium; and
R7 is $C_{1-6}$-alkyl;
or a pharmaceutically acceptable salt thereof.

In one embodiment, the present invention relates to compounds of Formula I, wherein
W is methyl or ethyl;
Y is methyl or ethyl;
one of R1, R2 and R3 is cyano and the other two are H or all three of R1, R2 and R3 are H;
R4 is methyl;
R5 is selected from the group
  a) $CH_3$—C(O)-phenyl-,
  b) $CH_3$—O—$(CH_2)_2$—,
  c) $CH_3$—O—$CH_2$—,
  d) $CH_3$—$SO_2$—$CH_2$—,
  e) CN-phenyl-,
  f) methyl, and
  g) tetrahydro-2H-pyran-4-yl;
Z is selected from the group
  a) benzo[d]isoxazolyl, optionally substituted by Br;
  b) naphthyl, optionally substituted by one or two substituents selected from Br, methoxy, $CHF_2$—O— and methyl;
  c) phenyl, optionally substituted by one or two substituents selected from Br, Cl, methoxy, phenyl and fluoro-phenyl;
  d) quinolinyl, optionally substituted by one or two substituents selected from Cl, cyclopropyl, methoxy, methyl
  e) oxo-2H-chromenyl, optionally substituted by one or two substituents selected from Cl and methoxy;
  f) 1H-indazol-3-y, optionally substituted by one cyano-phenyl;
  g) 1H-indazolyl, optionally substituted by one methyl;
or a pharmaceutically acceptable salt thereof.

In one embodiment, the present invention relates to compounds of Formula I, wherein
W is methyl;
Y is methyl;
R1, R2 and R3 are H;
R4 is methyl;
R5 is selected from the group
  a) $CH_3$—C(O)-phenyl-,
  b) $CH_3$—O—$(CH_2)_2$—,
  c) $CH_3$—O—$CH_2$—,
  d) $CH_3$—$SO_2$—$CH_2$—,
  e) CN-phenyl-,
  f) methyl, and
  g) tetrahydro-2H-pyran-4-yl;

Z is selected from the group
a) benzo[d]isoxazolyl, optionally substituted by Br;
b) naphthyl, optionally substituted by one or two substituents selected from Br, methoxy, $CHF_2$—O— and methyl;
c) phenyl, optionally substituted by one or two substituents selected from Br, Cl, methoxy, phenyl and fluoro-phenyl;
d) quinolinyl, optionally substituted by one or two substituents selected from Cl, cyclopropyl, methoxy, methyl
e) oxo-2H-chromenyl, optionally substituted by one or two substituents selected from Cl and methoxy;
f) 1H-indazol-3-y, optionally substituted by one cyano-phenyl;
g) 1H-indazolyl, optionally substituted by one methyl;
or a pharmaceutically acceptable salt thereof.

In one embodiment, the present invention relates to compounds of Formula I, wherein
W is methyl;
Y is methyl;
R1, R2 and R3 are H;
R4 is methyl;
R5 is selected from the group
a) $CH_3$—C(O)-phenyl-,
b) $CH_3$—O—$(CH_2)_2$—,
c) $CH_3$—O—$CH_2$—,
d) $CH_3$—$SO_2$—$CH_2$—,
e) CN-phenyl-,
f) methyl, and
g) tetrahydro-2H-pyran-4-yl;
Z is naphthyl, optionally substituted by one or two substituents selected from Br, methoxy, $CHF_2$—O— and methyl;
or a pharmaceutically acceptable salt thereof.

One embodiment of the invention relates to compounds of Formula I where W is $C_{1-6}$-alkyl, or a pharmaceutically acceptable salt thereof. In a particular embodiment W is methyl.

Another embodiment of the invention relates to compounds of Formula I where Y is $C_{1-6}$-alkyl. In a particular embodiment Y is methyl or ethyl, or a pharmaceutically acceptable salt thereof.

Another embodiment of the invention relates to compounds of Formula I where R1, R2 and R3 are H, or a pharmaceutically acceptable salt thereof.

Another embodiment of the invention relates to compounds of Formula I where R1 is H and either R2 or R3 is cyano and the other is H, or a pharmaceutically acceptable salt thereof.

Another embodiment of the invention relates to compounds of Formula I where R4 is methyl, or a pharmaceutically acceptable salt thereof.

Another embodiment of the invention relates to compounds of Formula I where R5 is $C_{1-6}$-alkyl that optionally is substituted with $SO_2R6$ or OR6, or a pharmaceutically acceptable salt thereof. In a particular embodiment R6 is methyl in either of the immediately above described groups.

Another embodiment of the invention relates to compounds of Formula I where R5 is heterocyclyl, or a pharmaceutically acceptable salt thereof. In a particular embodiment R5 is tetrahydropyran.

Another embodiment of the invention relates to compounds of Formula I where R5 is aryl that optionally may be substituted with C(O)R7, halogen and cyano, or a pharmaceutically acceptable salt thereof. In a particular embodiment R5 is phenyl that optionally is substituted with $C(O)CH_3$ and cyano.

Another embodiment of the invention relates to compounds of Formula I where Z is aryl that may be substituted as described above, or a pharmaceutically acceptable salt thereof. In a particular embodiment Z is phenyl that optionally may be substituted with $OCH_3$, halogen and phenyl that itself may be substituted with halogen. In another embodiment, Z is naphthalenyl that optionally may be substituted with $OCH_3$, halogen, $CH_3$ and $OCHF_2$.

Another embodiment of the invention relates to compounds of Formula I where Z is heteroaryl that optionally may be substituted as defined above, or a pharmaceutically acceptable salt thereof. In a particular embodiment, Z is selected from quinolinyl, indazolyl, chromenyl and bensoisoxazolyl each of which optionally may be substituted as defined above.

Another embodiment of the invention relates to compounds of Formula I where Z is aryl fused with heterocyclyl, wherein the aryl and heterocyclyl may be substituted as defined above, or a pharmaceutically acceptable salt thereof. In a particular embodiment Z is chromenyl (or benzopyranyl).

Another embodiment of the invention relates to compounds of Formula I where R6 is methyl, or a pharmaceutically acceptable salt thereof.

Another embodiment of the invention relates to compounds of Formula I where R7 is methyl, or a pharmaceutically acceptable salt thereof.

Another embodiment of the invention relates to compounds of Formula I where W and Y are each methyl, R1 is H, R2 and R3 are each independently H or cyano, R4 is methyl, R5 is aryl, or a pharmaceutically acceptable salt thereof.

Another embodiment of the invention relates to compounds of Formula I where W and Y are each methyl, R1 is H, R2 and R3 are each independently H or cyano, R4 is methyl, R5 is $C_{1-6}$-alkyl that optionally may be substituted with $OCH_3$ or $SO_2CH_3$, or a pharmaceutically acceptable salt thereof.

Another embodiment of the invention relates to compounds of Formula I where W and Y are each methyl, R1 is H, R2 and R3 are each independently H or cyano, R4 is methyl, R5 is heterocyclyl.

Another embodiment of the invention relates to compounds of Formula I where W and Y are each methyl, R1 is H, R2 and R3 are each independently H or cyano, R4 is methyl, R5 is $C_{1-6}$-alkyl that optionally may be substituted with $SO_2CH_3$ or $OCH_3$, and Z is aryl, or a pharmaceutically acceptable salt thereof.

Another embodiment of the invention relates to compounds of Formula I where W and Y are each methyl, R1 is H, R2 and R3 are each independently H or cyano, R4 is methyl, R5 is $C_{1-6}$-alkyl that optionally may be substituted with $SO_2CH_3$ or $OCH_3$, and Z heteroaryl, or a pharmaceutically acceptable salt thereof.

Another embodiment of the invention relates to compounds of Formula I where W and Y are each methyl, R1 is H, R2 and R3 are each independently H or cyano, R4 is methyl, R5 is heterocyclyl and Z is aryl, or a pharmaceutically acceptable salt thereof.

Another embodiment of the invention relates to compounds of Formula I where W and Y are each methyl, R1 is H, R2 and R3 are each independently H or cyano, R4 is methyl, R5 is aryl and Z is aryl or heteroaryl, or a pharmaceutically acceptable salt thereof.

Another embodiment of the invention relates to compounds of Formula I where W and Y are each methyl, R1 is H, R2 and R3 are each independently H or cyano, R4 is methyl, R5 is C$_{1-6}$-alkyl that optionally may be substituted as defined above and Z is aryl fused with heterocyclyl, or a pharmaceutically acceptable salt thereof.

Compounds according to the invention wherein R5 is C$_{1-6}$-alkyl that optionally may be substituted as defined above include:

(S)-N-((3S,4S)-1-((6-bromo-2-methoxynaphthalen-1-yl) methyl)-4-methyl-5-(2-(methylsulfonyl)acetyl)-2-oxo-2, 3,4,5-tetrahydro-1H-benzo[b][1,4]diazepin-3-yl)-2-(methylamino)propanamide hydrochloride (Example 10);

(S)-N-((3S,4S)-1-((5-bromo-2-methoxynaphthalen-1-yl) methyl)-4-methyl-5-(2-(methylsulfonyl)acetyl)-2-oxo-2, 3,4,5-tetrahydro-1H-benzo[b][1,4]diazepin-3-yl)-2-(methylamino)propanamide hydrochloride (Example 11);

(S)-N-((3S,4S)-1-((7-methoxy-2-oxo-2H-chromen-4-yl) methyl)-4-methyl-5-(2-(methylsulfonyl)acetyl)-2-oxo-2, 3,4,5-tetrahydro-1H-benzo[b][1,4]diazepin-3-yl)-2-(methylamino)propanamide 2,2,2-trifluoroacetate (Example 12);

(S)-N-((3S,4S)-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride (Example 13);

(S)-N-((2S,3S)-2-methyl-5-((3-methylquinolin-4-yl)methyl)-1-(2-(methylsulfonyl)acetyl)-4-oxo-2,3,4,5-tetrahydro-1H-benzo[b][1,4]diazepin-3-yl)-2-(methylamino) propanamide hydrochloride (Example 14);

(S)-N-((3S,4S)-1-((2-chloro-3-methylquinolin-4-yl)methyl)-4-methyl-5-(2-(methylsulfonyl)acetyl)-2-oxo-2,3,4, 5-tetrahydro-1H-benzo[b][1,4]diazepin-3-yl)-2-(methylamino)propanamide hydrochloride (Example 15);

(S)-N-((2S,3S)-2-methyl-1-(2-(methylsulfonyl)acetyl)-4-oxo-5-(quinolin-4-ylmethyl)-2,3,4,5-tetrahydro-1H-benzo[b][1,4]diazepin-3-yl)-2-(methylamino)propanamide hydrochloride (Example 16);

(S)-N-((3S,4S)-1-((6-bromo-2-methoxynaphthalen-1-yl) methyl)-5-(3-methoxypropanoyl)-4-methyl-2-oxo-2,3,4, 5-tetrahydro-1H-benzo[b][1,4]diazepin-3-yl)-2-(methylamino)propanamide hydrochloride (Example 17);

(S)-N-((2S,3S)-1-acetyl-5-((3-cyclopropylquinolin-4-yl) methyl)-2-methyl-4-oxo-2,3,4,5-tetrahydro-1H-benzo[b] [1,4]diazepin-3-yl)-2-(methylamino)propanamide (Example 18);

(S)-N-((2S,3S)-1-acetyl-5-((1-(2-cyanophenyl)-1H-indazol-3-yl)methyl)-2-methyl-4-oxo-2,3,4,5-tetrahydro-1H-benzo[b][1,4]diazepin-3-yl)-2-(methylamino)propanamide (Example 19);

(S)-N-((2S,3S)-1-acetyl-2-methyl-5-((3-methylquinolin-4-yl)methyl)-4-oxo-2,3,4,5-tetrahydro-1H-benzo[b][1,4]diazepin-3-yl)-2-(methyl amino)propanamide dihydrochloride (Example 20);

(S)-N-((2S,3S)-1-acetyl-5-((2-methoxynaphthalen-1-yl)methyl)-2-methyl-4-oxo-2,3,4,5-tetrahydro-1H-benzo[b][1, 4]diazepin-3-yl)-2-(methylamino)propanamide hydrochloride (Example 21);

(S)-N-((2S,3S)-1-acetyl-2-methyl-5-((2-methylnaphthalen-1-yl)methyl)-4-oxo-2,3,4,5-tetrahydro-1H-benzo[b][1,4] diazepin-3-yl)-2-(methylamino)propanamide hydrochloride (Example 22);

(S)-N-((2S,3S)-5-((5-bromo-2-methoxynaphthalen-1-yl)methyl)-7-cyano-2-methyl-1-(2-(methylsulfonyl)acetyl)-4-oxo-2,3,4,5-tetrahydro-1H-benzo[b][1,4]diazepin-3-yl)-2-(methylamino)propanamide 2,2,2-trifluoroacetate (Example 25);

(S)-N-((3S,4S)-1-((5-bromo-2-methoxynaphthalen-1-yl) methyl)-7-cyano-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate (Example 26);

(S)-N-((3S,4S)-7-cyano-1-((2-methoxynaphthalen-1-yl)methyl)-4-methyl-5-(2-(methylsulfonyl)acetyl)-2-oxo-2,3,4, 5-tetrahydro-1H-benzo[b][1,4]diazepin-3-yl)-2-(methylamino)propanamide hydrochloride (Example 27);

(S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)propanamide hydrochloride (Example 28);

(S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)butanamide hydrochloride (Example 29);

(S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)butanamide hydrochloride (Example 30);

(S)-N-((3S,4S)-5-acetyl-7-cyano-1-((2-methoxynaphthalen-1-yl)methyl)-4-methyl-2-oxo-2,3,4,5-tetrahydro-1H-benzo[b][1,4]diazepin-3-yl)-2-(methylamino)propanamide hydrochloride (Example 31);

(S)-N-((3S,4S)-5-acetyl-7-cyano-4-methyl-1-((2-methylnaphthalen-1-yl)methyl)-2-oxo-2,3,4,5-tetrahydro-1H-benzo[b][1,4]diazepin-3-yl)-2-(methylamino)propanamide hydrochloride (Example 32);

(S)-N-((3S,4S)-5-acetyl-7-cyano-1-((3-cyclopropylquinolin-4-yl)methyl)-4-methyl-2-oxo-2,3,4,5-tetrahydro-1H-benzo[b][1,4]diazepin-3-yl)-2-(methylamino)propanamide dihydrochloride (Example 33);

(S)-N-((3S,4S)-5-acetyl-1-(5-bromo-2-methoxybenzyl)-7-cyano-4-methyl-2-oxo-2,3,4,5-tetrahydro-1H-benzo[b] [1,4]diazepin-3-yl)-2-(methylamino)propanamide hydrochloride (Example 36);

(S)-N-((3S,4S)-5-acetyl-7-cyano-1-((4-methoxybiphenyl-3-yl)methyl)-4-methyl-2-oxo-2,3,4,5-tetrahydro-1H-benzo [b][1,4]diazepin-3-yl)-2-(methylamino)propanamide hydrochloride (Example 37);

(S)-N-((3S,4S)-5-acetyl-7-cyano-1-((2'-fluoro-4-methoxybiphenyl-3-yl)methyl)-4-methyl-2-oxo-2,3,4,5-tetrahydro-1H-benzo[b][1,4]diazepin-3-yl)-2-(methylamino) propanamide hydrochloride (Example 38);

(S)-N-((3S,4S)-1-(benzo[d]isoxazol-3-ylmethyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate (Example 39);

(S)-N-((3S,4S)-1-((7-chloro-2-oxo-2H-chromen-4-yl)methyl)-4-methyl-5-(2-(methylsulfonyl)acetyl)-2-oxo-2,3,4, 5-tetrahydro-1H-benzo[b][1,4]diazepin-3-yl)-2-(methylamino)propanamide 2,2,2-trifluoroacetate (Example 40);

(S)-N-((3S,4S)-1-((6-bromobenzo[d]isoxazol-3-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate (Example 41);

(S)-N-((3S,4S)-1-((3-cyclopropylquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate (Example 42);

(S)-N-((3S,4S)-1-(5-chloro-2-methoxybenzyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate (Example 43);

(S)-N-((3S,4S)-1-((1-(2-cyanophenyl)-1H-indazol-3-yl)methyl)-4-methyl-5-(2-(methylsulfonyl)acetyl)-2-oxo-2,3,4, 5-tetrahydro-1H-benzo[b][1,4]diazepin-3-yl)-2-(methylamino)propanamide hydrochloride (Example 44);

(S)-N-((2S,3S)-2-methyl-5-((2-methylnaphthalen-1-yl)methyl)-1-(2-(methylsulfonyl)acetyl)-4-oxo-2,3,4,5-tetrahydro-1H-benzo[b][1,4]diazepin-3-yl)-2-(methylamino)propanamide hydrochloride (Example 45);

(S)-N-((2S,3S)-2-methyl-5-((1-methyl-1H-indazol-3-yl)methyl)-1-(2-(methylsulfonyl)acetyl)-4-oxo-2,3,4,5-tetrahydro-1H-benzo[b][1,4]diazepin-3-yl)-2-(methylamino)propanamide hydrochloride (Example 46);

(S)-N-((3S,4S)-1-((2-(difluoromethoxy)naphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride (Example 47);

(S)-N-((3S,4S)-1-((3-methoxyquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride (Example 48);

(S)-N-((3S,4S)-1-((5-bromo-2-methoxynaphthalen-1-yl)methyl)-5-(3-methoxypropanoyl)-4-methyl-2-oxo-2,3,4,5-tetrahydro-1H-benzo[b][1,4]diazepin-3-yl)-2-(methylamino)propanamide 2,2,2-trifluoroacetate (Example 49);

(S)-N-((3S,4S)-1-((2-methoxynaphthalen-1-yl)methyl)-5-(3-methoxypropanoyl)-4-methyl-2-oxo-2,3,4,5-tetrahydro-1H-benzo[b][1,4]diazepin-3-yl)-2-(methylamino)propanamide hydrochloride (Example 50);

(S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate (Example 51);

(S)-N-((3S,4S)-7-cyano-1-((3-cyclopropylquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate (Example 52); and (S)-N-((3S,4S)-7-cyano-1-((1-(2-cyanophenyl)-1H-indazol-3-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate (Example 53);

or a pharmaceutically acceptable salt of any of the foregoing compounds.

Compounds according to the invention wherein R5 is aryl that may be substituted as defined above include:

(S)-N-((2S,3S)-1-(4-acetylbenzoyl)-5-((5-bromo-2-methoxynaphthalen-1-yl)methyl)-2-methyl-4-oxo-2,3,4,5-tetrahydro-1H-benzo[b][1,4]diazepin-3-yl)-2-(methylamino)propanamide hydrochloride (Example 1);

(S)-N-((2S,3S)-1-(4-acetylbenzoyl)-5-((6-bromo-2-methoxynaphthalen-1-yl)methyl)-2-methyl-4-oxo-2,3,4,5-tetrahydro-1H-benzo[b][1,4]diazepin-3-yl)-2-(methylamino)propanamide hydrochloride (Example 2);

(S)-N-((2S,3S)-1-(4-acetylbenzoyl)-5-((1-(2-cyanophenyl)-1H-indazol-3-yl)methyl)-2-methyl-4-oxo-2,3,4,5-tetrahydro-1H-benzo[b][1,4]diazepin-3-yl)-2-(methylamino)propanamide hydrochloride (Example 3);

(S)-N-((2S,3S)-1-(4-acetylbenzoyl)-5-((3-cyclopropylquinolin-4-yl)methyl)-2-methyl-4-oxo-2,3,4,5-tetrahydro-1H-benzo[b][1,4]diazepin-3-yl)-2-(methylamino)propanamide dihydrochloride (Example 4);

(S)-N-((3S,4S)-1-((6-bromo-2-methoxynaphthalen-1-yl)methyl)-5-(4-cyanobenzoyl)-4-methyl-2-oxo-2,3,4,5-tetrahydro-1H-benzo[b][1,4]diazepin-3-yl)-2-(methylamino)propanamide hydrochloride (Example 5); and (S)-N-((3S,4S)-7-cyano-5-(4-cyanobenzoyl)-1-((1-(2-cyanophenyl)-1H-indazol-3-yl)methyl)-4-methyl-2-oxo-2,3,4,5-tetrahydro-1H-benzo[b][1,4]diazepin-3-yl)-2-(methylamino)propanamide hydrochloride (Example 6);

or a pharmaceutically acceptable salt of any of the foregoing compounds.

Compounds according to the invention wherein R5 is heterocyclyl include:

(S)-N-((3S,4S)-1-((6-bromo-2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (Example 7);

(S)-N-((3S,4S)-1-((5-bromo-2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (Example 8);

(S)-N-((3S,4S)-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (Example 9);

(S)-N-((3S,4S)-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (Example 23);

(S)-N-((3S,4S)-1-((1-(2-cyanophenyl)-1H-indazol-3-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (Example 24);

(S)-N-((3S,4S)-7-cyano-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (Example 34);

(S)-N-((3S,4S)-7-cyano-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide dihydrochloride (Example 35); and (S)-N-((3S,4S)-7-cyano-4-methyl-1-((2-methylnaphthalen-1-yl)methyl)-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (Example 54) or a pharmaceutically acceptable salt thereof.

Another embodiment of the invention relates to the following compounds:

(S)-N-((3S,4S)-1-((6-bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride (Example 10);

(S)-N-((3S,4S)-1-((5-bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride (Example 11);

(S)-N-((3S,4S)-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride (Example 13);

(S)-N-((3S,4S)-7-cyano-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride (Example 27);

(S)-N-((3S,4S)-5-acetyl-7-cyano-1-((2-methoxynaphthalen-1-yl)methyl)-4-methyl-2-oxo-2,3,4,5-tetrahydro-1H-benzo[b][1,4]diazepin-3-yl)-2-(methylamino)propanamide hydrochloride (Example 31);

(S)-N-((3S,4S)-5-acetyl-7-cyano-4-methyl-1-((2-methylnaphthalen-1-yl)methyl)-2-oxo-2,3,4,5-tetrahydro-1H- benzo[b][1,4]diazepin-3-yl)-2-(methylamino)propanamide hydrochloride (Example 32);

(S)-N-((3S,4S)-5-acetyl-7-cyano-1-((3-cyclopropylquinolin-4-yl)methyl)-4-methyl-2-oxo-2,3,4,5-tetrahydro-1H-benzo[b][1,4]diazepin-3-yl)-2-(methylamino)propanamide dihydrochloride (Example 33);

(S)-N-((3S,4S)-7-cyano-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (Example 34);

(S)-N-((3S,4S)-7-cyano-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide dihydrochloride (Example 35);

(S)-N-((3S,4S)-1-(benzo[d]isoxazol-3-ylmethyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate (Example 39);

(S)-N-((3S,4S)-1-((3-cyclopropylquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate (Example 42);

(S)-N-((3S,4S)-1-((1-(2-cyanophenyl)-1H-indazol-3-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride (Example 44);

(S)-N-((2S,3S)-2-methyl-5-((2-methylnaphthalen-1-yl)methyl)-1-(2-(methylsulfonyl)acetyl)-4-oxo-2,3,4,5-tetrahydro-1H-benzo[b][1,4]diazepin-3-yl)-2-(methylamino)propanamide hydrochloride (Example 45);

(S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate (Example 51); and (S)-N-((3S,4S)-7-cyano-4-methyl-1-((2-methylnaphthalen-1-yl)methyl)-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (Example 54); or a pharmaceutically acceptable salt of the foregoing compounds.

In one embodiment the invention relates to a pharmaceutical composition comprising any of the compounds as described herein, or a pharmaceutically acceptable salt thereof, as an active ingredient together with a pharmaceutically acceptable carrier or excipient.

In one embodiment the invention relates to compounds as described herein for use as a therapeutically active substance.

In one embodiment the invention relates to compounds as described herein for use for the therapeutic and/or prophylactic treatment of cancer.

In one embodiment the invention relates to the use of a compound as described herein, or a pharmaceutically acceptable salt thereof, for the manufacture of a medicament for the therapeutic and/or prophylactic treatment of cancer.

In one embodiment the invention relates to a method of treating or ameliorating cancer comprising administering to a subject in need of such treatment a therapeutically effective amount of a compound as described herein.

The compounds of Formula I as well as their salts have at least one asymmetric carbon atom and therefore may be present as mixtures of different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

Dosages

The compounds of the invention preferably bind to BIR domains of an IAP preventing the IAP from binding to other proteins. Examples of Bir binding proteins include, but are not limited to, caspase 3, caspase 7, caspase 9, Smac and the like. Examples of IAPs include, but are not limited to, XIAP, cIAP1, cIAP2 or NAIP. In one aspect, the compound of the invention bind to the BIR2 and/or BIR3 domains of XIAP, cIAP1 and/or cIAP2. In another aspect, the compounds of the invention bind to the BIR2 domain of XIAP, cIAP1 and/or cIAP2.

Compounds of the invention are useful for inducing apoptosis in cells or sensitizing cells to apoptotic signals, in particular cancer cells. Apoptotic signals can be induced in cancer cells by, e.g., radiation therapy or antineoplastic chemotherapy. Alternatively, apoptotic signals can be induced in cancer cells by activation of the death receptors by death receptor agonists. Death receptor agonists can be naturally occurring, e.g., tumor necrosis factor α, (TNF-α) or non-naturally occurring, e.g., a synthetic antibody such as a DR4 or DR5 antibody.

The compounds of the present invention are thus useful in the amelioration, control or treatment of cell proliferative disorders such as, in particular, oncological disorders. These compounds and formulations containing said compounds are anticipated to be useful in the treatment or control of blood cancers, such as, for example, acute myeloid leukemia, or solid tumors, such as, for example, breast, colon, lung and prostate tumors.

A "therapeutically effective amount" or "effective amount" of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

Compositions/Formulations

In an alternative embodiment, the present invention includes pharmaceutical compositions comprising at least one compound of formula I, or a pharmaceutically acceptable salt thereof, and a pharmaceutically acceptable excipient and/or carrier.

These pharmaceutical compositions can be suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

The compounds of Formula I and their pharmaceutically acceptable salts and esters can be processed with pharmaceutically inert, inorganic or organic adjuvants for the production of tablets, coated tablets, dragées and hard gelatin capsules. Lactose, polyvinylpyrrolidone, hydroxypropylmethylcellulose, hydroxypropyl-cellulose, microcrystalline cellulose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, H2O, polyols, saccharose, invert sugar, glucose, etc. Suitable adjuvants for injection solutions are, for example, H2O, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

The compounds in the present invention (compounds of general Formula I) can be prepared using the general reaction scheme set out in Scheme 1 below.

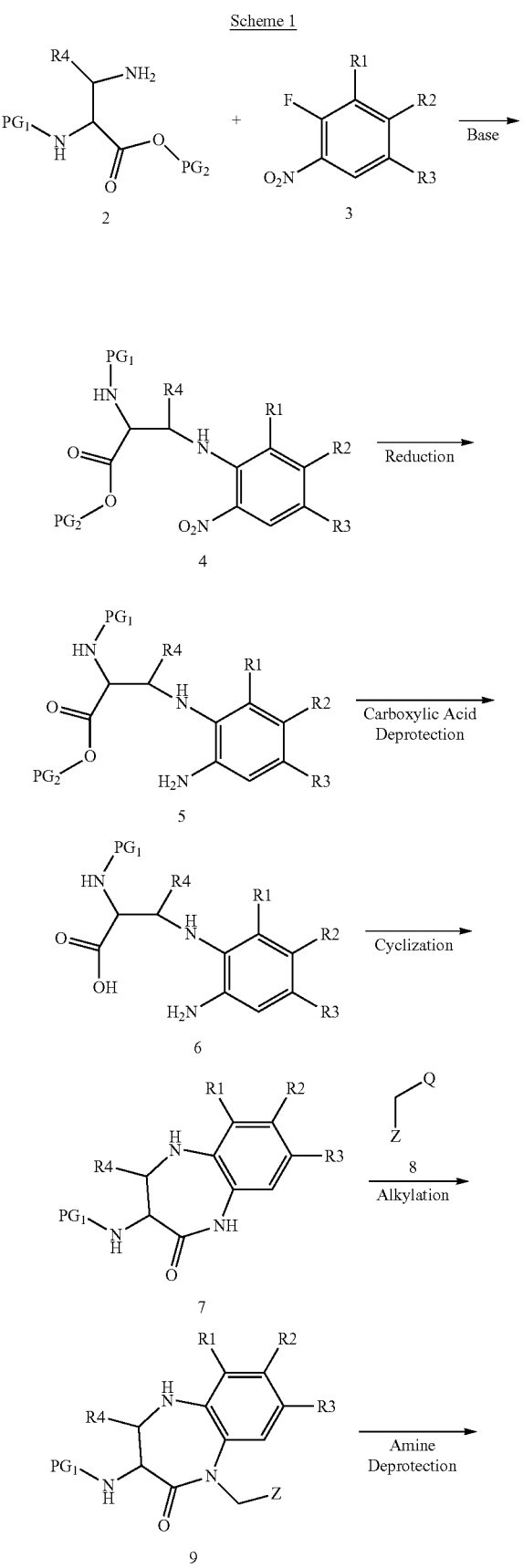

Scheme 2

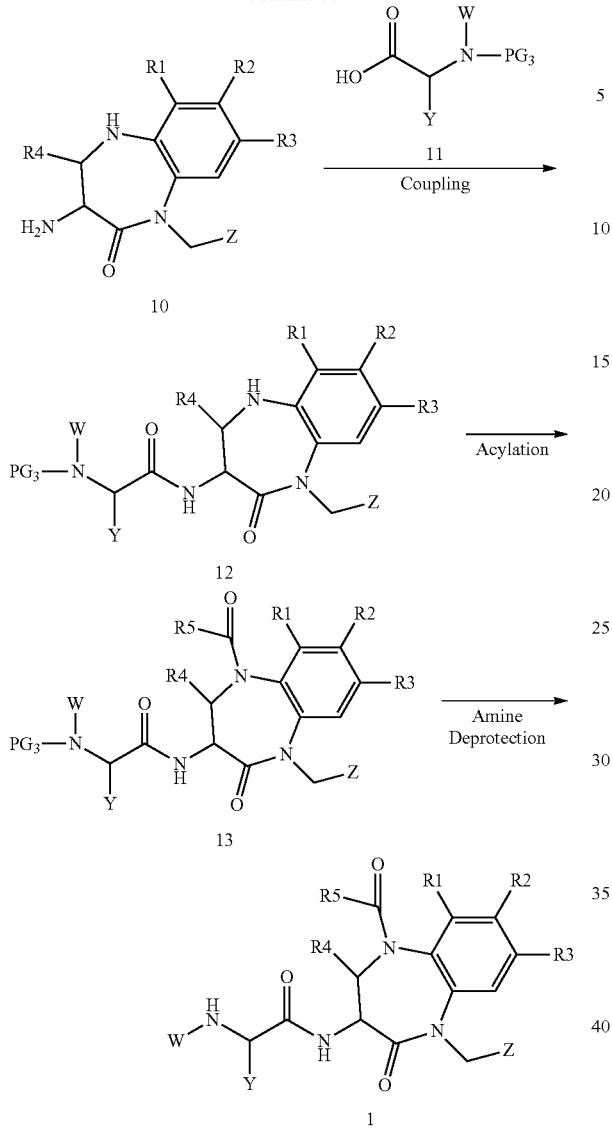

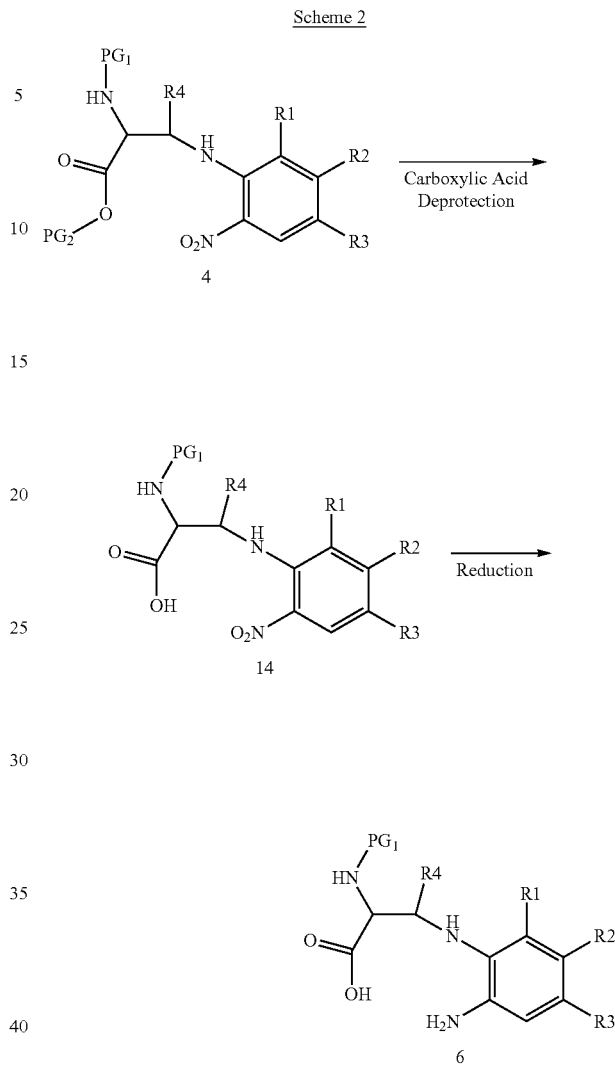

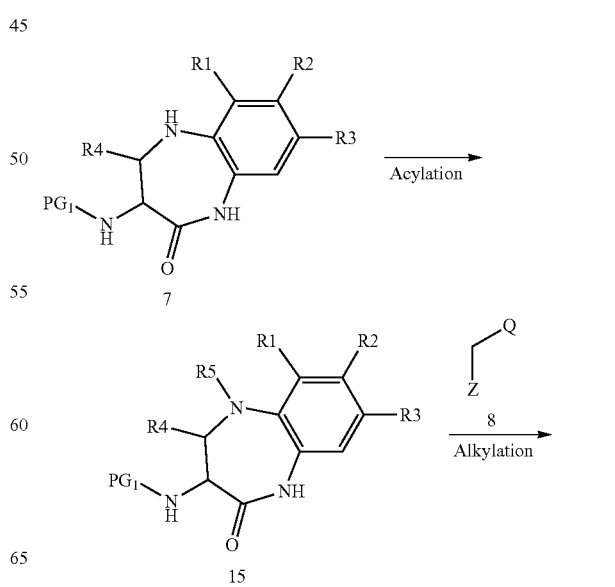

A suitably protected 2-amino-3-aminopropionic acid of general formula 2, where PG2 is an optional carboxylic acid protecting group, and a substituted or unsubstituted 1-fluoro-2-nitrobenzene of general formula 3 can be reacted with a base to give compounds of general formula 4. Compounds of general formula 4 can be reacted under reducing conditions to provide compounds of general formula 5. The reduction methods can include catalytic hydrogenation and chemical reduction. The optional carboxylic acid protecting group PG2 in compounds of general formula 5 can be removed to afford compounds of general formula 6. Compounds of general formula 6 can be subjected to dehydrating conditions to afford compounds of general formula 7. Compounds of general structure 7 can be reacted with compounds of general structure 8 to form compounds of general structure 9, where Q is a suitable leaving group. The amine protecting group PG1 can be removed to afford compound of general formula 10. A suitably protected μ-amino-acid of general structure 11 can be coupled to compounds of general structure 12. Compounds of general formula 12 can be treated with acylating reagents to provide compounds of general formula 13. The amine protecting group PG3 can be removed to afford compound of general formula 1.

-continued

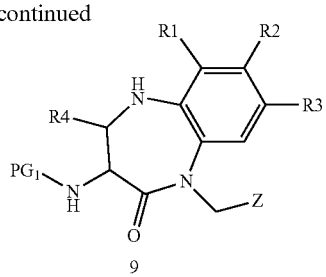

9

The order of the steps can be varied, as shown in Scheme 2.

Scheme 3

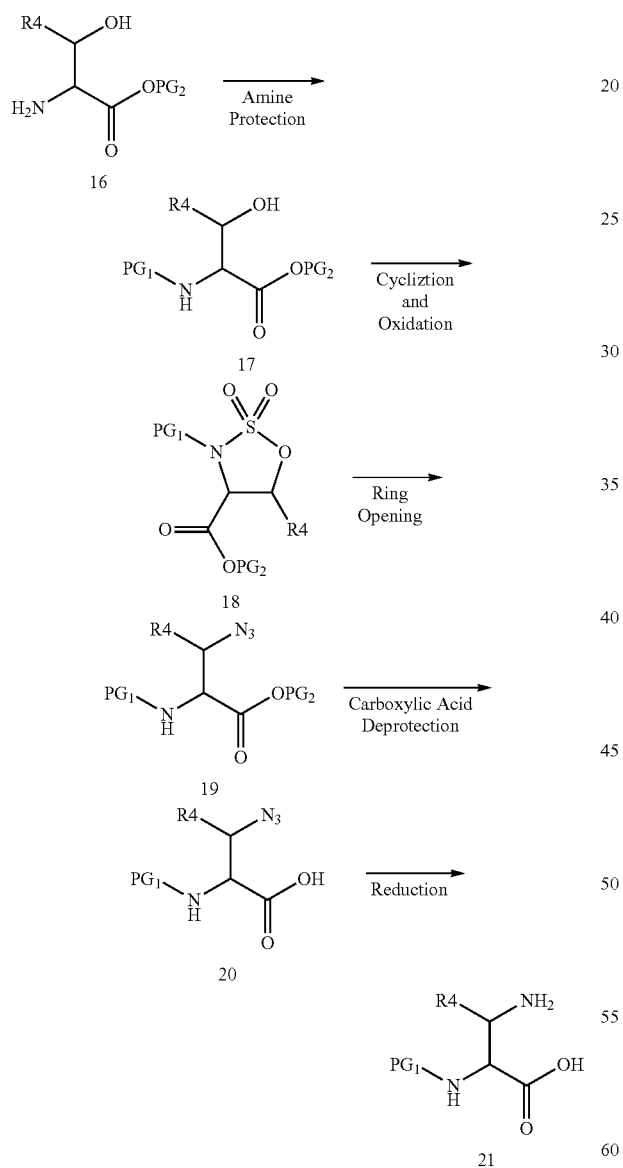

Where a suitably protected 2-amino-3-aminopropionic acid of general formula 2, where the optional protecting group PG2 is absent, is not known in the literature or commercially available, it can be synthesized from known or commercially available 2-amino-3-hydroxypropionic acid of general formula 16. The amino group in compounds of general formula 16 can be protected with a suitable protecting group, PG1. Compounds of general formula 17 can be reacted with appropriate reagent to provide compounds of general formula 18. Compounds of general formula 18 can be treated with a source of azide ion to afford compounds of general formula 20. Compounds of general formula 20 can be reacted under reducing conditions to afford compounds of general formula 21. The reduction methods can include catalytic hydrogenation and chemical reduction. Those skilled in the art will recognize that compounds of general formula 21 are the same as compounds of general formula 2 where the optional protecting group PG2 is absent.

Methods to perform the above described reactions and processes would be apparent to those of ordinary skill in the art based on the present disclosure, or can be deduced in analogy from the examples. Starting materials are commercially available or can be made by methods analogous to those described in the Examples below.

Crystal Forms

When the compounds of the invention are solids, it is understood by those skilled in the art that these compounds, and their salts, may exist in different crystal or polymorphic forms, all of which are intended to be within the scope of the present invention and specified formulas.

EXAMPLES

The compounds of the present invention may be synthesized according to known techniques. The following examples and references are provided to aid the understanding of the present invention. The examples are not intended, however, to limit the invention, the true scope of which is set forth in the appended claims. The names of the final products in the examples were generated using AutoNom 2000 Add-in v4.0 SP2 (function in ISIS Draw, ElsevierMDL), or AutoNom 2000 TT v4.01.305 (ElsevierMDL), or functions available in ChemDraw Pro Control 11.0.2 (CambridgeSoft Corp.), or Struct=Name feature of electronic notebooks.

Example 1

(S)-N-[(2S,3S)-1-(4-acetyl-benzoyl)-5-(5-bromo-2-methoxy-naphthalen-1-ylmethyl)-2-methyl-4-oxo-2,3,4,5-tetrahydro-1H-benzo[b][1,4]diazepin-3-yl]-2-methyl amino-propionamide hydrochloride

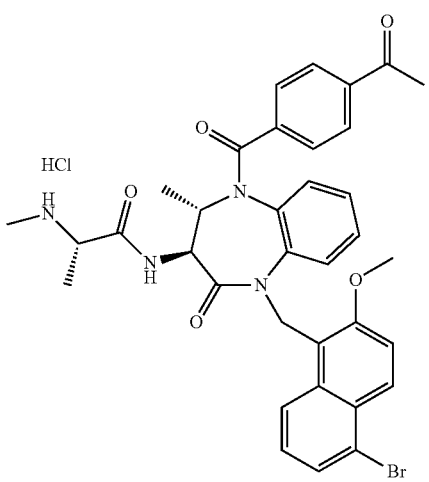 [SMILES: CN[C@@H](C)C(=O)N[C@@H]1C(=O)N(Cc2c(OC)ccc3c(Br)cccc23)c2ccccc2N(C(=O)c2ccc(C(C)=O)cc2)[C@H]1C ; Cl]

Step 1-A: A suspension (2S,3S)-3-amino-2-tert-butoxycarbonylamino-butyric acid methyl ester (6.0 g, 20.7 mmol) (prepared according to WO 2010031750), 1-fluoro-2-nitrobenzene (4.37 g, 31.0 mmol) and sodium hydrogen carbonate (5.21 g, 62 mmol) in N,N-dimethylformamide (60 ml) was heated to 85° C. for 24 h. The reaction was cooled, concentrated in vacuo and the residue was diluted with water (100 ml) and extracted with ethyl acetate (2×150 ml). The organic layers were combined, washed with water (1×50 mL), brine (1×50 mL), dried over sodium sulfate, filtered and concentrated in vacuo. The crude product was purified by chromatography over silica gel gradient eluted with 5 to 60% v/v ethyl acetate hexanes to give (2S,3S)-2-tert-butoxycarbonylamino-3-(2-nitro-phenylamino)-butyric acid methyl ester (5.71 g, 78%).

Step 1-B: To a solution of (2S,3S)-2-tert-butoxycarbonylamino-3-(2-nitro-phenylamino)-butyric acid methyl ester (5.71 g, 16.2 mmol) in dioxane water (1:1, 100 ml) was added an aqueous solution of 2.5 M lithium hydroxide (31 ml) and the reaction was stirred at ambient temperature for 2 h. The reaction was made acidic with 10% aqueous citric acid, diluted with water (60 ml) and extracted with ethyl acetate (2×100 mL). The organic layers were combined, washed with water (1×50 mL), brine, dried over sodium sulfate, filtered and concentrated in vacuo to give (2S,3S)-2-tert-butoxycarbonylamino-3-(2-nitro-phenylamino)-butyric acid which was carried to the subsequent step without purification (5.48 g, 99%).

Step 1-C: A flask containing a solution of (2S,3S)-2-tert-butoxycarbonylamino-3-(2-nitro-phenylamino)-butyric acid (5.8 g, 17.1 mmol) in ethanol (60 ml) was purged with nitrogen followed by the addition of 10% palladium on carbon (600 mg). The atmosphere above the ethanol solution was exchanged for hydrogen and the reaction mixture stirred vigorously for 30 minutes at atmospheric pressure. The reaction mixture was filtered through a pad of celite and concentrated in vacuo to give (2S,3S)-3-(2-amino-phenylamino)-2-tert-butoxycarbonylamino-butyric acid which was used in the subsequent step without further purification (5.29 g, 100%).

Step 1-D: To a solution of (2S,3S)-3-(2-amino-phenylamino)-2-tert-butoxycarbonylamino-butyric acid (5.29 g, 17.1 mmol) in N,N-dimethylformamide (50 ml) was added 1-ethyl-3-(3-dimethylaminopropyl)carbodiimide hydrochloride (4.26 g, 22.2 mmol) and the reaction was stirred at ambient temperature for 24 h. The mixture was concentrated in vacuo, diluted with water (100 ml) and extracted with ethyl acetate (2×100 mL). The organic layers were combined, dried over sodium sulfate, filtered and concentrated in vacuo to give ((2S,3S)-2-methyl-4-oxo-2,3,4,5-tetrahydro-1H-benzo[b][1,4]diazepin-3-yl)-carbamic acid tert-butyl ester which was used in the subsequent step without further purification (4.55 g, 91%).

Step 1-E: Phosphoryl chloride (0.16 ml, 1.72 mmol) was added to a solution of ((2S,3S)-2-methyl-4-oxo-2,3,4,5-tetrahydro-1H-benzo[b][1,4]diazepin-3-yl)-carbamic acid tert-butyl ester (0.5 g, 1.72 mmol) and 4-acetyl-benzoic acid (0.25 g, 1.54 mmol) in pyridine (15 ml) at 0° C., stirring continued for 2 h. The reaction mixture was diluted with water (50 ml) and extracted with ethyl acetate (2×60 mL). The organic layers were combined, washed with 10% aqueous citric acid (1×15 mL), water (1×15 mL) and a saturated aqueous solution of sodium hydrogen carbonate (1×15 mL) and brine. The organic extract was dried over sodium sulfate, filtered and concentrated in vacuo. The crude product was purified by chromatography over silica gel gradient eluted with 10 to 60% v/v ethyl acetate hexanes to give [(2S,3S)-1-(4-acetyl-benzoyl)-2-methyl-4-oxo-2,3,4,5-tetrahydro-1H-benzo[b][1,4]diazepin-3-yl]-carbamic acid tert-butyl ester (0.45 g, 60%).

Step 1-F: Acetyl chloride (1.0 ml, 14.1 mmol) was added dropwise to a solution of [(2S,3S)-1-(4-acetyl-benzoyl)-2-methyl-4-oxo-2,3,4,5-tetrahydro-1H-benzo[b][1,4]diazepin-3-yl]-carbamic acid tert-butyl ester (0.45 g, 1.03 mmol) in methanol at 0° C. and the reaction was allowed to warm to ambient temperature and stir for 2 h. The reaction was concentrated in vacuo to give (3S,4S)-5-(4-acetyl-benzoyl)-3-amino-4-methyl-1,3,4,5-tetrahydro-benzo[b][1,4]diazepin-2-one hydrochloride which was used in the subsequent step without further purification (0.36 g, 100%).

Step 1-G: To a solution of (3S,4S)-5-(4-acetyl-benzoyl)-3-amino-4-methyl-1,3,4,5-tetrahydro-benzo[b][1,4]diazepin-2-one hydrochloride (0.39 g, 1.03 mmol) in N,N-dimethylformamide (6.0 mL) at 0° C. was added (S)-2-(tert-butoxycarbonyl-methyl-amino)-propionic acid (0.23 g, 1.13 mmol), N,N-diisopropylethylamine (0.72 mL, 4.12 mmol) and 0-benzotriazol-1-yl-N,N,N'N'-tetramethyluronium hexafluorophosphate (0.43 g, 1.13 mmol), the reaction was stirred for 2 h. The reaction mixture was diluted with water (50 ml) and extracted with ethyl acetate (2×40 mL). The organic layers were combined, washed with a saturated aqueous solution of sodium hydrogen carbonate (1×20 mL), water (1×25 mL), dried over sodium sulfate, filtered through a plug of silica gel and concentrated in vacuo to give {(S)-1-[(2S,3S)-1-(4-acetyl-benzoyl)-2-methyl-4-oxo-2,3,4,5-tetrahydro-1H-benzo[b][1,4]diazepin-3-ylcarbamoyl]-ethyl}-methyl-carbamic acid tert-butyl ester which was used in the subsequent step without further purification (0.53 g, 98%).

Step 1-H: To a solution of {(S)-1-[(2S,3S)-1-(4-acetyl-benzoyl)-2-methyl-4-oxo-2,3,4,5-tetrahydro-1H-benzo[b][1,4]diazepin-3-ylcarbamoyl]-ethyl}-methyl-carbamic acid tert-butyl ester (60 mg, 0.115 mmol) in N,N-dimethylformamide (1.0 mL) was added cesium carbonate (94 mg, 0.287 mmol), 5-bromo-1-chloromethyl-2-methoxy-naphthalene (39.3 mg, 0.138 mmol) and sodium iodide (17.2 mg, 0.115 mmol) and the reaction was stirred for 2 h. The reaction mixture was diluted with water (10 ml) and extracted with ethyl acetate (2×15 mL). The organic layers were combined, washed with brine (1×10 mL), dried over sodium sulfate, filtered and concentrated in vacuo. The crude product was purified by chromatography over silica gel gradient eluted with 10 to 70% v/v ethyl acetate hexanes to give {(S)-1-[(2S,3S)-1-(4-acetyl-benzoyl)-5-(5-bromo-2-methoxy-naphthalen-1-ylmethyl)-2-methyl-4-oxo-2,3,4,5-tetrahydro-1H-benzo[b][1,4]diazepin-3-ylcarbamoyl]-ethyl}-methyl-carbamic acid tert-butyl ester (40 mg, 45%).

Step 1-I: Acetyl chloride (0.5 ml, 7.03 mmol) was added dropwise to a solution of {(S)-1-[(2S,3S)-1-(4-acetyl-benzoyl)-5-(5-bromo-2-methoxy-naphthalen-1-ylmethyl)-2-methyl-4-oxo-2,3,4,5-tetrahydro-1H-benzo[b][1,4]diazepin-3-ylcarbamoyl]-ethyl}-methyl-carbamic acid tert-butyl ester (40 mg, 0.52 mmol) in methanol at 0° C. and the reaction was allowed to warm to ambient temperature and stir for 2 h. The reaction was concentrated in vacuo and the residue was triturated with diethyl ether, filtered and dried to give (S)-N-[(2S,3S)-1-(4-acetyl-benzoyl)-5-(5-bromo-2-methoxy-naphthalen-1-ylmethyl)-2-methyl-4-oxo-2,3,4,5-tetrahydro- 1H-benzo[b][1,4]diazepin-3-yl]-2-methylamino-propionamide hydrochloride (30 mg, 82%). LR-MS [M+H+] 672, 673

Example 2

(S)-N-[(2S,3S)-1-(4-acetyl-benzoyl)-5-(6-bromo-2-methoxy-naphthalen-1-ylmethyl)-2-methyl-4-oxo-2,3,4,5-tetrahydro-1H-benzo[b][1,4]diazepin-3-yl]-2-methylamino-propionamide hydrochloride

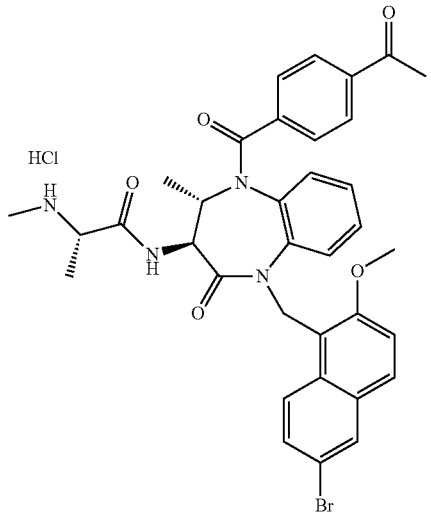 [SMILES: CN[C@@H](C)C(=O)N[C@@H]1C(=O)N(Cc2c(OC)ccc3cc(Br)ccc23)c2ccccc2N(C(=O)c2ccc(C(C)=O)cc2)[C@H]1C ; Cl]

Prepared by the same method as described in Example 1 above except 6-bromo-1-chloromethyl-2-methoxy-naphthalene was used in place of 5-bromo-1-chloromethyl-2-methoxy-naphthalene in step 2-H. LR-MS [M+H+]+672, 673

Example 3

(S)-N-{(2S,3S)-1-(4-acetyl-benzo yl)-5-[1-(2-cyano-phenyl)-1H-indazol-3-ylmethyl]-2-methyl-4-oxo-2,3,4,5-tetrahydro-1H-benzo[b][1,4]diazepin-3-yl}-2-methylamino-propionamide hydrochloride

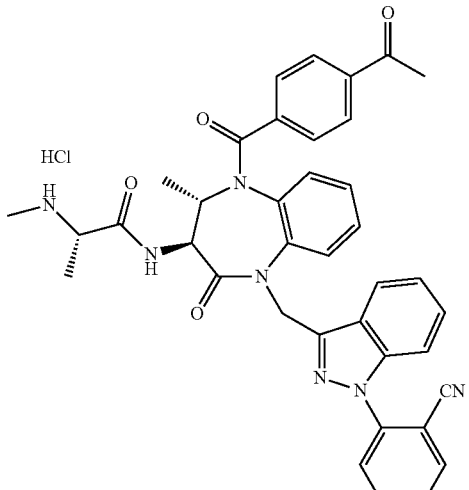

Prepared by the same method as described in Example 1 above except 2-(3-chloromethyl-indazol-1-yl)-benzonitrile was used in place of 5-bromo-1-chloromethyl-2-methoxy-naphthalene in step 3-H. LR-MS [M+H+]654

Example 4

(S)-N-[(2S,3S)-1-(4-acetyl-benzoyl)-5-(3-cyclopropyl-quinolin-4-ylmethyl)-2-methyl-4-oxo-2,3,4,5-tetrahydro-1H-benzo[b][1,4]diazepin-3-yl]-2-methylamino-propionamide dihydrochloride

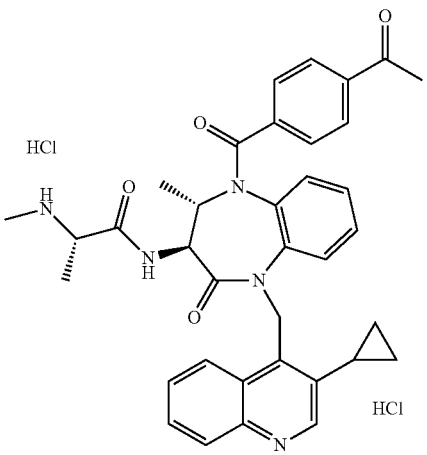 [SMILES: CN[C@@H](C)C(=O)N[C@@H]1C(=O)N(Cc2c(C3CC3)cnc3ccccc23)c2ccccc2N(C(=O)c2ccc(C(C)=O)cc2)[C@H]1C ; Cl ; Cl]

Prepared by the same method as described in Example 1 above except methanesulfonic acid 3-cyclopropyl-quinolin-4-ylmethyl ester was used in place of 5-bromo-1-chloromethyl-2-methoxy-naphthalene in step in step 4-H. LR-MS [M+H+]604

Example 5

(S)-N-[(3S,4S)-1-(6-bromo-2-methoxy-naphthalen-1-ylmethyl)-5-(4-cyano-benzoyl)-4-methyl-2-oxo-2,3,4,5-tetrahydro-1H-benzo[b][1,4]diazepin-3-yl]-2-methylamino-propionamide hydrochloride

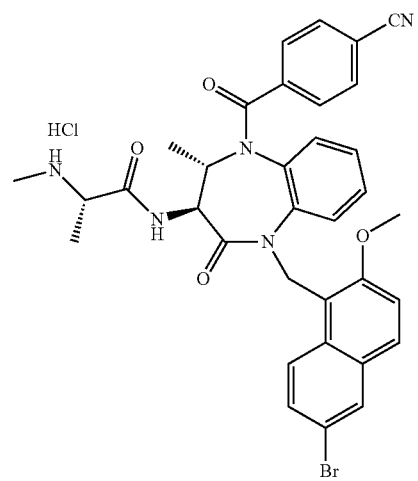

Prepared by the same method as described in Example 2 except 4-cyano-benzoic acid was used in place of 4-acetyl-benzoic acid in step 5-E and step 5-H was performed before step 5-F. LR-MS [M+H+]655; 656

Example 6

(S)-N-{(3S,4S)-7-cyano-5-(4-cyano-benzoyl)-1-[1-(2-cyano-phenyl)-1H-indazol-3-ylmethyl]-4-methyl-2-oxo-2,3,4,5-tetrahydro-1H-benzo[b][1,4]diazepin-3-yl}-2-methylamino-propionamide hydrochloride

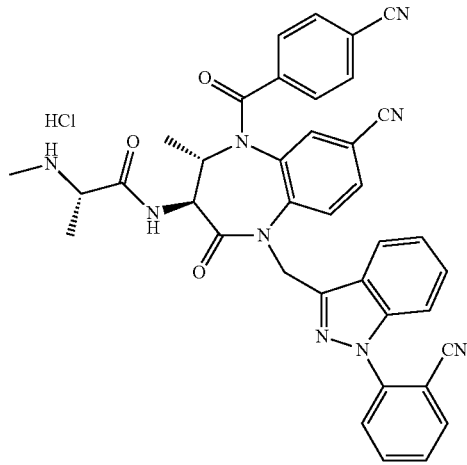 [SMILES: CN[C@@H](C)C(=O)N[C@@H]1C(=O)N(Cc2nn(-c3ccccc3C#N)c3ccccc23)c2ccc(C#N)cc2N(C(=O)c2ccc(C#N)cc2)[C@H]1C ; Cl]

Prepared by the same method as described in Example 1 above except that (i) 3-fluoro-4-nitro-benzonitrile was used in place 1-fluoro-2-nitrobenzene in step 6-A; (ii) 2-(3-chloromethyl-indazol-1-yl)-benzonitrile was used in place of 5-bromo-1-chloromethyl-2-methoxy-naphthalene in step 6-H which was performed before step 6-E; (iii) 4-cyano-benzoic acid was used in place of 4-acetyl-benzoic acid in step 6-E; and (iv) 20% v/v trifluoroacetic acid dichloromethane to give the trifluoroacetate salt was used in place of acetyl chloride methanol. LR-MS [M+H]+ 662

Example 7

(S)-N-((3S,4S)-1-((6-bromo-2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride

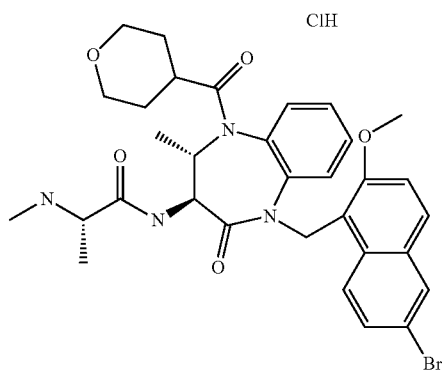 [SMILES: Cl ; CN[C@@H](C)C(=O)N[C@@H]1C(=O)N(Cc2c(OC)ccc3cc(Br)ccc23)c2ccccc2N(C(=O)C2CCOCC2)[C@H]1C]

Step 1: To a 0° C. solution of tert-butyl(2S,3S)-2-methyl-4-oxo-2,3,4,5-tetrahydro-1H-benzo[b][1,4]diazepin-3-yl-carbamate (prepared as in Example 1, 330 mg, 1.13 mmol) in methylene chloride (10 ml) was added pyridine (277 µl, 3.4 mmol) and tetrahydro-2H-pyran-4-carbonyl chloride (185 mg, 1.25 mmol). It was stirred at 0° C. for one hour and then warmed to room temperature and stirred overnight. After this time another portion of tetrahydro-2H-pyran-4-carbonyl chloride (252 mg, 1.70 mmol) was added and the reaction mixture was stirred at room temperature another 3 h. After this time the reaction mixture was diluted with methylene chloride (30 mL), washed with a saturated aqueous sodium bicarbonate solution (30 mL), and saturate aqueous sodium chloride solution (30 mL), the organic layer was then dried over sodium sulfate, filtered to remove the drying agent, and concentrated in vacuo. The crude material was then purified on an Intelliflash 280 system (12 g silica gel column, 20-65% ethyl acetatehexanes) to afford tert-butyl(2S,3S)-2-methyl-4-oxo-1-(tetrahydro-2H-pyran-4-carbonyl)-2,3,4,5-tetrahydro-1H-benzo[b][1,4]diazepin-3-ylcarbamate (210 mg, 46%) as a white foam: LC-MS m/z 426 [M+Na]+.

Step 2: A room temperature solution of tert-butyl(2S,3S)-2-methyl-4-oxo-1-(tetrahydro-2H-pyran-4-carbonyl)-2,3,4,5-tetrahydro-1H-benzo[b][1,4]diazepin-3-ylcarbamate (205 mg, 0.51 mmol) in a 4 M solution of hydrochloric acid in dioxane (2.5 mL) was stirred for 1.5 h. After this time, the reaction mixture was concentrated in vacuo to afford (3S,4S)-3-amino-4-methyl-5-(tetrahydro-2H-pyran-4-carbonyl)-4,5-dihydro-1H-benzo[b][1,4]diazepin-2(3H)-one hydrochloride (theo. yield 173 mg) which was used without purification.

Step 3: To a room temperature solution of (3S,4S)-3-amino-4-methyl-5-(tetrahydro-2H-pyran-4-carbonyl)-4,5-dihydro-1H-benzo[b][1,4]diazepin-2(3H)-one hydrochloride (173 mg, 509 µmol) in N,N-dimethylformamide (2 ml) was added Boc-N-methyl-L-alanine (114 mg, 560 µmol), N,N-diisopropylethylamine (440 µl, 2.55 mmol), and HBTU (212 mg, 560 µmol). The reaction was stirred at room temperature for 2 h. After this time, the reaction was diluted with ethyl acetate (20 mL), washed with a saturated aqueous sodium bicarbonate solution (20 mL) and the aqueous layer was then extracted with ethyl acetate (3×10 mL) and the combined organics were washed with a saturated aqueous sodium chloride solution (20 mL), dried over sodium sulfate, filtered, and the filterate concentrated in vacuo. The crude material was purified using an Initelliflash 280 system (4 g silica gel column Varian brand, 20-90% ethyl acetatehexanes) to afford tert-butyl methyl((S)-1-((2S,3S)-2-methyl-4-oxo-1-(tetrahydro-2H-pyran-4-carbonyl)-2,3,4,5-tetrahydro-1H-benzo[b][1,4]diazepin-3-ylamino)-1-oxopropan-2-yl)carbamate (238 mg, 96%): LC-MS m/z 487 [M-H]-.

Step 4: To a room temperature solution of tert-butyl methyl (S)-1-((2S,3S)-2-methyl-4-oxo-1-(tetrahydro-2H-pyran-4-carbonyl)-2,3,4,5-tetrahydro-1H-benzo[b][1,4]diazepin-3-ylamino)-1-oxopropan-2-yl)carbamate (75 mg, 154 µmol) in N,N-dimethylformamide (500 µl) was added 6-bromo-1-(chloromethyl)-2-methoxynaphthalene (53 mg, 184 µmol), cesium carbonate (65 mg, 200 µmol), and sodium iodide (30 mg, 200 µmol). The reaction was stirred at room temperature for 16 h. After this time, the reaction mixture was diluted with ethyl acetate (20 mL), washed with water (20 mL) the aqueous layer was then extracted with ethyl acetate (2×20 mL) and the organic layers combined and then washed with a saturated aqueous sodium chloride solution (30 mL), dried over magnesium sulfate, filtered, and the filterate concentrated in vacuo. The crude material was purified by flash chromatography (Intelliflash 280 system; 4 g silica gel Super Flash column from Varian, 10-65% ethyl acetatehexanes) to afford tert-butyl(S)-1-((3S,4S)-1-((6-bromo-2-methoxynaphthalen-1-yl)methyl)-4-methyl-2-oxo-5-(tetrahydro-2H-pyran- 4-carbonyl)-2,3,4,5-tetrahydro-1H-benzo[b][1,4]diazepin-3-ylamino)-1-oxopropan-2-yl(methyl)carbamate (59 mg, 52%) as a yellow oil: LC-MS m/z 759 [M+Na]+.

Step 5: A solution of tert-butyl(S)-1-((3S,4S)-1-((6-bromo-2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-ylamino)-1-oxopropan-2-yl (methyl)carbamate (55 mg, 75 μmol) in methanol (500 μl) at room temperature was treated with a 2 M hydrochloric acid in diethyl ether solution (1.3 ml) and stirred for 3.5 h. The reaction was then concentrated in vacuo, dissolved in water and placed on a lyophilizer over night to afford (S)-N-((3S,4S)-1-((6-bromo-2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino) propanamide hydrochloride (43 mg, 86%) as an off white powder: LC-MS m/z 637 [M+H]+.

Example 8

(S)-N-((3S,4S)-1-((5-bromo-2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride

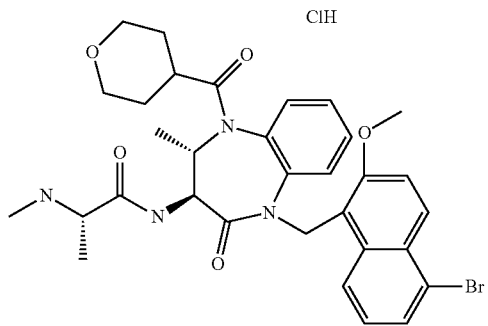 [SMILES: Cl ; CN[C@@H](C)C(=O)N[C@@H]1C(=O)N(Cc2c(OC)ccc3c(Br)cccc23)c2ccccc2N(C(=O)C2CCOCC2)[C@H]1C]

Step 1: To a room temperature solution of tert-butyl methyl ((S)-1-((2S,3S)-2-methyl-4-oxo-1-(tetrahydro-2H-pyran-4-carbonyl)-2,3,4,5-tetrahydro-1H-benzo[b][1,4]diazepin-3-ylamino)-1-oxopropan-2-yl)carbamate (prepared as in Example RK-1, Step 3, 75 mg, 154 μmol) in N,N-dimethylformamide (500 μl) was added 5-bromo-1-(chloromethyl)-2-methoxynaphthalene (53 mg, 184 μmol), cesium carbonate (65 mg, 200 μmol), and sodium iodide (30 mg, 200 μmol). The reaction was stirred at room temperature for 16 h. After this time, the reaction mixture was diluted with ethyl acetate (20 mL), washed with water (20 mL) the aqueous layer was then extracted with ethyl acetate (2×20 mL) and the organic layers combined and then washed with a saturated aqueous sodium chloride solution (30 mL), dried over magnesium sulfate, filtered, and the filterate concentrated in vacuo. The crude material was purified by flash chromatography (Intelliflash 280 system; 4 g silica gel Super Flash column from Varian, 10-65% ethyl acetatehexanes) to afford tert-butyl(S)-1-((3S,4S)-1-((5-bromo-2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-ylamino)-1-oxopropan-2-yl)methyl)carbamate (48 mg, 42%) as a yellow oil: LC-MS m/z 759 [M+Na]+.

Step 2: A solution of tert-butyl(S)-1-((3S,4S)-1-((5-bromo-2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-ylamino)-1-oxopropan-2-yl (methyl)carbamate (45 mg, 61 μmol) in methanol (500 μl) at room temperature was treated with a 2 M hydrochloric acid in diethyl ether solution (1.3 ml) and stirred for 3.5 h. The reaction was then concentrated in vacuo, dissolved in water and placed on a lyophilizer over night to afford (S)-N-((3S,4S)-1-((5-bromo-2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (36 mg, 88%) as a light yellow powder: LC-MS m/z 637 [M+H]+.

Example 9

(S)-N-((3S,4S)-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride

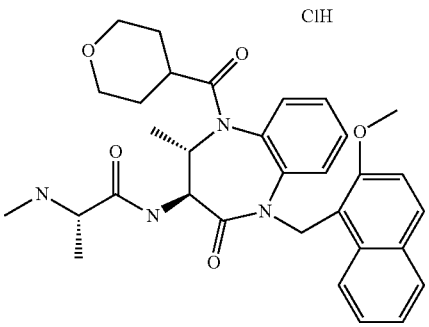 [SMILES: Cl ; CN[C@@H](C)C(=O)N[C@@H]1C(=O)N(Cc2c(OC)ccc3ccccc23)c2ccccc2N(C(=O)C2CCOCC2)[C@H]1C]

Step 1: To a room temperature solution of tert-butyl methyl ((S)-1-((2S,3S)-2-methyl-4-oxo-1-(tetrahydro-2H-pyran-4-carbonyl)-2,3,4,5-tetrahydro-1H-benzo[b][1,4]diazepin-3-ylamino)-1-oxopropan-2-yl)carbamate (prepared as in Example RK-1, Step 3, 75 mg, 154 μmol) in N,N-dimethylformamide (500 μl) was added 1-(chloromethyl)-2-methoxynaphthalene (38 mg, 184 μmol), cesium carbonate (65 mg, 200 μmol), and sodium iodide (30 mg, 200 μmol). The reaction was stirred at room temperature for 16 h. After this time, the reaction mixture was diluted with ethyl acetate (20 mL), washed with water (20 mL) the aqueous layer was then extracted with ethyl acetate (2×20 mL) and the organic layers combined and then washed with a saturated aqueous sodium chloride solution (30 mL), dried over magnesium sulfate, filtered, and the filterate concentrated in vacuo. The crude material was purified by flash chromatography to afford tert-butyl(S)-1-((3S,4S)-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-ylamino)-1-oxopropan-2-yl(methyl)carbamate (53 mg, 52%) as a light yellow foam: LC-MS m/z 681 [M+Na]+.

Step 2: A solution of tert-butyl(S)-1-((3S,4S)-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-ylamino)-1-oxopropan-2-yl(methyl)carbamate (49 mg, 74 μmol) in methanol (500 μl) at room temperature was treated with a 2 M hydrochloric acid in diethyl ether solution (1.3 ml) and stirred for 3.5 h. The reaction was then concentrated in vacuo, dissolved in water and placed on a lyophilizer over night to afford (S)-N-((3S,4S)-1-((5-bromo-2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (34 mg, 77%) as a light yellow powder: LC-MS m/z 559 [M+H]+.

Example 10

(S)-N-((3S,4S)-1-((6-Bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride

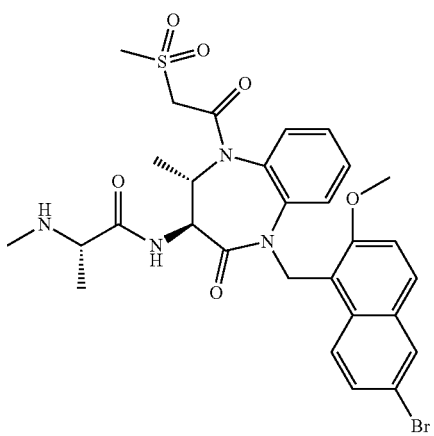 [SMILES: CN[C@@H](C)C(=O)N[C@@H]1C(=O)N(Cc2c(OC)ccc3cc(Br)ccc23)c2ccccc2N(C(=O)CS(C)(=O)=O)[C@H]1C]

Step 1: To a rt solution of tert-butyl(2S,3S)-2-methyl-1-(2-(methylsulfonyl)acetyl)-4-oxo-2,3,4,5-tetrahydro-1H-benzo[b][1,4]diazepin-3-ylcarbamate (60.3 mg, 147 μmol) in DMF (366 μl) was added 6-bromo-1-(chloromethyl)-2-methoxynaphthalene (50.2 mg, 176 μmol), cesium carbonate (62.1 mg, 191 μmol), and sodium iodide (28.6 mg, 191 μmol). The reaction was stirred at rt for 4 h, then diluted with EtOAc (30 mL), washed with H2O (30 mL) and sat. aq. NaCl (30 mL), dried over Na2SO4, filtered, and concentrated. The crude material was purified by flash chromatography to provide tert-butyl(3S,4S)-1-((6-bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-ylcarbamate (75 mg, 78% yield) as a white solid. MS m/z 682/684 (MNa)+

Step 2: A rt solution of tert-butyl(3S,4S)-1-((6-bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-ylcarbamate (75 mg, 114 μmol) in 4 M HCl in 1,4-dioxane (568 μl) was stirred for 1.5 h then concentrated. This material was taken up in DMF (380 μl) and Boc-N-methyl-L-alanine (25.5 mg, 125 μmol), N,N-diisopropylethylamine (78.9 μl, 456 μmol), and HBTU (47.6 mg, 125 μmol) were added. The reaction was stirred at rt for 20 min, then diluted with EtOAc, washed with sat. aq. NaHCO3 and sat. aq. NaCl, dried over Na2SO4, filtered, and concentrated. The crude material was purified by flash chromatography to provide tert-butyl(S)-1-((3S,4S)-1-((6-bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (81 mg, 95%) as a white solid. MS m/z 767/769 (M+Na)+

Step 3: To a rt solution of tert-butyl(S)-1-((3S,4S)-1-((6-bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (80 mg, 107 μmol) in MeOH (107 μl) was added 2 M HCl in Et2O (429 μl). The reaction was stirred at rt for 2 h then concentrated, taken up in H2O, and lyophilized to provide (S)-N-((3S,4S)-1-((6-bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride (65.7 mg, 90%) as a white solid. MS m/z 645/647 (MH)+.

Example 11

(S)-N-((3S,4S)-1-((5-Bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride

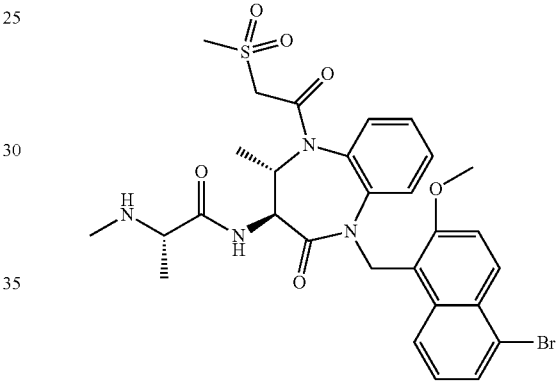

Step 1: To a rt solution of tert-butyl methyl((S)-1-((2S,3S)-2-methyl-1-(2-(methylsulfonyl)acetyl)-4-oxo-2,3,4,5-tetrahydro-1H-benzo[b][1,4]diazepin-3-ylamino)-1-oxopropan-2-yl)carbamate (46 mg, 92.6 μmol) in DMF (232 μl) was added 5-bromo-1-(chloromethyl)-2-methoxynaphthalene (31.7 mg, 111 μmol), cesium carbonate (39.2 mg, 120 μmol), and sodium iodide (18.1 mg, 120 μmol). The reaction was stirred at rt for 16 h, then diluted with EtOAc, washed with H2O and sat. aq. NaCl, dried over Na2SO4, filtered, and concentrated. The crude material was purified by flash chromatography to provide tert-butyl(S)-1-((3S,4S)-1-((5-bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (34.2 mg, 50%) as a white solid. MS m/z 767/769 (MNa)+.

Step 2: To a rt solution of tert-butyl(S)-1-((3S,4S)-1-((5-bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (33.8 mg, 45.3 μmol) in MeOH (45.3 μl) was added 2 M HCl in Et2O (181 μl). The reaction was stirred at rt for 3 h, then concentrated, taken up in H2O, and lyophilized to provide (S)-N-((3S,4S)-1-((5-bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-

(methylamino)propanamide hydrochloride (29.0 mg, 94%) as a white solid. MS m/z 645/647 (MH)+.

Example 12

(S)-N-((3S,4S)-1-((7-Methoxy-2-oxo-2H-chromen-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate

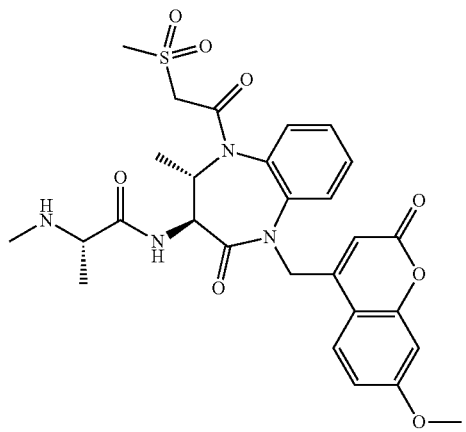

Step 1: To a rt solution of tert-butyl methyl((S)-1-((2S,3S)-2-methyl-1-(2-(methylsulfonyl)acetyl)-4-oxo-2,3,4,5-tetrahydro-1H-benzo[b][1,4]diazepin-3-ylamino)-1-oxopropan-2-yl)carbamate (60 mg, 121 μmol) in DMF (302 μl) was added 4-(bromomethyl)-7-methoxycoumarin (35.8 mg, 133 μmol), cesium carbonate (47.2 mg, 145 μmol), and sodium iodide (21.7 mg, 145 μmol). The reaction was stirred at rt for 8 h, then diluted with EtOAc, washed with H2O and sat. aq. NaCl, dried over Na2SO4, filtered, and concentrated. The crude material was purified by flash chromatography to provide tert-butyl(S)-1-((3S,4S)-1-((7-methoxy-2-oxo-2H-chromen-4-yl)methyl)-4-methyl-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (44.3 mg, 54%) as a white solid. MS m/z 707 (MNa)+.

Step 2: To a rt solution of tert-butyl(S)-1-((3S,4S)-1-((7-methoxy-2-oxo-2H-chromen-4-yl)methyl)-4-methyl-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (42.7 mg, 62.4 μmol) in CH2Cl2 (249 μl) was added TFA (62.4 μl). The reaction was stirred at rt for 1.5 h, then concentrated, taken up in H2O, and lyophilized to provide (S)-N-((3S,4S)-1-((7-methoxy-2-oxo-2H-chromen-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino) propanamide 2,2,2-trifluoroacetate (41.2 mg, 95%) as a white solid. MS m/z 585 (MH)+.

Example 13

(S)-N-((3S,4S)-1-((2-Methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride

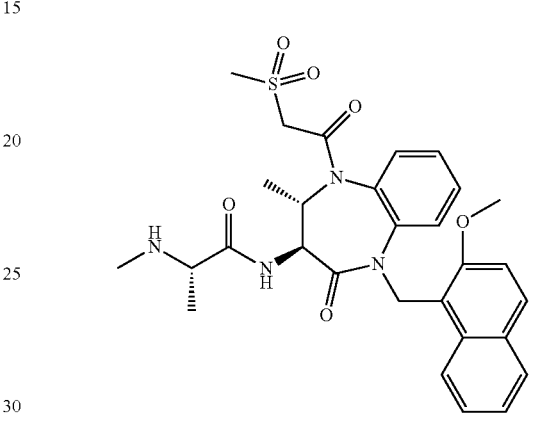

Step 1: To a rt solution of tert-butyl methyl((S)-1-((2S,3S)-2-methyl-1-(2-(methylsulfonyl)acetyl)-4-oxo-2,3,4,5-tetrahydro-1H-benzo[b][1,4]diazepin-3-ylamino)-1-oxopropan-2-yl)carbamate (141 mg, 284 μmol) in DMF (710 μl) was added 1-(chloromethyl)-2-methoxynaphthalene (64.6 mg, 312 μmol), cesium carbonate (111 mg, 341 μmol), and sodium iodide (51.1 mg, 341 μmol). The reaction was stirred at rt for 16 h, then diluted with EtOAc, washed with H2O and sat. aq. NaCl, dried over Na2SO4, filtered, and concentrated. The crude material was purified by flash chromatography to provide tert-butyl(S)-1-((3S,4S)-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (151 mg, 80%) as a white solid. MS m/z 689 (MNa)+.

Step 2: A rt solution of tert-butyl(S)-1-((3S,4S)-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-ylamino)-1-oxopropan-2-yl)methyl)carbamate (150 mg, 225 μmol) in 4 M HCl in dioxane (1.12 ml) was stirred for 2 h. The reaction was diluted with Et2O and the solids were collected by vacuum filtration, taken up in H2O, and lyophilized to provide (S)-N-((3S,4S)-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin- 3-yl)-2-(methylamino)propanamide hydrochloride (114.5 mg, 84%) as a white solid. MS m/z 567 (MH)+.

Example 14

(S)-N-((2S,3S)-2-Methyl-5-((3-methylquinolin-4-yl)methyl)-1-(2-(methylsulfonyl)acetyl)-4-oxo-2,3,4,5-tetrahydro-1H-benzo[b][1,4]diazepin-3-yl)-2-(methylamino)propanamide hydrochloride

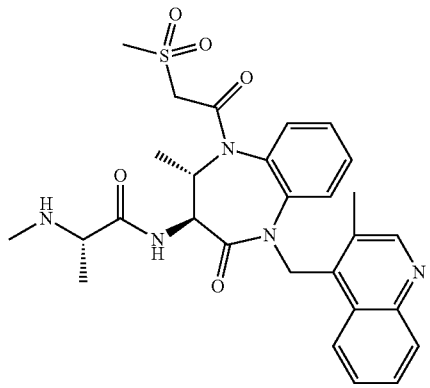 [SMILES: CN[C@@H](C)C(=O)N[C@@H]1C(=O)N(Cc2c(C)cnc3ccccc23)c2ccccc2N(C(=O)CS(C)(=O)=O)[C@H]1C]

Step 1: To a rt suspension of (3-methylquinolin-4-yl)methanol (90 mg, 520 μmol) in CH2Cl2 (5.2 ml) was added triethylamine (145 μl, 1.04 mmol), followed by methanesulfonyl chloride (48.4 μl, 624 μmol), dropwise. The reaction was stirred at rt for 2 h, then diluted with CH2Cl2, washed with H2O and sat. aq. NaCl, dried over Na2SO4, filtered, and concentrated. This material was mixed with tert-butyl methyl ((S)-1-((2S,3S)-2-methyl-1-(2-(methylsulfonyl)acetyl)-4-oxo-2,3,4,5-tetrahydro-1H-benzo[b][1,4]diazepin-3-ylamino)-1-oxopropan-2-yl)carbamate (167 mg, 336 μmol), cesium carbonate (142 mg, 437 μmol), and sodium iodide (65.5 mg, 437 μmol) in DMF (841 μl). The reaction was stirred at rt for 3.5 days, then diluted with EtOAc, washed with H2O and sat. aq. NaCl, dried over Na2SO4, filtered, and concentrated. The crude material was purified by flash chromatography to provide tert-butyl methyl((S)-1-((2S,3S)-2-methyl-5-((3-methylquinolin-4-yl)methyl)-1-(2-(methylsulfonyl)acetyl)-4-oxo-2,3,4,5-tetrahydro-1H-benzo[b][1,4]diazepin-3-ylamino)-1-oxopropan-2-yl)carbamate (142 mg, 65%) as a white solid. MS m/z 652 (MH)+.

Step 2: A rt suspension of tert-butyl methyl((S)-1-((2S,3S)-2-methyl-5-((3-methylquinolin-4-yl)methyl)-1-(2-(methylsulfonyl)acetyl)-4-oxo-2,3,4,5-tetrahydro-1H-benzo[b][1,4]diazepin-3-ylamino)-1-oxopropan-2-yl)carbamate (140 mg, 215 μmol) in 4 M HCl in dioxane (1.07 ml) was stirred for 2 h. The reaction was diluted with Et2O and the solids were collected by vacuum filtration, taken up in MeCN—H2O, and lyophilized to provide (S)-N-((2S,3S)-2-methyl-5-((3-methylquinolin-4-yl)methyl)-1-(2-(methylsulfonyl)acetyl)-4-oxo-2,3,4,5-tetrahydro-1H-benzo[b][1,4]diazepin-3-yl)-2-(methylamino)propanamide hydrochloride (113.4 mg, 90%) as a white solid. MS m/z 552 (MH)+.

Example 15

(S)-N-((3S,4S)-1-((2-Chloro-3-methylquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride

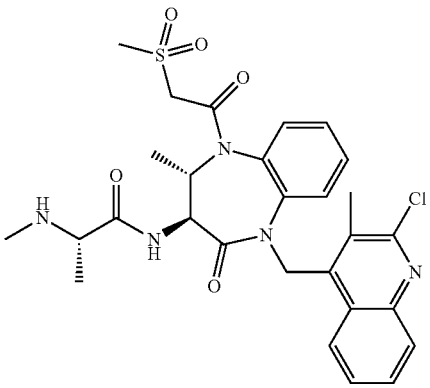 [SMILES: CN[C@@H](C)C(=O)N[C@@H]1C(=O)N(Cc2c(C)c(Cl)nc3ccccc23)c2ccccc2N(C(=O)CS(C)(=O)=O)[C@H]1C]

Step 1: To a rt suspension of (2-chloro-3-methylquinolin-4-yl)methanol (61 mg, 294 μmol) in CH2Cl2 (2.94 ml) was added triethylamine (81.9 μl, 588 μmol), followed by methanesulfonyl chloride (27.3 μl, 353 μmol), dropwise. The reaction was stirred at rt for 1.5 h, then diluted with CH2Cl2, washed with H2O and sat. aq. NaCl, dried over Na2SO4, filtered, and concentrated. This material was mixed with tert-butyl methyl((S)-1-((2S,3S)-2-methyl-1-(2-(methylsulfonyl)acetyl)-4-oxo-2,3,4,5-tetrahydro-1H-benzo[b][1,4]diazepin-3-ylamino)-1-oxopropan-2-yl)carbamate (100 mg, 201 μmol), cesium carbonate (85.3 mg, 262 μmol), and sodium iodide (39.2 mg, 262 μmol) in DMF (503 μl). The reaction was stirred at rt for 16 h, then diluted with EtOAc, washed with H2O and sat. aq. NaCl, dried over Na2SO4, filtered, and concentrated. The crude material was purified by flash chromatography to provide tert-butyl(S)-1-((3S,4S)-1-((2-chloro-3-methylquinolin-4-yl)methyl)-4-methyl-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (62.6 mg, 45%) as a white solid. MS m/z 708 (MNa)+.

Step 2: A rt suspension of tert-butyl(S)-1-((3S,4S)-1-((2-chloro-3-methylquinolin-4-yl)methyl)-4-methyl-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (61.6 mg, 89.8 μmol) in 4 M HCl in dioxane (449 μl) was stirred for 2 h. The reaction was diluted with Et2O and the solids were collected by vacuum filtration, taken up in MeCN—H2O, and lyophilized to provide (S)-N-((3S,4S)-1-((2-chloro-3-methylquinolin-4-yl)methyl)-4-methyl-5-(2-(methylsulfonyl)acetyl)-2-oxo-2,3,4,5-tetrahydro-1H-benzo

[b][1,4]diazepin-3-yl)-2-(methylamino)propanamide hydrochloride (44.2 mg, 79%) as a white solid. MS m/z 586 (MH)+.

Example 16

(S)-N-((2S,3S)-2-Methyl-1-(2-(methylsulfonyl)acetyl)-4-oxo-5-(quinolin-4-ylmethyl)-2,3,4,5-tetrahydro-1H-benzo[b][1,4]diazepin-3-yl)-2-(methylamino)propanamide hydrochloride

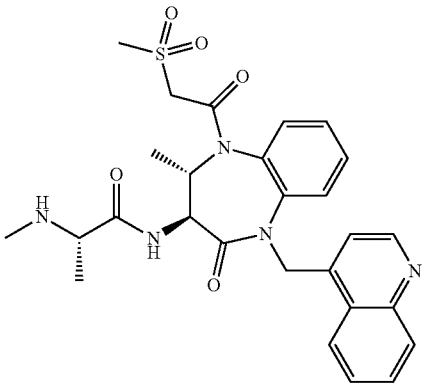 [SMILES: CN[C@@H](C)C(=O)N[C@@H]1C(=O)N(Cc2ccnc3ccccc23)c2ccccc2N(C(=O)CS(C)(=O)=O)[C@H]1C]

Step 1: To a rt solution of tert-butyl methyl((S)-1-((2S,3S)-2-methyl-1-(2-(methylsulfonyl)acetyl)-4-oxo-2,3,4,5-tetrahydro-1H-benzo[b][1,4]diazepin-3-ylamino)-1-oxopropan-2-yl)carbamate (147 mg, 296 μmol) in DMF (740 μl) was added 4-(bromomethyl)quinoline hydrobromide (135 mg, 444 μmol) and cesium carbonate (289 mg, 888 μmol). The reaction was stirred at rt for 18 h, then diluted with EtOAc, washed with H2O and sat. aq. NaCl, dried over Na2SO4, filtered, and concentrated. The crude material was purified by flash chromatography to provide tert-butyl methyl((S)-1-((2S,3S)-2-methyl-1-(2-(methylsulfonyl)acetyl)-4-oxo-5-(quinolin-4-ylmethyl)-2,3,4,5-tetrahydro-1H-benzo[b][1,4]diazepin-3-ylamino)-1-oxopropan-2-yl)carbamate (57 mg, 30%) as a white solid. MS m/z 638 (MH)+.

Step 2: A rt solution of tert-butyl methyl((S)-1-((2S,3S)-2-methyl-1-(2-(methylsulfonyl)acetyl)-4-oxo-5-(quinolin-4-ylmethyl)-2,3,4,5-tetrahydro-1H-benzo[b][1,4]diazepin-3-ylamino)-1-oxopropan-2-yl)carbamate (56 mg, 87.8 μmol) in 4 M HCl in dioxane (439 μl) was stirred for 1 h. The reaction was diluted with Et2O and the solids were collected by vacuum filtration, taken up in MeCN—H2O, and lyophilized to provide (S)-N-((2S,3S)-2-methyl-1-(2-(methylsulfonyl)acetyl)-4-oxo-5-(quinolin-4-ylmethyl)-2,3,4,5-tetrahydro-1H-benzo[b][1,4]diazepin-3-yl)-2-(methylamino)propanamide hydrochloride (43.2 mg, 75.2 μmol, 85.7% yield) as a white solid. MS m/z 538 (MH)+.

Example 17

(S)-N-((3S,4S)-1-((6-Bromo-2-methoxynaphthalen-1-yl)methyl)-5-(3-methoxypropanoyl)-4-methyl-2-oxo-2,3,4,5-tetrahydro-1H-benzo[b][1,4]diazepin-3-yl)-2-(methylamino)propanamide hydrochloride

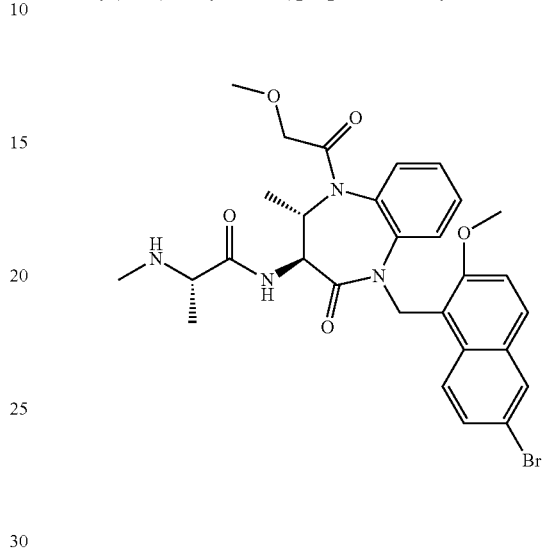

Step 1: To a rt solution of tert-butyl(S)-1-((2S,3S)-1-(3-methoxypropanoyl)-2-methyl-4-oxo-2,3,4,5-tetrahydro-1H-benzo[b][1,4]diazepin-3-ylamino)-1-oxopropan-2-yl(methyl)carbamate (46 mg, 99.5 μmol) in DMF (249 μl) was added 6-bromo-1-(chloromethyl)-2-methoxynaphthalene (34.1 mg, 119 μmol), cesium carbonate (42.1 mg, 129 μmol), and sodium iodide (19.4 mg, 129 μmol). The reaction was stirred at rt for 16 h, then diluted with EtOAc, washed with H2O and sat. aq. NaCl, dried over Na2SO4, filtered, and concentrated. The crude material was purified by flash chromatography to provide tert-butyl(S)-1-((3S,4S)-1-((6-bromo-2-methoxynaphthalen-1-yl)methyl)-5-(3-methoxypropanoyl)-4-methyl-2-oxo-2,3,4,5-tetrahydro-1H-benzo[b][1,4]diazepin-3-ylamino)-1-oxopropan-2-yl(methyl)carbamate (52.4 mg, 74%) as a white solid. MS m/z 733/735 (MNa)+.

Step 2: To a rt solution of tert-butyl(S)-1-((3S,4S)-1-((6-bromo-2-methoxynaphthalen-1-yl)methyl)-5-(3-methoxypropanoyl)-4-methyl-2-oxo-2,3,4,5-tetrahydro-1H-benzo[b][1,4]diazepin-3-ylamino)-1-oxopropan-2-yl(methyl)carbamate (51.2 mg, 71.9 μmol) in MeOH (71.9 μl) was added 2 M HCl in Et2O (288 μl). The reaction was stirred at rt for 3 h, then concentrated, taken up in H2O, and lyophilized to provide (S)-N-((3S,4S)-1-((6-bromo-2-methoxynaphthalen-1-yl)methyl)-5-(3-methoxypropanoyl)-4-methyl-2-oxo-2,3,4,5-tetrahydro-1H-benzo[b][1,4]diazepin-3-yl)-2-(methylamino)propanamide hydrochloride (42.3 mg, 91%) as a white solid. MS m/z 611/613 (MH)+.

Example 18

(S)-N-((2S,3S)-1-Acetyl-5-((3-cyclopropylquinolin-4-yl)methyl)-2-methyl-4-oxo-2,3,4,5-tetrahydro-1H-benzo[b][1,4]diazepin-3-yl)-2-(methylamino)propanamide

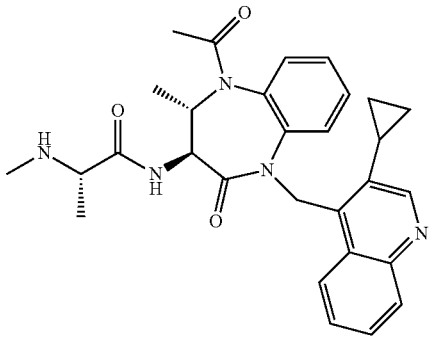 [SMILES: CN[C@@H](C)C(=O)N[C@@H]1C(=O)N(Cc2c(C3CC3)cnc3ccccc23)c2ccccc2N(C(C)=O)[C@H]1C]

Step 1: To a rt solution of tert-butyl(S)-1-((2S,3S)-1-acetyl-2-methyl-4-oxo-2,3,4,5-tetrahydro-1H-benzo[b][1,4]diazepin-3-ylamino)-1-oxopropan-2-yl(methyl)carbamate (100 mg, 239 μmol) in DMF (597 μl) was added (3-cyclopropylquinolin-4-yl)methyl methanesulfonate (79.5 mg, 287 μmol), cesium carbonate (101 mg, 311 μmol), and sodium iodide (46.6 mg, 311 μmol). The reaction was stirred at rt for 16 h, then diluted with EtOAc, washed with H2O and sat. aq. NaCl, dried over Na2SO4, filtered, and concentrated. The crude material was purified by flash chromatography to provide tert-butyl(S)-1-((2S,3S)-1-acetyl-5-((3-cyclopropylquinolin-4-yl)methyl)-2-methyl-4-oxo-2,3,4,5-tetrahydro-1H-benzo[b][1,4]diazepin-3-ylamino)-1-oxopropan-2-yl(methyl)carbamate (65 mg, 45%) as a white solid. MS m/z 600 (MH)+.

Step 2: To a rt solution of tert-butyl(S)-1-((2S,3S)-1-acetyl-5-((3-cyclopropylquinolin-4-yl)methyl)-2-methyl-4-oxo-2,3,4,5-tetrahydro-1H-benzo[b][1,4]diazepin-3-ylamino)-1-oxopropan-2-yl(methyl)carbamate (65 mg, 108 μmol) in CH2Cl2 (434 μl) was added TFA (108 μl). The reaction was stirred for 2.5 h, then concentrated and purified by reverse phase preparative HPLC to provide, after extraction from sat. aq. NaHCO3 and lyophilzation, (S)-N-((2S,3S)-1-acetyl-5-((3-cyclopropylquinolin-4-yl)methyl)-2-methyl-4-oxo-2,3,4,5-tetrahydro-1H-benzo[b][1,4]diazepin-3-yl)-2-(methylamino)propanamide (27.2 mg, 50%) as a white solid. MS m/z 500 (MH)+.

Example 19

(S)-N-((2S,3S)-1-Acetyl-5-((1-(2-cyanophenyl)-1H-indazol-3-yl)methyl)-2-methyl-4-oxo-2,3,4,5-tetrahydro-1H-benzo[b][1,4]diazepin-3-yl)-2-(methylamino)propanamide

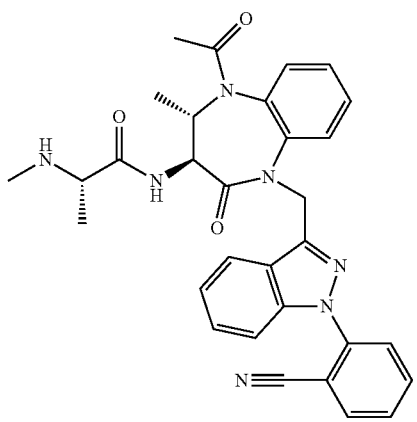 [SMILES: CN[C@@H](C)C(=O)N[C@@H]1C(=O)N(Cc2nn(-c3ccccc3C#N)c3ccccc23)c2ccccc2N(C(C)=O)[C@H]1C]

Step 1: To a rt solution of tert-butyl(S)-1-((2S,3S)-1-acetyl-2-methyl-4-oxo-2,3,4,5-tetrahydro-1H-benzo[b][1,4]diazepin-3-ylamino)-1-oxopropan-2-yl(methyl)carbamate (84.6 mg, 202 μmol) in DMF (505 μl) was added 2-(3-(bromomethyl)-1H-indazol-1-yl)benzonitrile (75.7 mg, 243 μmol), cesium carbonate (85.6 mg, 263 μmol), and sodium iodide (39.4 mg, 263 μmol). The reaction was stirred at rt for 16 h, then diluted with EtOAc, washed with H2O and sat. aq. NaCl, dried over Na2SO4, filtered, and concentrated. The crude material was purified by flash chromatography to provide tert-butyl(S)-1-((2S,3S)-1-acetyl-5-((1-(2-cyanophenyl)-1H-indazol-3-yl)methyl)-2-methyl-4-oxo-2,3,4,5-tetrahydro-1H-benzo[b][1,4]diazepin-3-ylamino)-1-oxopropan-2-yl(methyl)carbamate (79 mg, 60%) as a white solid. MS m/z 672 (MNa)+.

Step 2: To a rt solution of tert-butyl(S)-1-((2S,3S)-1-acetyl-5-((1-(2-cyanophenyl)-1H-indazol-3-yl)methyl)-2-methyl-4-oxo-2,3,4,5-tetrahydro-1H-benzo[b][1,4]diazepin-3-ylamino)-1-oxopropan-2-yl(methyl)carbamate (79 mg, 122 μmol) in CH2Cl2 (486 μl) was added TFA (122 μl). The reaction was stirred for 1.5 h, then concentrated and purified by reverse phase preparative HPLC to provide, after extraction from sat. aq. NaHCO3, (S)-N-((2S,3S)-1-acetyl-5-((1-(2-cyanophenyl)-1H-indazol-3-yl)methyl)-2-methyl-4-oxo-2,3,4,5-tetrahydro-1H-benzo[b][1,4]diazepin-3-yl)-2-(methylamino)propanamide (57.0 mg, 85%) as a white solid. MS m/z 550 (MH)+.

Example 20

(S)-N-((2S,3S)-1-Acetyl-2-methyl-5-((3-methylquinolin-4-yl)methyl)-4-oxo-2,3,4,5-tetrahydro-1H-benzo[b][1,4]diazepin-3-yl)-2-(methylamino)propanamide dihydrochloride

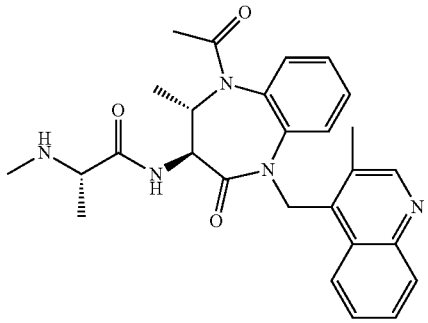 [SMILES: CN[C@@H](C)C(=O)N[C@@H]1C(=O)N(Cc2c(C)cnc3ccccc23)c2ccccc2N(C(C)=O)[C@H]1C]

Step 1: To a rt suspension of (3-methylquinolin-4-yl)methanol (67 mg, 387 μmol) in CH2Cl2 (3.87 ml) was added triethylamine (108 μl, 774 μmol), followed by methanesulfonyl chloride (36.0 μl, 464 μmol), dropwise. The reaction was stirred at rt for 1.5 h, then diluted with CH2Cl2, washed with H2O and sat. aq. NaCl, dried over Na2SO4, filtered, and concentrated. This material was taken up in DMF (582 μl) and tert-butyl(S)-1-((2S,3S)-1-acetyl-2-methyl-4-oxo-2,3,4,5-tetrahydro-1H-benzo[b][1,4]diazepin-3-ylamino)-1-oxopropan-2-yl(methyl)carbamate (97.5 mg, 233 μmol), cesium carbonate (98.7 mg, 303 μmol), and sodium iodide (45.4 mg, 303 μmol) were added. The reaction was stirred at rt for 18 h, then diluted with EtOAc, washed with H2O and sat. aq. NaCl, dried over Na2SO4, filtered, and concentrated. The crude material was purified by reverse phase preparative HPLC to provide, after extraction from sat. aq. NaHCO3, tert-butyl(S)-1-((2S,3S)-1-acetyl-2-methyl-5-((3-methylquinolin-4-yl)methyl)-4-oxo-2,3,4,5-tetrahydro-1H-benzo[b][1,4]diazepin-3-ylamino)-1-oxopropan-2-yl(methyl)carbamate (96.4 mg, 72%) as an off-white solid. MS m/z 574 (MH)+.

Step 2: A rt solution of tert-butyl(S)-1-((2S,3S)-1-acetyl-2-methyl-5-((3-methylquinolin-4-yl)methyl)-4-oxo-2,3,4,5-tetrahydro-1H-benzo[b][1,4]diazepin-3-ylamino)-1-oxopropan-2-yl(methyl)carbamate (96 mg, 167 µmol) in 4 M HCl in dioxane (837 µl) was stirred for 1.5 h. The reaction was diluted with Et2O and the solids were collected by vacuum filtration, taken up in MeCN—H2O, and lyophilized to provide (S)-N-((2S,3S)-1-acetyl-2-methyl-5-((3-methylquinolin-4-yl)methyl)-4-oxo-2,3,4,5-tetrahydro-1H-benzo[b][1,4]diazepin-3-yl)-2-(methylamino)propanamide dihydrochloride (72.2 mg, 79%) as an off-white solid. MS m/z 474 (MH)+.

Example 21

(S)-N-((2S,3S)-1-Acetyl-5-((2-methoxynaphthalen-1-yl)methyl)-2-methyl-4-oxo-2,3,4,5-tetrahydro-1H-benzo[b][1,4]diazepin-3-yl)-2-(methylamino)propanamide hydrochloride

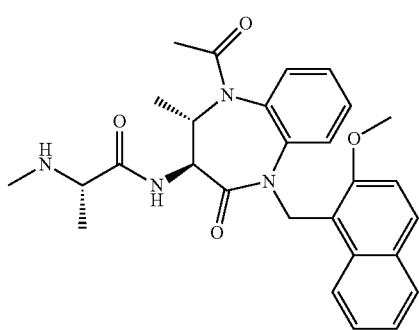 [SMILES: CN[C@@H](C)C(=O)N[C@@H]1C(=O)N(Cc2c(OC)ccc3ccccc23)c2ccccc2N(C(C)=O)[C@H]1C]

Step 1: To a rt solution of tert-butyl(S)-1-((2S,3S)-1-acetyl-2-methyl-4-oxo-2,3,4,5-tetrahydro-1H-benzo[b][1,4]diazepin-3-ylamino)-1-oxopropan-2-yl(methyl)carbamate (72 mg, 172 µmol) in DMF (430 µl) was added 1-(chloromethyl)-2-methoxynaphthalene (42.7 mg, 206 µmol), cesium carbonate (72.9 mg, 224 µmol), and sodium iodide (33.5 mg, 224 µmol). The reaction was stirred at rt for 16 h, then diluted with EtOAc, washed with H2O and sat. aq. NaCl, dried over Na2SO4, filtered, and concentrated. The crude material was purified by flash chromatography to provide tert-butyl(S)-1-((2S,3S)-1-acetyl-5-((2-methoxynaphthalen-1-yl)methyl)-2-methyl-4-oxo-2,3,4,5-tetrahydro-1H-benzo[b][1,4]diazepin-3-ylamino)-1-oxopropan-2-yl(methyl)carbamate (49.8 mg, 49%) as an off-white solid. MS m/z 611 (MNa)+.

Step 2: A rt suspension of tert-butyl(S)-1-((2S,3S)-1-acetyl-5-((2-methoxynaphthalen-1-yl)methyl)-2-methyl-4-oxo-2,3,4,5-tetrahydro-1H-benzo[b][1,4]diazepin-3-ylamino)-1-oxopropan-2-yl(methyl)carbamate (49.8 mg, 84.6 µmol) in 4 M HCl in dioxane (423 µl) was stirred for 2 h. The reaction was diluted with Et2O and the solids were collected by vacuum filtration, taken up in MeCN—H2O, and lyophilized to provide (S)-N-((2S,3S)-1-acetyl-5-((2-methoxynaphthalen-1-yl)methyl)-2-methyl-4-oxo-2,3,4,5-tetrahydro-1H-benzo[b][1,4]diazepin-3-yl)-2-(methylamino)propanamide hydrochloride (32.4 mg, 73%) as a white solid. MS m/z 489 (MH)+.

Example 22

(S)-N-((2S,3S)-1-Acetyl-2-methyl-5-((2-methylnaphthalen-1-yl)methyl)-4-oxo-2,3,4,5-tetrahydro-1H-benzo[b][1,4]diazepin-3-yl)-2-(methylamino)propanamide hydrochloride

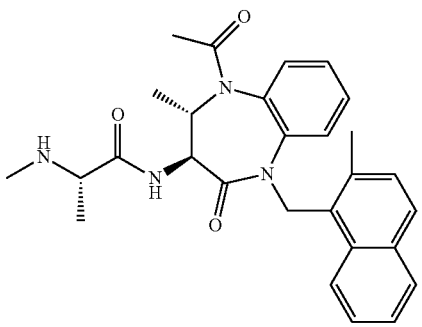 [SMILES: CN[C@@H](C)C(=O)N[C@@H]1C(=O)N(Cc2c(C)ccc3ccccc23)c2ccccc2N(C(C)=O)[C@H]1C]

Step 1: To a rt solution of tert-butyl(S)-1-((2S,3S)-1-acetyl-2-methyl-4-oxo-2,3,4,5-tetrahydro-1H-benzo[b][1,4]diazepin-3-ylamino)-1-oxopropan-2-yl(methyl)carbamate (72 mg, 172 µmol) in DMF (430 µl) was added 1-(chloromethyl)-2-methylnaphthalene (39.4 mg, 206 µmol), cesium carbonate (72.9 mg, 224 µmol), and sodium iodide (33.5 mg, 224 µmol). The reaction was stirred at rt for 16 h, then diluted with CH2Cl2, washed with H2O and sat. aq. NaCl, dried over Na2SO4, filtered, and concentrated. The crude material was purified by flash chromatography to provide tert-butyl(S)-1-((2S,3S)-1-acetyl-2-methyl-5-((2-methylnaphthalen-1-yl)methyl)-4-oxo-2,3,4,5-tetrahydro-1H-benzo[b][1,4]diazepin-3-ylamino)-1-oxopropan-2-yl(methyl)carbamate (73.1 mg, 74%) as an off-white solid. MS m/z 595 (MNa)+.

Step 2: A rt suspension of tert-butyl(S)-1-((2S,3S)-1-acetyl-2-methyl-5-((2-methylnaphthalen-1-yl)methyl)-4-oxo-2,3,4,5-tetrahydro-1H-benzo[b][1,4]diazepin-3-ylamino)-1-oxopropan-2-yl(methyl)carbamate (73.1 mg, 128 µmol) in 4 M HCl in dioxane (638 µl) was stirred for 2 h. The reaction was diluted with Et2O and the solids were collected by vacuum filtration, taken up in MeCN—H2O, and lyophilized to provide (S)-N-((2S,3S)-1-acetyl-2-methyl-5-((2-methylnaphthalen-1-yl)methyl)-4-oxo-2,3,4,5-tetrahydro-1H-benzo[b][1,4]diazepin-3-yl)-2-(methylamino)propanamide hydrochloride (54.3 mg, 84%) as a white solid. MS m/z 473 (MH)+.

Example 23

(S)-N-((3S,4S)-1-((3-Cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride

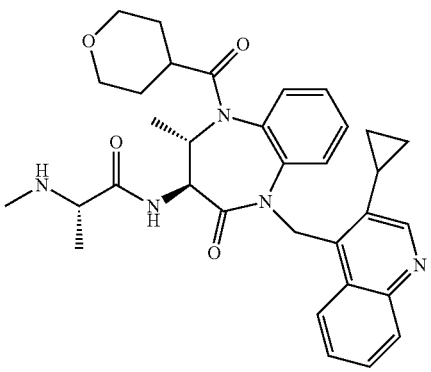 [SMILES: CN[C@@H](C)C(=O)N[C@@H]1C(=O)N(Cc2c(C3CC3)cnc3ccccc23)c2ccccc2N(C(=O)C2CCOCC2)[C@H]1C]

Step 1: To a rt solution of tert-butyl methyl((S)-1-((2S,3S)-2-methyl-4-oxo-1-(tetrahydro-2H-pyran-4-carbonyl)-2,3,4,5-tetrahydro-1H-benzo[b][1,4]diazepin-3-ylamino)-1-oxopropan-2-yl)carbamate (110 mg, 225 µmol) in DMF (563 µl) was added (3-cyclopropylquinolin-4-yl)methyl methanesulfonate (74.9 mg, 270 µmol), cesium carbonate (95.4 mg, 293 µmol), and sodium iodide (43.9 mg, 293 µmol). The reaction was stirred at rt for 2.5 days, then diluted with EtOAc, washed with H2O and sat. aq. NaCl, dried over Na2SO4, filtered, and concentrated. The crude material was purified by flash chromatography to provide tert-butyl(S)-1-((3S,4S)-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-ylamino)-1-oxopropan-2-yl(methyl)carbamate (78 mg, 52%) as an off-white solid. MS m/z 670 (MH)+.

Step 2: A rt solution of tert-butyl(S)-1-((3S,4S)-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (66.8 mg, 95%) as an off-white solid. MS m/z 570 (MH)+.

Example 24

(S)-N-((3S,4S)-1-((1-(2-Cyanophenyl)-1H-indazol-3-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride

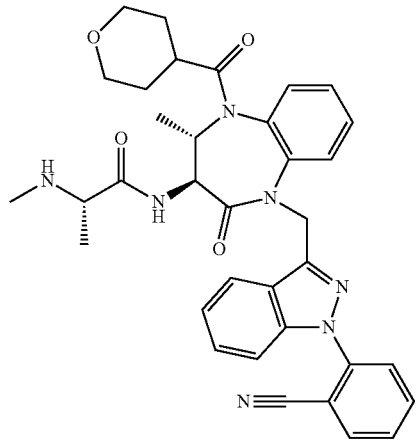 [SMILES: CN[C@@H](C)C(=O)N[C@@H]1C(=O)N(Cc2nn(-c3ccccc3C#N)c3ccccc23)c2ccccc2N(C(=O)C2CCOCC2)[C@H]1C]

Step 1: To a rt solution of tert-butyl methyl((S)-1-((2S,3S)-2-methyl-4-oxo-1-(tetrahydro-2H-pyran-4-carbonyl)-2,3,4,5-tetrahydro-1H-benzo[b][1,4]diazepin-3-ylamino)-1-oxopropan-2-yl)carbamate (111 mg, 227 µmol) in DMF (568 µl) was added 2-(3-(bromomethyl)-1H-indazol-1-yl)benzonitrile (85.1 mg, 273 µmol), cesium carbonate (96.2 mg, 295 µmol), and sodium iodide (44.3 mg, 295 µmol). The reaction was stirred at rt for 2.5 days, then diluted with EtOAc, washed with H2O and sat. aq. NaCl, dried over Na2SO4, filtered, and concentrated. The crude material was purified by flash chromatography to provide tert-butyl(S)-1-((3S,4S)-1-((1-(2-cyanophenyl)-1H-indazol-3-yl)methyl)-4-methyl-2-oxo-5-(tetrahydro-2H-pyran-4-carbonyl)-2,3,4,5-tetrahydro-1H-benzo[b][1,4]diazepin-3-ylamino)-1-oxopropan-2-yl(methyl)carbamate (128 mg, 78%) as an off-white solid. MS m/z 742 (MNa)+.

Step 2: A rt solution of tert-butyl(S)-1-((3S,4S)-1-((1-(2-cyanophenyl)-1H-indazol-3-yl)methyl)-4-methyl-2-oxo-5-(tetrahydro-2H-pyran-4-carbonyl)-2,3,4,5-tetrahydro-1H-benzo[b][1,4]diazepin-3-ylamino)-1-oxopropan-2-yl(methyl)carbamate (128 mg, 178 µmol) in 4 M HCl in dioxane (889 µl) was stirred for 2 h. The reaction was diluted with Et2O and the solids were collected by vacuum filtration, taken up in MeCN—H2O, and lyophilized to provide (S)-N-((3S,4S)-1-((1-(2-cyanophenyl)-1H-indazol-3-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (94.1 mg, 81%) as an off-white solid. MS m/z 620 (MH)+.

Example 25

(S)-N-((2S,3S)-5-((5-Bromo-2-methoxynaphthalen-1-yl)methyl)-7-cyano-2-methyl-1-(2-(methylsulfonyl)acetyl)-4-oxo-2,3,4,5-tetrahydro-1H-benzo[b][1,4]diazepin-3-yl)-2-(methylamino)propanamide 2,2,2-trifluoroacetate

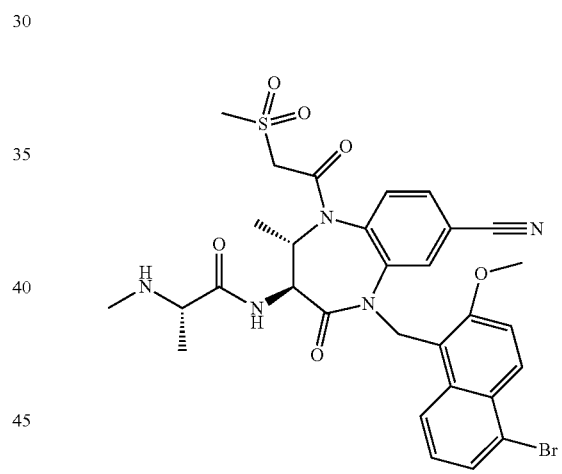

Step 1: To a 0° C. solution of tert-butyl(2S,3S)-2-methyl-4-oxo-2,3,4,5-tetrahydro-1H-benzo[b][1,4]diazepin-3-ylcarbamate (107.0 mg, 367 µmol) in DMF (2.45 ml) was added a solution of N-bromosuccinimide (68.6 mg, 386 µmol) in DMF (1.22 ml), dropwise over 5 min. The reaction was stirred at 0° C. for 30 min, then diluted with sat. aq. NH4Cl and extracted with EtOAc. The combined organic layers were washed with H2O, sat. aq. NaHCO3, and sat. aq. NaCl, dried over Na2SO4, and concentrated. The crude material was purified by flash chromatography to provide tert-butyl(2S,3S)-7-bromo-2-methyl-4-oxo-2,3,4,5-tetrahydro-1H-benzo[b][1,4]diazepin-3-ylcarbamate (130 mg, 96%) as a white solid. MS m/z 392/394 (MNa)+.

Step 2: To a 0° C. solution of tert-butyl(2S,3S)-7-bromo-2-methyl-4-oxo-2,3,4,5-tetrahydro-1H-benzo[b][1,4]diazepin-3-ylcarbamate (130 mg, 351 µmol) and 2-(methylsulfonyl)acetic acid (53.4 mg, 386 µmol) in pyridine (3.51 ml) was added phosphoryl chloride (64.3 µl, 702 µmol). The reaction was stirred at 0° C. for 30 min, then quenched by the addition of H2O and extracted with EtOAc. The combined organic layers were washed with 1 N aq. citric acid, H2O, sat. aq. NaHCO3, and sat. aq. NaCl, dried over Na2SO4, filtered, and concentrated. The crude material was purified by flash chromatography to provide tert-butyl(2S,3S)-7-bromo-2-methyl-1-(2-(methylsulfonyl)acetyl)-4-oxo-2,3,4,5-tetrahydro-1H-benzo[b][1,4]diazepin-3-ylcarbamate (161 mg, 94%) as a white solid. MS m/z 512/514 (MNa)+.

Step 3: A solution of tert-butyl(2S,3S)-7-bromo-2-methyl-1-(2-(methylsulfonyl)acetyl)-4-oxo-2,3,4,5-tetrahydro-1H-benzo[b][1,4]diazepin-3-ylcarbamate (124 mg, 253 μmol) in DMF (2.53 ml) was sparged with Ar for 10 min, then zinc cyanide (59.4 mg, 506 μmol) and tetrakis(triphenyl-phosphine)palladium(0) (29.2 mg, 25.3 μmol) were added. The mixture was sparged with Ar for an additional 5 min, then sealed and heated in the microwave at 110° C. for 20 min, then diluted with H2O and extracted with EtOAc. The combined organic layers were washed with H2O and sat. aq. NaCl, dried over Na2SO4, filtered, and concentrated. The crude material was purified by flash chromatography to provide tert-butyl (2S,3S)-7-cyano-2-methyl-1-(2-(methylsulfonyl)acetyl)-4-oxo-2,3,4,5-tetrahydro-1H-benzo[b][1,4]diazepin-3-ylcarbamate (104 mg, 94%) as a white solid. MS m/z 459 (MNa)+.

Step 4: To a rt solution of tert-butyl(2S,3S)-7-cyano-2-methyl-1-(2-(methylsulfonyl)acetyl)-4-oxo-2,3,4,5-tetrahydro-1H-benzo[b][1,4]diazepin-3-ylcarbamate (138 mg, 316 μmol) in CH2Cl2 (1.26 ml) was added TFA (316 μl). The reaction was stirred at rt for 2 h, then concentrated. This material was taken up in DMF (1.05 ml) and N,N-diisopropylethylamine (219 μl, 1.26 mmol), Boc-N-methyl-L-alanine (70.6 mg, 348 μmol), and HBTU (132 mg, 348 μmol) were added. The reaction was stirred at rt for 30 min, then diluted with EtOAc, washed with H2O, sat. aq. NaHCO3, and sat. aq. NaCl, dried over Na2SO4, filtered, and concentrated. The crude material was purified by flash chromatography to provide tert-butyl(S)-1-((2S,3S)-7-cyano-2-methyl-1-(2-(methylsulfonyl)acetyl)-4-oxo-2,3,4,5-tetrahydro-1H-benzo[b][1,4]diazepin-3-ylamino)-1-oxopropan-2-yl)methyl)carbamate (123 mg, 75%) as a white solid. MS m/z 543 (MNa)+.

Step 5: To a rt solution of tert-butyl(S)-1-((2S,3S)-7-cyano-2-methyl-1-(2-(methylsulfonyl)acetyl)-4-oxo-2,3,4,5-tetrahydro-1H-benzo[b][1,4]diazepin-3-ylamino)-1-oxopropan-2-yl(methyl)carbamate (122 mg, 234 μmol) in DMF (585 μl) was added 5-bromo-1-(chloromethyl)-2-methoxynaphthalene (80.2 mg, 281 μmol), cesium carbonate (99.1 mg, 304 μmol), and sodium iodide (45.6 mg, 304 μmol). The reaction was stirred at rt for 1.5 h, then diluted with EtOAc, washed with H2O and sat. aq. NaCl, dried over Na2SO4, filtered, and concentrated. The crude material was purified by flash chromatography to provide tert-butyl(S)-1-((2S,3S)-5-((5-bromo-2-methoxynaphthalen-1-yl)methyl)-7-cyano-2-methyl-1-(2-(methylsulfonyl)acetyl)-4-oxo-2,3,4,5-tetrahydro-1H-benzo[b][1,4]diazepin-3-ylamino)-1-oxopropan-2-yl(methyl)carbamate (70 mg, 39% yield) as a white solid. MS m/z 792/794 (MNa)+.

Step 6: To a rt solution of tert-butyl(S)-1-((2S,3S)-5-((5-bromo-2-methoxynaphthalen-1-yl)methyl)-7-cyano-2-methyl-1-(2-(methylsulfonyl)acetyl)-4-oxo-2,3,4,5-tetrahydro-1H-benzo[b][1,4]diazepin-3-ylamino)-1-oxopropan-2-yl (methyl)carbamate (68 mg, 88.2 μmol) in CH2Cl2 (353 μl) was added TFA (88.2 μl). The reaction was stirred at rt for 2.5 h, then concentrated, taken up in H2O, and lyophilized to provide (S)-N-((2S,3S)-5-((5-bromo-2-methoxynaphthalen-1-yl)methyl)-7-cyano-2-methyl-1-(2-(methylsulfonyl) acetyl)-4-oxo-2,3,4,5-tetrahydro-1H-benzo[b][1,4]diazepin-3-yl)-2-(methylamino)propanamide 2,2,2-trifluoroacetate (68.6 mg, 99%) as a white solid. MS m/z 670/672 (MH)+.

Intermediate 1 tert-Butyl(3S,4S)-7-cyano-4-methyl-2-oxo-2,3,4,5-tetrahydro-1H-benzo[b][1,4]diazepin-3-ylcarbamate

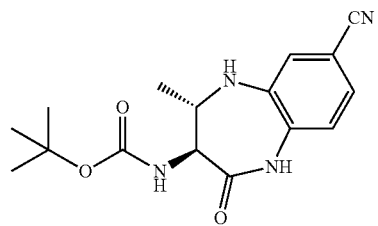 [SMILES: C[C@@H]1Nc2cc(C#N)ccc2NC(=O)[C@H]1NC(=O)OC(C)(C)C]

Step 1: To a stirred solution of L-threonine benzyl ester oxalate (5 g, 16.7 mmol) and sodium bicarbonate (4.21 g, 50.1 mmol) in H2O (35 ml), methanol (35 ml) and di-tert-butyl dicarbonate (5.1 g, 23.4 mmol) were added. The mixture was stirred overnight, then concentrated, acidified to pH ~5 with 0.5 N HCl, and extracted with EtOAc. The organic layer was washed with brine, dried over Na2SO4, concentrated, and purified by column chromatography to provide (2S,3R)-benzyl 2-(tert-butoxycarbonylamino)-3-hydroxybutanoate (4.6 g, 89%).

Step 2: A solution of SOCl2 (24.2 ml, 332 mmol) in dry MeCN (240 ml) under nitrogen was cooled to −5° C., then (2S,3R)-benzyl 2-(tert-butoxycarbonylamino)-3-hydroxybutanoate (50 g, 162 mmol) in dry MeCN (120 ml) was added dropwise over 10 min, followed by dropwise addition of pyridine (65.4 ml, 808 mmol) to maintain the internal temp <0° C. After stirring for 10 min, cooling was removed and the reaction mixture was stirred for 3 h, then concentrated, mixed with EtOAc (1130 ml) and H2O (320 ml), and stirred at RT for 20 min. The aqueous layer was extracted with EtOAc and the combined organic layers were washed with brine 3 times, then concentrated. The residue was dissolved in CH3CN (320 ml), and, at 5° C., ruthenium(III) chloride (77.1 mg, 372 μmol) was added, followed by sodium periodate (68.8 g, 321 mmol). After stirring for 10 min, H2O (320 ml) was added over about 1 min. The mixture was stirred at RT for 1.5 h, then filtered to remove solid salts, treated with brine (320 ml), and extracted with EtOAc twice. The organic layer was washed with brine, dried over Na2SO4, filtered through a bed of 3 layers of celite+silica gel+Na2SO4, and concentrated to afford 4-benzyl 3-tert-butyl(4S,5R)-5-methyl-1,2,3-oxathiazolidine-3,4-dicarboxylate 2,2-dioxide (50.1 g, 84%) as a slightly brownish oil.

Step 3: To a solution of 4-benzyl 3-tert-butyl(4S,5R)-5-methyl-1,2,3-oxathiazolidine-3,4-dicarboxylate 2,2-dioxide (17.13 g, 46.1 mmol) in DMF (171 ml) at −40° C. was added sodium azide (3.9 g, 60.0 mmol) in portions, and the mixture was stirred at −40° C. then slowly warmed to rt over 4 h. Added 20% aq. NaCl (100 ml), followed by dropwise addition of 2 N H2SO4 (10 ml). The reaction was stirred at rt for 3 h, then partitioned between H2O and EtOAc, and the aqueous layer was extracted with EtOAc. The combined organic layers were washed with H2O and brine, dried over Na2SO4, filtered, and concentrated to afford (2S,3S)-benzyl 3-azido-2-(tert-butoxycarbonylamino)butanoate as a slightly yellowish glue (14.8 g, 96%).

Step 4: A solution of (2S,3S)-benzyl 3-azido-2-(tert-butoxycarbonylamino)butanoate (1.7 g, 5.08 mmol) and PdC (5%, wet) (340 mg, 319 μmol) in MeOH (16.4 g, 20.7 ml) was shaken under H2 (50 PSI) for 3.5 h, then filtered through a bed of celite and concentrated to give (2S,3S)-3-amino-2-(tert-butoxycarbonylamino)butanoic acid (1.15 g, quant.) as a white solid.

Step 5: A mixture of (2S,3S)-3-amino-2-(tert-butoxycarbonylamino)butanoic acid (3.14 g, 14.4 mmol), dimethylsulfoxide (40 ml), 3-fluoro-4-nitrobenzonitrile (2.63 g, 15.8 mmol), and sodium bicarbonate (4.83 g, 57.5 mmol) was stirred at 55° C. for 3 h. Additional NaHCO3 (0.9 g) was added and the mixture was stirred at 60° C. for 1 hour, then cooled to RT, diluted with cold sat. Na2CO3, and washed with MTBE. The aqueous phase was carefully acidified to pH ~4 with solid citric acid and extracted with EtOAc (three times). The combined organic layers were washed with H2O twice and brine, dried over Na2SO4, filtered, and concentrated to provide (2S,3S)-2-(tert-butoxycarbonylamino)-3-(5-cyano-2-nitrophenylamino)butanoic acid (5.7 g, quant.).

Step 6: A mixture of (2S,3S)-2-(tert-butoxycarbonyl amino)-3-(5-cyano-2-nitrophenylamino)butanoic acid (5.35 g, 14.7 mmol) and PdC (10% dry basis, wet, 50% water) (535 mg, 251 μmol) in MeOH (60 ml) and EtOAc (60 ml) was shaken under H2 (50 PSI) for 4 h, then filtered through a bed of celite and concentrated to afford (2S,3S)-3-(2-amino-5-cyanophenylamino)-2-(tert-butoxycarbonylamino)butanoic acid (4.9 g, quant.) as a dark brown solid.

Step 7: A mixture of (2S,3S)-3-(2-amino-5-cyanophenylamino)-2-(tert-butoxycarbonylamino)butanoic acid (4.9 g, 14.7 mmol) in acetonitrile (96 ml), was cooled in an ice water bath, then 1-methylimidazole (3.5 ml, 44.0 mmol) was added and the reaction was stirred at 0° C. for 20 min, then methanesulfonyl chloride (1.31 ml, 16.9 mmol) was added dropwise. The cooling bath was removed and the reaction was stirred at RT for 2 h, then concentrated to 1⁄3 volume and treated with water (~200 ml, dropwise addition). The resulting solid was separated by filtration, washed with H2O, and dried under vacuum at 50° C. for 3 h to afford tert-butyl(3S,4S)-7-cyano-4-methyl-2-oxo-2,3,4,5-tetrahydro-1H-benzo[b][1,4]diazepin-3-ylcarbamate (4.2 g). The aqueous solution was extracted with EtOAc, dried over Na2SO4, and purified by flash chromatography (0-60% EtOAc in DCM) to afford additional product (0.4 g). MS m/z 339 (MNa)+.

Intermediate 2 tert-Butyl(S)-1-((2S,3S)-8-cyano-2-methyl-1-(2-(methylsulfonyl)acetyl)-4-oxo-2,3,4,5-tetrahydro-1H-benzo[b][1,4]diazepin-3-ylamino)-1-oxopropan-2-yl(methyl)carbamate

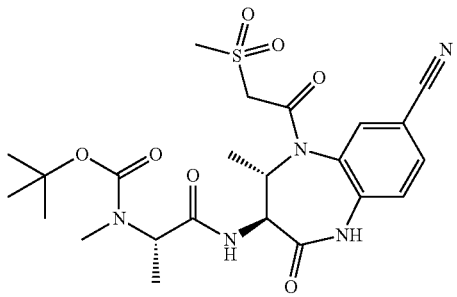 [SMILES: C[C@@H](C(=O)N[C@@H]1C(=O)Nc2ccc(C#N)cc2N(C(=O)CS(C)(=O)=O)[C@H]1C)N(C)C(=O)OC(C)(C)C]

Step 1: To a 0° C. solution of tert-butyl(3S,4S)-7-cyano-4-methyl-2-oxo-2,3,4,5-tetrahydro-1H-benzo[b][1,4]diazepin-3-ylcarbamate (106 mg, 335 μmol) in pyridine (3.35 ml) was added 2-(methylsulfonyl)acetic acid (50.9 mg, 369 μmol) followed by phosphoryl chloride (61.3 μl, 670 μmol), dropwise. The reaction was stirred at 0° C. for 30 min, then quenched by the addition of H2O and extracted with EtOAc. The combined organic layers were washed with 1 N aq. citric acid, H2O, sat. aq. NaHCO3, and sat. aq. NaCl, dried over Na2SO4, filtered, and concentrated. The crude material was purified by flash chromatography to provide tert-butyl(2S, 3S)-8-cyano-2-methyl-1-(2-(methylsulfonyl)acetyl)-4-oxo-2,3,4,5-tetrahydro-1H-benzo[b][1,4]diazepin-3-ylcarbamate (137 mg, 94%) as a white solid. MS m/z 459 (MNa)+.

Step 2: A rt solution of tert-butyl(2S,3S)-8-cyano-2-methyl-1-(2-(methylsulfonyl)acetyl)-4-oxo-2,3,4,5-tetrahydro-1H-benzo[b][1,4]diazepin-3-ylcarbamate (137 mg, 314 μmol) in 4 M HCl in dioxane (1.57 ml) was stirred for 2 h. The reaction was concentrated, taken up in in DMF (1.05 ml), and Boc-N-methyl-L-alanine (70.2 mg, 345 μmol), N,N-diisopropylethylamine (217 μl, 1.26 mmol), and HBTU (131 mg, 345 μmol) were added at 0° C. The reaction was stirred at rt for 30 min, then diluted with EtOAc, washed with H2O, sat. aq. NaHCO3, and sat. aq. NaCl, dried over Na2SO4, filtered, and concentrated. The crude material was purified by flash chromatography to provide tert-butyl(S)-1-((2S,3S)-8-cyano-2-methyl-1-(2-(methylsulfonyl)acetyl)-4-oxo-2,3,4,5-tetrahydro-1H-benzo[b][1,4]diazepin-3-ylamino)-1-oxopropan-2-yl(methyl)carbamate (121.8 mg, 74%) as a white solid. MS m/z 544 (MNa)+.

Intermediate 3

(3S,4S)-3-Amino-4-methyl-1-((2-methylnaphthalen-1-yl)methyl)-5-(2-(methylsulfonyl)acetyl)-2-oxo-2,3,4,5-tetrahydro-1H-benzo[b][1,4]diazepine-7-carbonitrile hydrochloride

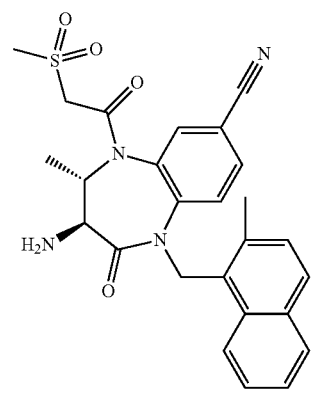 [SMILES: Cc1ccc2ccccc2c1CN1C(=O)[C@@H](N)[C@H](C)N(C(=O)CS(C)(=O)=O)c2cc(C#N)ccc21]

Step 1: To a rt solution of tert-butyl(2S,3S)-8-cyano-2-methyl-1-(2-(methylsulfonyl)acetyl)-4-oxo-2,3,4,5-tetrahydro-1H-benzo[b][1,4]diazepin-3-ylcarbamate (592 mg, 1.36 mmol) in DMF (3.39 ml) was added 1-(chloromethyl)-2-methylnaphthalene (284 mg, 1.49 mmol), cesium carbonate (530 mg, 1.63 mmol), and sodium iodide (244 mg, 1.63 mmol). The reaction was stirred at rt for 2 h, then diluted with EtOAc, washed with H2O and sat. aq. NaCl, dried over Na2SO4, filtered, and concentrated. The crude material was purified by flash chromatography then reverse phase preparative HPLC to provide, after extraction from sat. aq. NaHCO3, tert-butyl(3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-ylcarbamate (510 mg, 64%) as a white solid. MS m/z 613 (MNa)+.

Step 2: A rt solution of tert-butyl(3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-ylcarbamate (510 mg, 863 μmol) in 4 M HCl in dioxane (4.32 ml) was stirred for 2 h. The reaction was diluted with Et2O and the solids were collected by vacuum filtration to provide (3S,4S)-3-amino-4-methyl-1-((2-methylnaphthalen-1-yl)methyl)-5-(2-(methylsulfonyl)acetyl)-2-oxo-2,3,4,5-tetrahydro-1H-benzo[b][1,4]diazepine-7-carbonitrile hydrochloride (410 mg, 90%) as a white solid. MS m/z 491 (MH)+.

Intermediate 4 tert-Butyl(S)-1-((2S,3S)-1-acetyl-8-cyano-2-methyl-4-oxo-2,3,4,5-tetrahydro-1H-benzo[b][1,4]diazepin-3-ylamino)-1-oxopropan-2-yl(methyl)carbamate

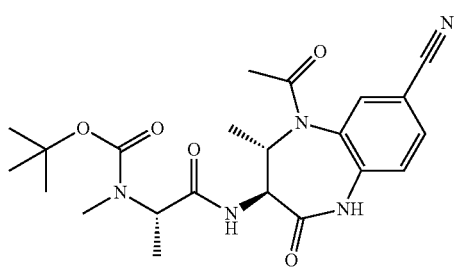 [SMILES: CC(=O)N1c2cc(C#N)ccc2NC(=O)[C@@H](NC(=O)[C@H](C)N(C)C(=O)OC(C)(C)C)[C@@H]1C]

Step 1: To a 0° C. suspension of tert-butyl(3S,4S)-7-cyano-4-methyl-2-oxo-2,3,4,5-tetrahydro-1H-benzo[b][1,4]diazepin-3-ylcarbamate (444 mg, 1.4 mmol) in CH2Cl2 (14.0 ml) was added pyridine (1.14 ml, 14.0 mmol), followed by acetyl chloride (120 μl, 1.68 mmol), dropwise. The reaction was stirred at 0° C. for 1 h, then allowed to warm to rt and stirred for 17 h. Additional acetyl chloride (120 μl, 1.68 mmol) was added and the reaction was stirred for 6 h, then quenched by the addition of H2O and extracted with CH2Cl2. The combined organic layers were washed with sat. aq. NaHCO3 and sat. aq. NaCl, dried over Na2SO4, filtered, and concentrated. The crude material was purified by flash chromatography to provide tert-butyl(3S,4S)-1,5-diacetyl-7-cyano-4-methyl-2-oxo-2,3,4,5-tetrahydro-1H-benzo[b][1,4]diazepin-3-ylcarbamate (460 mg, 82%) as a white foam. MS m/z 423 (MNa)+.

Step 2: To a rt solution of tert-butyl(3S,4S)-1,5-diacetyl-7-cyano-4-methyl-2-oxo-2,3,4,5-tetrahydro-1H-benzo[b][1,4]diazepin-3-ylcarbamate (413 mg, 1.03 mmol) in MeOH (10.3 ml) was added 1 M aq. sodium hydroxide (1.13 ml, 1.13 mmol), dropwise. The reaction was stirred for 30 min, then diluted with EtOAc, washed with H2O and sat. aq. NaCl, dried over Na2SO4, filtered, and concentrated. The crude material was purified by flash chromatography to provide tert-butyl(2S,3S)-1-acetyl-8-cyano-2-methyl-4-oxo-2,3,4,5-tetrahydro-1H-benzo[b][1,4]diazepin-3-ylcarbamate (144 mg, 39%) as a white solid. MS m/z 381 (MNa)+.

Step 3: A rt solution of tert-butyl(2S,3S)-1-acetyl-8-cyano-2-methyl-4-oxo-2,3,4,5-tetrahydro-1H-benzo[b][1,4]diazepin-3-ylcarbamate (144 mg, 402 μmol) in 4 M HCl in dioxane (2.01 ml) was stirred for 2 h. The reaction was diluted with Et2O and the solids were collected by vacuum filtration, taken up in DMF (1.34 ml), and Boc-N-methyl-L-alanine (89.9 mg, 442 μmol), N,N-diisopropylethylamine (278 μl, 1.61 mmol), and HBTU (168 mg, 442 μmol) were added at 0° C. The reaction was stirred at rt for 30 min, then diluted with EtOAc, washed with H2O, sat. aq. NaHCO3, and sat. aq. NaCl, dried over Na2SO4, filtered, and concentrated. The crude material was purified by flash chromatography to provide tert-butyl(S)-1-((2S,3S)-1-acetyl-8-cyano-2-methyl-4-oxo-2,3,4,5-tetrahydro-1H-benzo[b][1,4]diazepin-3-ylamino)-1-oxopropan-2-yl(methyl)carbamate (123 mg, 69%) as a white solid. MS m/z 466 (MNa)+.

Intermediate 5 tert-Butyl(S)-1-((2S,3S)-8-cyano-2-methyl-4-oxo-1-(tetrahydro-2H-pyran-4-carbonyl)-2,3,4,5-tetrahydro-1H-benzo[b][1,4]diazepin-3-ylamino)-1-oxopropan-2-yl(methyl)carbamate

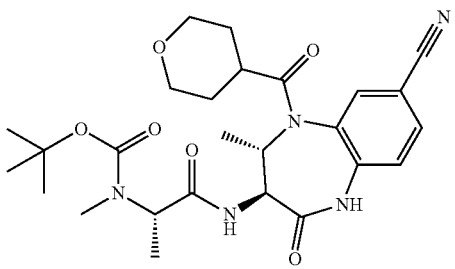 [SMILES: C[C@@H](C(=O)N[C@@H]1C(=O)Nc2ccc(C#N)cc2N(C(=O)C2CCOCC2)[C@H]1C)N(C)C(=O)OC(C)(C)C]

Step 1: To a 0° C. solution of tert-butyl(3S,4S)-7-cyano-4-methyl-2-oxo-2,3,4,5-tetrahydro-1H-benzo[b][1,4]diazepin-3-ylcarbamate (0.947 g, 2.99 mmol) in CH2Cl2 (29.9 ml) was added pyridine (1.46 ml, 18.0 mmol), followed by tetrahydro-2H-pyran-4-carbonyl chloride (979 mg, 6.59 mmol), dropwise. The reaction was stirred at 0° C., then allowed to warm to rt and stirred for 15 h, then quenched by the addition of H2O and extracted with CH2Cl2. The combined organic layers were washed with H2O, sat. aq. NaHCO3, and sat. aq. NaCl, dried over Na2SO4, filtered, and concentrated. The crude material was purified by flash chromatography to provide tert-butyl(3S,4S)-7-cyano-4-methyl-2-oxo-1,5-bis(tetrahydro-2H-pyran-4-carbonyl)-2,3,4,5-tetrahydro-1H-benzo[b][1,4]diazepin-3-ylcarbamate (0.707 g, 44%). MS m/z 563 (MNa)+.

Step 2: To a rt solution of tert-butyl(3S,4S)-7-cyano-4-methyl-2-oxo-1,5-bis(tetrahydro-2H-pyran-4-carbonyl)-2,3,4,5-tetrahydro-1H-benzo[b][1,4]diazepin-3-ylcarbamate (0.707 g, 1.31 mmol) in MeOH (13.1 ml) was added 1 M aq. sodium hydroxide (1.44 ml, 1.44 mmol), dropwise. The reaction was stirred for 30 min, then diluted with EtOAc, washed with H2O and sat. aq. NaCl, dried over Na2SO4, filtered, and concentrated. The crude material was purified by flash chromatography to provide tert-butyl(2S,3S)-8-cyano-2-methyl-4-oxo-1-(tetrahydro-2H-pyran-4-carbonyl)-2,3,4,5-tetrahydro-1H-benzo[b][1,4]diazepin-3-ylcarbamate (289 mg, 52%) as a white solid. MS m/z 451 (MNa)+.

Step 3: A rt solution of tert-butyl(2S,3S)-8-cyano-2-methyl-4-oxo-1-(tetrahydro-2H-pyran-4-carbonyl)-2,3,4,5-tetrahydro-1H-benzo[b][1,4]diazepin-3-ylcarbamate (289 mg, 674 μmol) in 4 M HCl in dioxane (3.37 ml) was stirred for 1 h. The reaction was diluted with Et2O and the solids were collected by vacuum filtration to provide (3S,4S)-3-amino-4-methyl-2-oxo-5-(tetrahydro-2H-pyran-4-carbonyl)-2,3,4,5- tetrahydro-1H-benzo[b][1,4]diazepine-7-carbonitrile hydrochloride (218 mg, 89%) as a white solid.

Step 4: To a 0° C. solution of (3S,4S)-3-amino-4-methyl-2-oxo-5-(tetrahydro-2H-pyran-4-carbonyl)-2,3,4,5-tetrahydro-1H-benzo[b][1,4]diazepine-7-carbonitrile hydrochloride (218 mg, 598 µmol) in DMF (1.99 ml) was added Boc-N-methyl-L-alanine (134 mg, 657 µmol), N,N-diisopropylethylamine (414 µl, 2.39 mmol), and HBTU (249 mg, 657 µmol). The reaction was stirred at rt for 30 min, then diluted with EtOAc, washed with H2O, sat. aq. NaHCO3, and sat. aq. NaCl, dried over Na2SO4, filtered, and concentrated. The crude material was purified by flash chromatography to provide tert-butyl(S)-1-((2S,3S)-8-cyano-2-methyl-4-oxo-1-(tetrahydro-2H-pyran-4-carbonyl)-2,3,4,5-tetrahydro-1H-benzo[b][1,4]diazepin-3-ylamino)-1-oxopropan-2-yl(methyl)carbamate (239 mg, 78%) as a white solid. MS m/z 536 (MNa)+.

Example 26

(S)-N-((3S,4S)-1-((5-Bromo-2-methoxynaphthalen-1-yl)methyl)-7-cyano-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate

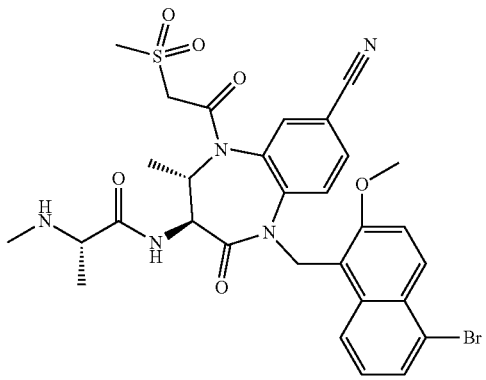 [SMILES: CN[C@@H](C)C(=O)N[C@@H]1C(=O)N(Cc2c(OC)ccc3c(Br)cccc23)c2ccc(C#N)cc2N(C(=O)CS(C)(=O)=O)[C@H]1C]

Step 1: To a rt solution of tert-butyl(S)-1-((2S,3S)-8-cyano-2-methyl-1-(2-(methylsulfonyl)acetyl)-4-oxo-2,3,4,5-tetrahydro-1H-benzo[b][1,4]diazepin-3-ylamino)-1-oxopropan-2-yl(methyl)carbamate (29.5 mg, 56.6 µmol) in DMF (141 µl) was added 5-bromo-1-(chloromethyl)-2-methoxynaphthalene (17.8 mg, 62.2 µmol), cesium carbonate (22.1 mg, 67.9 µmol), and sodium iodide (10.2 mg, 67.9 µmol). The reaction was stirred at rt for 2.5 h, then diluted with EtOAc, washed with H2O and sat. aq. NaCl, dried over Na2SO4, filtered, and concentrated. The crude material was purified by flash chromatography to provide tert-butyl(S)-1-((3S,4S)-1-((5-bromo-2-methoxynaphthalen-1-yl)methyl)-7-cyano-4-methyl-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (33 mg, 76%) as a white solid. MS m/z 792/794 (MNa)+.

Step 2: To a rt solution of tert-butyl(S)-1-((3S,4S)-1-((5-bromo-2-methoxynaphthalen-1-yl)methyl)-7-cyano-4-methyl-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (32 mg, 41.5 µmol) in CH2Cl2 (166 µl) was added TFA (41.5 µl). The reaction was stirred at rt for 6 h, then concentrated, taken up in H2O, and lyophilized to provide (S)-N-((3S,4S)-1-((5-bromo-2-methoxynaphthalen-1-yl)methyl)-7-cyano-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate (30.3 mg, 93%) as a white solid. MS m/z 670/672 (MNa)+.

Example 27

(S)-N-((3S,4S)-7-Cyano-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride

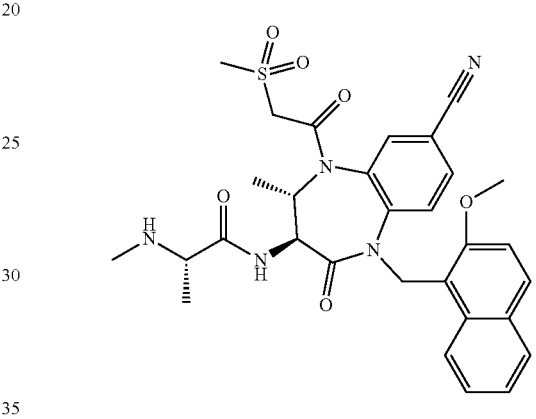

Step 1: To a rt solution of tert-butyl(S)-1-((2S,3S)-8-cyano-2-methyl-1-(2-(methylsulfonyl)acetyl)-4-oxo-2,3,4,5-tetrahydro-1H-benzo[b][1,4]diazepin-3-ylamino)-1-oxopropan-2-yl(methyl)carbamate (108 mg, 207 µmol) in DMF (518 µl) was added 1-(chloromethyl)-2-methoxynaphthalene (47.1 mg, 228 µmol), cesium carbonate (81.0 mg, 248 µmol), and sodium iodide (37.2 mg, 248 µmol). The reaction was stirred at rt for 1.5 h, then diluted with EtOAc, washed with H2O and sat. aq. NaCl, dried over Na2SO4, filtered, and concentrated. The crude material was purified by flash chromatography then reverse phase preparative HPLC to provide tert-butyl(S)-1-((3S,4S)-7-cyano-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (55 mg, 38%) as a white solid. MS m/z 714 (MNa)+.

Step 2: A rt solution of tert-butyl(S)-1-((3S,4S)-7-cyano-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (55 mg, 79.5 µmol) in 4 M HCl in dioxane (398 µl) was stirred for 1 h. The reaction was diluted with Et2O and the solids were collected by vacuum filtration, taken up in MeCN—H2O, and lyophilized to provide (S)-N-((3S,4S)-7-cyano-1-((2-methoxynaphthalen-1-yl)methyl)-4-methyl-5-(2-(methylsulfonyl)acetyl)-2-oxo-2,3,4,5-tetrahydro-1H- benzo[b][1,4]diazepin-3-yl)-2-(methylamino)propanamide hydrochloride (41.6 mg, 83%) as a white solid. MS m/z 592 (MH)+.

Example 28

(S)-N-((3S,4S)-7-Cyano-4-methyl-1-((2-methyl-naphthalen-1-yl)methyl)-5-(2-(methylsulfonyl)acetyl)-2-oxo-2,3,4,5-tetrahydro-1H-benzo[b][1,4]diazepin-3-yl)-2-(ethyl amino)propanamide hydrochloride

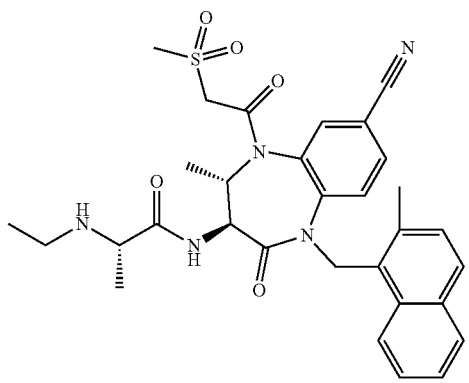 [SMILES: CCN[C@@H](C)C(=O)N[C@@H]1C(=O)N(Cc2c(C)ccc3ccccc23)c2ccc(C#N)cc2N(C(=O)CS(C)(=O)=O)[C@H]1C]

Step 1: To a solution of (S)-2-(tert-butoxycarbonylamino)propanoic acid (0.7 g, 3.7 mmol) and ethyl iodide (2.6 ml, 32.2 mmol) in THF (10 ml) was added sodium hydride (60% w/w dispersion in mineral oil, 576 mg, 14.4 mmol). The reaction was sealed and stirred at 60° C. overnight, then partitioned between EtOAc and H2O. The aqueous layer was acidified to pH 4 with citric acid solution and extracted with EtOAc. The organic layer was dried over MgSO4, filtered and concentrated to provide (S)-2-(tert-butoxycarbonyl(ethyl)amino)propanoic acid (700 mg, 87%) as an oil.

Step 2: To a rt solution of (3S,4S)-3-amino-4-methyl-1-((2-methylnaphthalen-1-yl)methyl)-5-(2-(methylsulfonyl)acetyl)-2-oxo-2,3,4,5-tetrahydro-1H-benzo[b][1,4]diazepine-7-carbonitrile hydrochloride (100 mg, 190 μmol) in DMF (632 μl) was added (S)-2-(tert-butoxycarbonyl(ethyl)amino)propanoic acid (45.3 mg, 209 μmol), N,N-diisopropylethylamine (131 μl, 759 μmol), and HBTU (79.2 mg, 209 μmol). The reaction was stirred at rt for 30 min, then purified by reverse phase preparative HPLC to provide tert-butyl(S)-1-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-ylamino)-1-oxopropan-2-yl(ethyl)carbamate (105 mg, 80%) as a white solid. MS m/z 712 (MNa)+.

Step 3: A rt solution of tert-butyl(S)-1-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-ylamino)-1-oxopropan-2-yl(ethyl)carbamate (104 mg, 151 μmol) in 4 M HCl in dioxane (754 μl) was stirred for 1 h. The reaction was diluted with Et2O (10 mL) and the solids were collected by vacuum filtration, taken up in MeCN—H2O, and lyophilized to provide (S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)propanamide hydrochloride (72.1 mg, 76%) as a white solid. MS m/z 590 (MH)+.

Example 29

(S)-N-((3S,4S)-7-Cyano-4-methyl-1-((2-methyl-naphthalen-1-yl)methyl)-5-(2-(methylsulfonyl)acetyl)-2-oxo-2,3,4,5-tetrahydro-1H-benzo[b][1,4]diazepin-3-yl)-2-(methylamino)butanamide hydrochloride

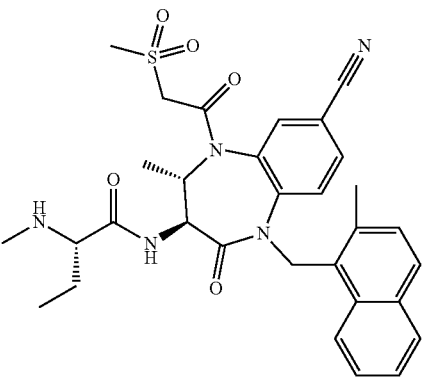 [SMILES: CC[C@H](NC)C(=O)N[C@@H]1C(=O)N(Cc2c(C)ccc3ccccc23)c2ccc(C#N)cc2N(C(=O)CS(C)(=O)=O)[C@H]1C]

Step 1: To a 0° C. solution of (S)-2-(tert-butoxycarbonylamino)butanoic acid (1.00 g, 4.92 mmol) in THF (16.4 ml) was added iodomethane (2.45 ml, 39.4 mmol) followed by sodium hydride (60% w/w dispersion in mineral oil, 590 mg, 14.8 mmol), portionwise. The reaction was allowed to warm to rt and stirred for 18 h, then cooled to 0° C., quenched by the careful addition of H2O, and washed with Et20. The aqueous layer was acidified by the addition of 1 M aq. HCl and extracted with Et20. The combined organic layers were washed with sat. aq. NaCl, dried over Na2SO4, filtered, and concentrated to provide (S)-2-(tert-butoxycarbonyl(methyl)amino)butanoic acid (1.05 g, 98%) as a white solid. MS m/z 240 (MNa)+.

Step 2: To a rt solution of (3S,4S)-3-amino-4-methyl-1-((2-methylnaphthalen-1-yl)methyl)-5-(2-(methylsulfonyl)acetyl)-2-oxo-2,3,4,5-tetrahydro-1H-benzo[b][1,4]diazepine-7-carbonitrile hydrochloride (100 mg, 190 μmol) in DMF (632 μl) was added (S)-2-(tert-butoxycarbonyl(methyl)amino)butanoic acid (45.3 mg, 209 μmol), N,N-diisopropylethylamine (131 μl, 759 μmol), and HBTU (79.2 mg, 209 μmol). The reaction was stirred at rt for 30 min, then purified by reverse phase preparative HPLC to provide tert-butyl(S)-1-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-ylamino)-1-oxobutan-2-yl(methyl)carbamate (118 mg, 90%) as a white solid. MS m/z 712 (MNa)+.

Step 3: A rt solution of tert-butyl(S)-1-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-ylamino)-1-oxobutan-2-yl(methyl)carbamate (117 mg, 170 μmol) in 4 M HCl in dioxane (848 μl) was stirred for 1 h. The reaction was diluted with Et2O and the resulting solids were collected by vacuum filtration, taken up in MeCN—H2O, and lyophilized to provide (S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H- benzo[b][1,4]diazepin-3-yl)-2-(methylamino)butanamide hydrochloride (90.5 mg, 85%) as a white solid. MS m/z 590 (MH)+.

Example 30

(S)-N-((3S,4S)-7-Cyano-4-methyl-1-((2-methyl-naphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)butanamide hydrochloride

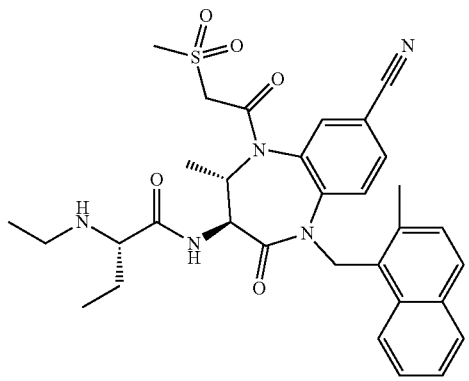 [SMILES: CCN[C@@H](CC)C(=O)N[C@@H]1C(=O)N(Cc2c(C)ccc3ccccc23)c2ccc(C#N)cc2N(C(=O)CS(C)(=O)=O)[C@H]1C]

Step 1: To a 0° C. solution of (S)-2-(tert-butoxycarbonylamino)butanoic acid (1.00 g, 4.92 mmol) in THF (16.4 ml) was added iodoethane (3.15 ml, 39.4 mmol) followed by sodium hydride (60% w/w dispersion in mineral oil, 590 mg, 14.8 mmol), portionwise. The reaction was allowed to warm to rt and stirred for 18 h, then cooled to 0° C., quenched by the careful addition of H2O, and washed with Et2O. The aqueous layer was acidified by the addition of 1 M aq. HCl and extracted with Et2O. The combined organic layers were washed with sat. aq. NaCl, dried over Na2SO4, filtered, and concentrated to provide a mixture of (S)-2-(tert-butoxycarbonyl(ethyl)amino)butanoic acid and (S)-2-(tert-butoxycarbonylamino)butanoic acid (1.02 g) as a yellow oil.

Step 2: To a 0° C. solution of (3S,4S)-3-amino-4-methyl-1-((2-methylnaphthalen-1-yl)methyl)-5-(2-(methylsulfonyl)acetyl)-2-oxo-2,3,4,5-tetrahydro-1H-benzo[b][1,4]diazepine-7-carbonitrile hydrochloride (210 mg, 398 µmol) in DMF (1.33 ml) was added the above mixture of (S)-2-(tert-butoxycarbonyl(ethyl)amino)butanoic acid and (S)-2-(tert-butoxycarbonylamino)butanoic acid (101 mg), N,N-diisopropylethylamine (276 µl, 1.59 mmol), and HBTU (166 mg, 438 µmol). The reaction was stirred at rt for 30 min, then purified by reverse phase preparative HPLC to provide tert-butyl(S)-1-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-ylamino)-1-oxobutan-2-yl)ethyl)carbamate (45 mg, 16%) as a white solid. MS m/z 726 (MNa)+.

Step 3: A rt solution of tert-butyl(S)-1-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-ylamino)-1-oxobutan-2-yl)ethyl)carbamate (45 mg, 63.9 µmol) in 4 M HCl in dioxane (320 µl) was stirred for 1.5 h. The reaction was diluted with Et2O and the solids were collected by vacuum filtration, taken up in MeCN—H2O, and lyophilized to provide (S)-N-((3S,4S)-7-cyano-4-methyl-1-((2-methylnaphthalen-1-yl)methyl)-5-(2-(methyl-sulfonyl)acetyl)-2-oxo-2,3,4,5-tetrahydro-1H-benzo[b][1,4]diazepin-3-yl)-2-(ethylamino)butanamide hydrochloride (33.1 mg, 81%) as a white solid. MS m/z 604 (MH)+.

Example 31

(S)-N-((3S,4S)-5-Acetyl-7-cyano-1-((2-methoxynaphthalen-1-yl)methyl)-4-methyl-2-oxo-2,3,4,5-tetrahydro-1H-benzo[b][1,4]diazepin-3-yl)-2-(methylamino)propanamide hydrochloride

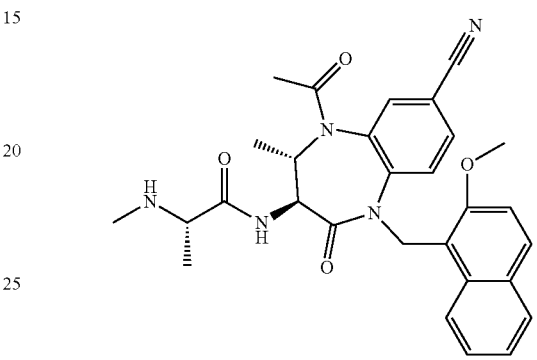

Step 1: To a rt solution of tert-butyl(S)-1-((2S,3S)-1-acetyl-8-cyano-2-methyl-4-oxo-2,3,4,5-tetrahydro-1H-benzo[b][1,4]diazepin-3-ylamino)-1-oxopropan-2-yl(methyl)carbamate (53 mg, 120 µmol) in DMF (299 µl) was added 1-(chloromethyl)-2-methoxynaphthalene (29.6 mg, 143 µmol), cesium carbonate (50.6 mg, 155 µmol), and sodium iodide (23.3 mg, 155 µmol). The reaction was stirred at rt for 1 h, then diluted with EtOAc, washed with H2O and sat. aq. NaCl, dried over Na2SO4, filtered, and concentrated. The crude material was purified by flash chromatography to provide tert-butyl(S)-1-((3S,4S)-5-acetyl-7-cyano-1-((2-methoxynaphthalen-1-yl)methyl)-4-methyl-2-oxo-2,3,4,5-tetrahydro-1H-benzo[b][1,4]diazepin-3-ylamino)-1-oxopropan-2-yl(methyl)carbamate (60 mg, 82%) as a white solid. MS m/z 636 (MNa)+.

Step 2: A rt solution of tert-butyl(S)-1-((3S,4S)-5-acetyl-7-cyano-1-((2-methoxynaphthalen-1-yl)methyl)-4-methyl-2-oxo-2,3,4,5-tetrahydro-1H-benzo[b][1,4]diazepin-3-ylamino)-1-oxopropan-2-yl(methyl)carbamate (60 mg, 97.8 µmol) in 4 M HCl in dioxane (489 µl) was stirred for 1 h. The reaction was diluted with Et2O and the solids were collected by vacuum filtration, taken up in MeCN—H2O, and lyophilized to provide (S)-N-((3S,4S)-5-acetyl-7-cyano-1-((2-methoxynaphthalen-1-yl)methyl)-4-methyl-2-oxo-2,3,4,5-tetrahydro-1H-benzo[b][1,4]diazepin-3-yl)-2-(methylamino)propanamide hydrochloride (43.0 mg, 80%) as an off-white solid. MS m/z 514 (MH)+.

Alternate Procedure for Example 31

Step 1: To a rt solution of tert-butyl(3S,4S)-7-cyano-4-methyl-2-oxo-2,3,4,5-tetrahydro-1H-benzo[b][1,4]diazepin-3-ylcarbamate (406 mg, 1.28 mmol) in DMF (3.21 ml) was added 1-(chloromethyl)-2-methoxynaphthalene (318 mg, 1.54 mmol) and cesium carbonate (1.25 g, 3.85 mmol).

The reaction was stirred at rt for 16 h, then diluted with EtOAc, washed with H2O and sat. aq. NaCl, dried over Na2SO4, filtered, and concentrated. The crude material was purified by flash chromatography to provide tert-butyl(3S,4S)-7-cyano-1-((2-methoxynaphthalen-1-yl)methyl)-4-methyl-2-oxo-2,3,4,5-tetrahydro-1H-benzo[b][1,4]diazepin-3-ylcarbamate (448 mg, 72%) as an off-white solid. MS m/z 509 (MNa)+.

Step 2: To a 0° C. solution of tert-butyl(3S,4S)-7-cyano-1-((2-methoxynaphthalen-1-yl)methyl)-4-methyl-2-oxo-2,3,4,5-tetrahydro-1H-benzo[b][1,4]diazepin-3-ylcarbamate (448 mg, 921 µmol) in CH2Cl2 (9.21 ml) was added pyridine (375 µl, 4.6 mmol), followed by acetyl chloride (78.8 µl, 1.1 mmol), dropwise. The reaction was stirred at 0° C. for 1 h, then allowed to warm to rt and stirred for an additional 20 h, then quenched by the addition of H2O and extracted with CH2Cl2. The combined organic layers were washed with sat. aq. NaHCO3 and sat. aq. NaCl, dried over Na2SO4, filtered, and concentrated. The crude material was purified by flash chromatography to provide tert-butyl(3S,4S)-5-acetyl-7-cyano-1-((2-methoxynaphthalen-1-yl)methyl)-4-methyl-2-oxo-2,3,4,5-tetrahydro-1H-benzo[b][1,4]diazepin-3-ylcarbamate (316 mg, 65%) as a white solid. MS m/z 551 (MNa)+.

Step 3: A rt solution of tert-butyl(3S,4S)-5-acetyl-7-cyano-1-((2-methoxynaphthalen-1-yl)methyl)-4-methyl-2-oxo-2,3,4,5-tetrahydro-1H-benzo[b][1,4]diazepin-3-ylcarbamate (316 mg, 598 µmol) in 4 M HCl in dioxane (2.99 ml) was stirred for 2 h. The reaction was diluted with Et2O and the solids were collected by vacuum filtration to provide (3S,4S)-5-acetyl-3-amino-1-((2-methoxynaphthalen-1-yl)methyl)-4-methyl-2-oxo-2,3,4,5-tetrahydro-1H-benzo[b][1,4]diazepine-7-carbonitrile hydrochloride (216 mg, 78%) as a white solid.

Step 4: To a 0° C. solution of (3S,4S)-5-acetyl-3-amino-1-((2-methoxynaphthalen-1-yl)methyl)-4-methyl-2-oxo-2,3,4,5-tetrahydro-1H-benzo[b][1,4]diazepine-7-carbonitrile hydrochloride (216 mg, 465 µmol) in DMF (1.55 ml) was added Boc-N-methyl-L-alanine (104 mg, 511 µmol), N,N-diisopropylethylamine (322 µl, 1.86 mmol), and HBTU (194 mg, 511 µmol). The reaction was stirred at rt for 30 min, then diluted with H2O and the solids were collected by vacuum filtration, taken up in EtOAc, washed with H2O, sat. aq. NaHCO3, and sat. aq. NaCl, dried over Na2SO4, filtered, and concentrated. The crude material was purified by flash chromatography to provide tert-butyl(S)-1-((3S,4S)-5-acetyl-7-cyano-1-((2-methoxynaphthalen-1-yl)methyl)-4-methyl-2-oxo-2,3,4,5-tetrahydro-1H-benzo[b][1,4]diazepin-3-ylamino)-1-oxopropan-2-yl(methyl)carbamate (255 mg, 89%) as a white solid. MS m/z 636 (MNa)+.

Step 5: A rt solution of tert-butyl(S)-1-((3S,4S)-5-acetyl-7-cyano-1-((2-methoxynaphthalen-1-yl)methyl)-4-methyl-2-oxo-2,3,4,5-tetrahydro-1H-benzo[b][1,4]diazepin-3-ylamino)-1-oxopropan-2-yl(methyl)carbamate (255 mg, 416 µmol) in 4 M HCl in dioxane (2.08 ml) was stirred for 45 min. The reaction was diluted with Et2O and the solids were collected by vacuum filtration, taken up in MeCN—H2O, and lyophilized to provide (S)-N-((3S,4S)-5-acetyl-7-cyano-1-((2-methoxynaphthalen-1-yl)methyl)-4-methyl-2-oxo-2,3,4,5-tetrahydro-1H-benzo[b][1,4]diazepin-3-yl)-2-(methylamino)propanamide hydrochloride (181.8 mg, 80%) as a white solid. MS m/z 514 (MH)+.

Example 32

(S)-N-((3S,4S)-5-Acetyl-7-cyano-4-methyl-1-((2-methylnaphthalen-1-yl)methyl)-2-oxo-2,3,4,5-tetrahydro-1H-benzo[b][1,4]diazepin-3-yl)-2-(methylamino)propanamide hydrochloride

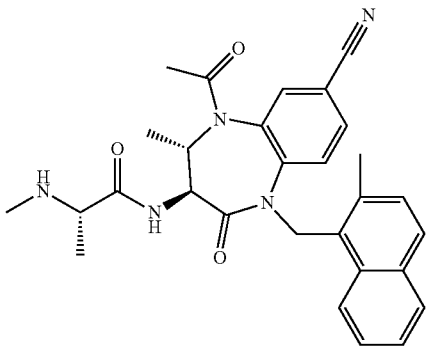 [SMILES: CN[C@@H](C)C(=O)N[C@@H]1C(=O)N(Cc2c(C)ccc3ccccc23)c2ccc(C#N)cc2N(C(C)=O)[C@H]1C]

Step 1: To a rt solution of tert-butyl(S)-1-((2S,3S)-1-acetyl-8-cyano-2-methyl-4-oxo-2,3,4,5-tetrahydro-1H-benzo[b][1,4]diazepin-3-ylamino)-1-oxopropan-2-yl(methyl)carbamate (57 mg, 129 µmol) in DMF (321 µl) was added 1-(chloromethyl)-2-methylnaphthalene (29.4 mg, 154 µmol), cesium carbonate (54.4 mg, 167 µmol), and sodium iodide (25.0 mg, 167 µmol). The reaction was stirred at rt for 1 h, then diluted with EtOAc, washed with H2O and sat. aq. NaCl, dried over Na2SO4, filtered, and concentrated. The crude material was purified by flash chromatography to provide tert-butyl(S)-1-((3S,4S)-5-acetyl-7-cyano-4-methyl-1-((2-methylnaphthalen-1-yl)methyl)-2-oxo-2,3,4,5-tetrahydro-1H-benzo[b][1,4]diazepin-3-ylamino)-1-oxopropan-2-yl(methyl)carbamate (56.3 mg, 73%) as a white solid. MS m/z 620 (MNa)+.

Step 2: A rt solution of tert-butyl(S)-1-((3S,4S)-5-acetyl-7-cyano-4-methyl-1-((2-methylnaphthalen-1-yl)methyl)-2-oxo-2,3,4,5-tetrahydro-1H-benzo[b][1,4]diazepin-3-ylamino)-1-oxopropan-2-yl(methyl)carbamate (56.3 mg, 94.2 µmol) in 4 M HCl in dioxane (471 µl) was stirred for 1 h. The reaction was diluted with Et2O and the solids were collected by vacuum filtration, taken up in MeCN—H2O, and lyophilized to provide (S)-N-((3S,4S)-5-acetyl-7-cyano-4-methyl-1-((2-methylnaphthalen-1-yl)methyl)-2-oxo-2,3,4,5-tetrahydro-1H-benzo[b][1,4]diazepin-3-yl)-2-(methylamino)propanamide hydrochloride (44.4 mg, 88%) as a white solid. MS m/z 498 (MH)+.

Alternate Procedure for Example 32

Step 1: To a rt solution of tert-butyl(3S,4S)-7-cyano-4-methyl-2-oxo-2,3,4,5-tetrahydro-1H-benzo[b][1,4]diazepin-3-ylcarbamate (308 mg, 974 µmol) in DMF (2.43 ml) was added 1-(chloromethyl)-2-methylnaphthalene (223 mg, 1.17 mmol) and cesiuim carbonate (952 mg, 2.92 mmol). The reaction was stirred at rt for 2 h, then diluted with EtOAc, washed with H2O and sat. aq. NaCl, dried over Na2SO4, filtered, and concentrated. The crude material was purified by flash chromatography to provide tert-butyl(3S,4S)-7-cyano-4-methyl-1-((2-methylnaphthalen-1-yl)methyl)-2-oxo-2,3, 4,5-tetrahydro-1H-benzo[b][1,4]diazepin-3-ylcarbamate (364 mg, 80% yield) as an off-white oil. MS m/z 493 (MNa)+.

Step 2: To a 0° C. solution of tert-butyl(3S,4S)-7-cyano-4-methyl-1-((2-methylnaphthalen-1-yl)methyl)-2-oxo-2,3,4,5-tetrahydro-1H-benzo[b][1,4]diazepin-3-ylcarbamate (364 mg, 774 µmol) in CH2Cl2 (7.74 ml) was added pyridine (306 mg, 315 µl, 3.87 mmol), followed by acetyl chloride (71.8 µl, 1.01 mmol), dropwise. The reaction was stirred at 0° C. for 1 h, then allowed to warm to rt and stirred for an additional 15 h, then quenched by the addition of H2O and extracted with CH2Cl2. The combined organic layers were washed with sat. aq. NaHCO3 and sat. aq. NaCl, dried over Na2SO4, filtered, and concentrated. The crude material was purified by flash chromatography to provide tert-butyl(3S,4S)-5-acetyl-7-cyano-4-methyl-1-((2-methylnaphthalen-1-yl)methyl)-2-oxo-2,3,4,5-tetrahydro-1H-benzo[b][1,4]diazepin-3-ylcarbamate (235 mg, 59%) as a white solid. MS m/z 535 (MNa)+.

Step 3: A rt solution of tert-butyl(3S,4S)-5-acetyl-7-cyano-4-methyl-1-((2-methylnaphthalen-1-yl)methyl)-2-oxo-2,3,4,5-tetrahydro-1H-benzo[b][1,4]diazepin-3-ylcarbamate (235 mg, 458 µmol) in 4 M HCl in dioxane (2.29 ml) was stirred for 2 h. The reaction was diluted with Et2O and the solids were collected by vacuum filtration to provide (3S,4S)-5-acetyl-3-amino-4-methyl-1-((2-methylnaphthalen-1-yl)methyl)-2-oxo-2,3,4,5-tetrahydro-1H-benzo[b][1,4]diazepine-7-carbonitrile hydrochloride (162 mg, 79%) as a white solid.

Step 4: To a 0° C. solution of (3S,4S)-5-acetyl-3-amino-4-methyl-1-((2-methylnaphthalen-1-yl)methyl)-2-oxo-2,3,4,5-tetrahydro-1H-benzo[b][1,4]diazepine-7-carbonitrile hydrochloride (162 mg, 361 µmol) in DMF (1.2 ml) was added Boc-N-methyl-L-alanine (80.7 mg, 397 µmol), N,N-diisopropylethylamine (250 µl, 1.44 mmol), and HBTU (151 mg, 397 µmol). The reaction was stirred at rt for 30 min, then diluted with H2O and the solids were collected by vacuum filtration, taken up in EtOAc, washed with H2O, sat. aq. NaHCO3, and sat. aq. NaCl, dried over Na2SO4, filtered, and concentrated. The crude material was purified by flash chromatography to provide tert-butyl(S)-1-((3S,4S)-5-acetyl-7-cyano-4-methyl-1-((2-methylnaphthalen-1-yl)methyl)-2-oxo-2,3,4,5-tetrahydro-1H-benzo[b][1,4]diazepin-3-ylamino)-1-oxopropan-2-yl(methyl)carbamate (189 mg, 88%) as a white solid. MS m/z 620 (MNa)+.

Step 5: A rt solution of tert-butyl(S)-1-((3S,4S)-5-acetyl-7-cyano-4-methyl-1-((2-methylnaphthalen-1-yl)methyl)-2-oxo-2,3,4,5-tetrahydro-1H-benzo[b][1,4]diazepin-3-ylamino)-1-oxopropan-2-yl(methyl)carbamate (187 mg, 313 µmol) in 4 M HCl in dioxane (1.56 ml) was stirred for 45 min. The reaction was diluted with Et2O and the solids were collected by vacuum filtration, taken up in MeCN—H2O, and lyophilized to provide (S)-N-((3S,4S)-5-acetyl-7-cyano-4-methyl-1-((2-methylnaphthalen-1-yl)methyl)-2-oxo-2,3,4,5-tetrahydro-1H-benzo[b][1,4]diazepin-3-yl)-2-(methylamino)propanamide hydrochloride (145.5 mg, 87%) as a white solid. MS m/z 498 (MH)+.

Example 33

(S)-N-((3S,4S)-5-Acetyl-7-cyano-1-((3-cyclopropylquinolin-4-yl)methyl)-4-methyl-2-oxo-2,3,4,5-tetrahydro-1H-benzo[b][1,4]diazepin-3-yl)-2-(methylamino)propanamide dihydrochloride

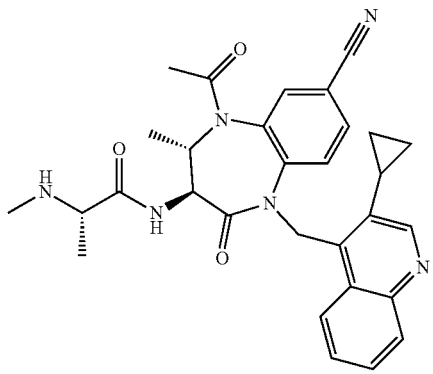 [SMILES: CN[C@@H](C)C(=O)N[C@@H]1C(=O)N(Cc2c(C3CC3)cnc3ccccc23)c2ccc(C#N)cc2N(C(C)=O)[C@H]1C]

Step 1: To a rt solution of tert-butyl(3S,4S)-7-cyano-4-methyl-2-oxo-2,3,4,5-tetrahydro-1H-benzo[b][1,4]diazepin-3-ylcarbamate (155 mg, 490 µmol) in DMF (1.22 ml) was added (3-cyclopropylquinolin-4-yl)methyl methanesulfonate (149 mg, 539 µmol) and cesium carbonate (479 mg, 1.47 mmol). The reaction was stirred at rt for 2.5 h, then diluted with EtOAc, washed with H2O and sat. aq. NaCl, dried over Na2SO4, filtered, and concentrated. The crude material was purified by flash chromatography to provide tert-butyl(3S,4S)-7-cyano-1-((3-cyclopropylquinolin-4-yl)methyl)-4-methyl-2-oxo-2,3,4,5-tetrahydro-1H-benzo[b][1,4]diazepin-3-ylcarbamate (145 mg, 60%) as a white solid. MS m/z 498 (MH)+.

Step 2: A rt suspension of tert-butyl(3S,4S)-7-cyano-1-((3-cyclopropylquinolin-4-yl)methyl)-4-methyl-2-oxo-2,3,4,5-tetrahydro-1H-benzo[b][1,4]diazepin-3-ylcarbamate (134 mg, 269 µmol) in 4 M HCl in dioxane (1.35 ml) was stirred for 2.5 h. The reaction was diluted with Et2O and the solids were collected by vacuum filtration to provide (3S,4S)-3-amino-1-((3-cyclopropylquinolin-4-yl)methyl)-4-methyl-2-oxo-2,3,4,5-tetrahydro-1H-benzo[b][1,4]diazepine-7-carbonitrile dihydrochloride (127 mg, quant.) as an off-white solid. MS m/z 398 (MH)+.

Step 3: To a rt solution of (3S,4S)-3-amino-1-((3-cyclopropylquinolin-4-yl)methyl)-4-methyl-2-oxo-2,3,4,5-tetrahydro-1H-benzo[b][1,4]diazepine-7-carbonitrile dihydrochloride (126 mg, 268 µmol) in DMF (893 µl) was added Boc-N-methyl-L-alanine (59.9 mg, 295 µmol), N,N-diisopropylethylamine (232 µl, 1.34 mmol), and HBTU (112 mg, 295 µmol). The reaction was stirred at rt for 1 h, then diluted with EtOAc, washed with H2O, sat. aq. NaHCO3, and sat. aq. NaCl, dried over Na2SO4, filtered, and concentrated. The crude material was purified by flash chromatography to provide tert-butyl(S)-1-((3S,4S)-7-cyano-1-((3-cyclopropylquinolin-4-yl)methyl)-4-methyl-2-oxo-2,3,4,5-tetrahydro-1H-benzo[b][1,4]diazepin-3-ylamino)-1-oxopropan-2-yl(methyl)carbamate (144 mg, 92%) as a white solid. MS m/z 583 (MH)+.

Step 4: To a rt solution of tert-butyl(S)-1-((3S,4S)-7-cyano-1-((3-cyclopropylquinolin-4-yl)methyl)-4-methyl-2-oxo-2,3,4,5-tetrahydro-1H-benzo[b][1,4]diazepin-3-ylamino)-1-oxopropan-2-yl(methyl)carbamate (70 mg, 120 µmol) in CH2Cl2 (801 µl) was added pyridine (29.4 µl, 360 µmol), followed by acetyl chloride (12.8 µl, 180 µmol), dropwise. The reaction was stirred at rt for 22 h, then diluted with H2O and extracted with CH2Cl2. The combined organic layers were washed with sat. aq. NaHCO3 and sat. aq. NaCl, dried over Na2SO4, filtered, and concentrated. The crude material was purified by reverse phase preparative HPLC then flash chromatography to provide tert-butyl(S)-1-((3S,4S)-5-acetyl-7-cyano-1-((3-cyclopropylquinolin-4-yl)methyl)-4-methyl-2-oxo-2,3,4,5-tetrahydro-1H-benzo[b][1,4]diazepin-3-ylamino)-1-oxopropan-2-yl(methyl)carbamate (26.8 mg, 36%) as a white solid. MS m/z 625 (MH)+.

Step 5: A rt suspension of tert-butyl(S)-1-((3S,4S)-5-acetyl-7-cyano-1-((3-cyclopropylquinolin-4-yl)methyl)-4-methyl-2-oxo-2,3,4,5-tetrahydro-1H-benzo[b][1,4]diazepin-3-ylamino)-1-oxopropan-2-yl(methyl)carbamate (26.8 mg, 42.9 µmol) in 4 M HCl in dioxane (214 µl) was stirred at rt for 2 h. The reaction was diluted with Et2O and the solids were collected by vacuum filtration, taken up in MeCN—H2O, and lyophilized to provide (S)-N-((3S,4S)-5-acetyl-7-cyano-1-((3-cyclopropylquinolin-4-yl)methyl)-4-methyl-2-oxo-2,3,4,5-tetrahydro-1H-benzo[b][1,4]diazepin-3-yl)-2-(methylamino)propanamide dihydrochloride (21.9 mg, 85%) as a white solid. MS m/z 525 (MH)+.

Example 34

(S)-N-((3S,4S)-7-Cyano-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride

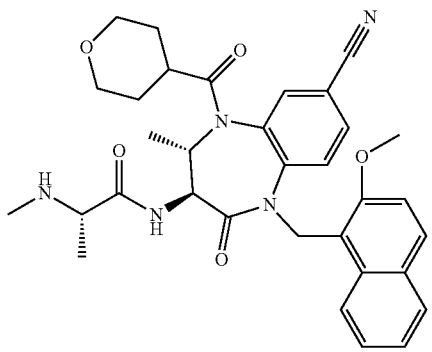 [SMILES: CN[C@@H](C)C(=O)N[C@@H]1C(=O)N(Cc2c(OC)ccc3ccccc23)c2ccc(C#N)cc2N(C(=O)C2CCOCC2)[C@H]1C]

Step 1: To a rt solution of tert-butyl(S)-1-((2S,3S)-8-cyano-2-methyl-4-oxo-1-(tetrahydro-2H-pyran-4-carbonyl)-2,3,4,5-tetrahydro-1H-benzo[b][1,4]diazepin-3-ylamino)-1-oxopropan-2-yl(methyl)carbamate (65 mg, 127 µmol) in DMF (316 µl) was added 1-(chloromethyl)-2-methoxynaphthalene (31.4 mg, 152 µmol), cesium carbonate (53.6 mg, 165 µmol), and sodium iodide (24.7 mg, 165 µmol). The reaction was stirred at rt for 1 h, then diluted with EtOAc, washed with H2O and sat. aq. NaCl, dried over Na2SO4, filtered, and concentrated. The crude material was purified by flash chromatography to provide tert-butyl(S)-1-((3S,4S)-7-cyano-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-ylamino)-1-oxopropan-2-yl(methyl)carbamate (75 mg, 87%) as a white solid. MS m/z 706 (MNa)+.

Step 2: A rt solution of tert-butyl(S)-1-((3S,4S)-7-cyano-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-ylamino)-1-oxopropan-2-yl(methyl)carbamate (75 mg, 110 µmol) in 4 M HCl in dioxane (548 µl) was stirred for 1 h. The reaction was diluted with Et2O and the solids were collected by vacuum filtration, taken up in MeCN—H2O, and lyophilized to provide (S)-N-((3S,4S)-7-cyano-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride (57.0 mg, 84% yield) as a white solid. MS m/z 584 (MH)+.

Example 35

(S)-N-((3S,4S)-7-Cyano-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide dihydrochloride

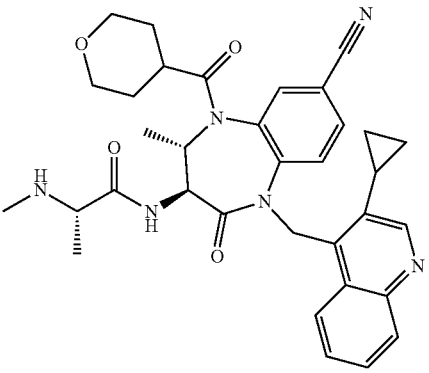 [SMILES: CN[C@@H](C)C(=O)N[C@@H]1C(=O)N(Cc2c(C3CC3)cnc3ccccc23)c2ccc(C#N)cc2N(C(=O)C2CCOCC2)[C@H]1C]

Step 1: To a rt solution of tert-butyl(3S,4S)-7-cyano-4-methyl-2-oxo-2,3,4,5-tetrahydro-1H-benzo[b][1,4]diazepin-3-ylcarbamate (400 mg, 1.26 mmol) in DMF (3.16 ml) was added (3-cyclopropylquinolin-4-yl)methyl methanesulfonate (421 mg, 1.52 mmol) and cesium carbonate (1.24 g, 3.79 mmol). The reaction was stirred at rt for 16 h, then diluted with EtOAc, washed with H2O and sat. aq. NaCl, dried over Na2SO4, filtered, and concentrated. The crude material was purified by flash chromatography to provide tert-butyl(3S,4S)-7-cyano-1-((3-cyclopropylquinolin-4-yl)methyl)-4-methyl-2-oxo-2,3,4,5-tetrahydro-1H-benzo[b][1,4]diazepin-3-ylcarbamate (498 mg, 79%) as an off-white solid. MS m/z 498 (MH)+.

Step 2: To a rt solution of tert-butyl(3S,4S)-7-cyano-1-((3-cyclopropylquinolin-4-yl)methyl)-4-methyl-2-oxo-2,3,4,5-tetrahydro-1H-benzo[b][1,4]diazepin-3-ylcarbamate (93 mg, 187 µmol) in pyridine (374 µl) was added tetrahydro-2H-pyran-4-carbonyl chloride (139 mg, 935 µmol) dropwise. The reaction was stirred at 80° C. for 2 h, then cooled to rt, diluted with EtOAc, washed with H2O, sat. aq. NaHCO3, and sat. aq. NaCl, dried over Na2SO4, filtered, and concentrated. The crude material was purified by flash chromatography to provide tert-butyl(3S,4S)-7-cyano-1-((3-cyclopropylquinolin-4-yl)methyl)-4-methyl-2-oxo-5-(tetrahydro-2H-pyran-4- carbonyl)-2,3,4,5-tetrahydro-1H-benzo[b][1,4]diazepin-3-ylcarbamate (69 mg, 61%) as an off-white solid. MS m/z 610 (MH)+.

Step 3: A rt solution of tert-butyl(3S,4S)-7-cyano-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-ylcarbamate (69 mg, 113 µmol) in 4 M HCl in dioxane (566 µl) was stirred for 2 h. The reaction was diluted with Et2O and the solids were collected by vacuum filtration to provide (3S,4S)-3-amino-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepine-7-carbonitrile dihydrochloride (60 mg, 91%) as a white solid.

Step 4: To a 0° C. solution of (3S,4S)-3-amino-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepine-7-carbonitrile dihydrochloride (60 mg, 103 µmol) in DMF (343 µl) was added Boc-N-methyl-L-alanine (23.0 mg, 113 µmol), N,N-diisopropylethylamine (89.1 µl, 515 µmol), and HBTU (43.0 mg, 113 µmol). The reaction was stirred at rt for 30 min, then diluted with EtOAc, washed with H2O, sat. aq. NaHCO3, and sat. aq. NaCl, dried over Na2SO4, filtered, and concentrated. The crude material was purified by flash chromatography to provide tert-butyl(S)-1-((3S,4S)-7-cyano-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-ylamino)-1-oxopropan-2-yl(methyl)carbamate (55.3 mg, 77%) as a white solid. MS m/z 695 (MH)+.

Step 5: A rt solution of tert-butyl(S)-1-((3S,4S)-7-cyano-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-ylamino)-1-oxopropan-2-yl(methyl)carbamate (53 mg, 76.3 µmol) in 4 M HCl in dioxane (381 µl) was stirred for 2 h. The reaction was diluted with Et2O and the solids were collected by vacuum filtration to provide (S)-N-((3S,4S)-7-cyano-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide dihydrochloride (41.4 mg, 81%) as a white solid. MS m/z 595 (MH)+.

Example 36

(S)-N-((3S,4S)-5-Acetyl-1-(5-bromo-2-methoxybenzyl)-7-cyano-4-methyl-2-oxo-2,3,4,5-tetrahydro-1H-benzo[b][1,4]diazepin-3-yl)-2-(methylamino)propanamide hydrochloride

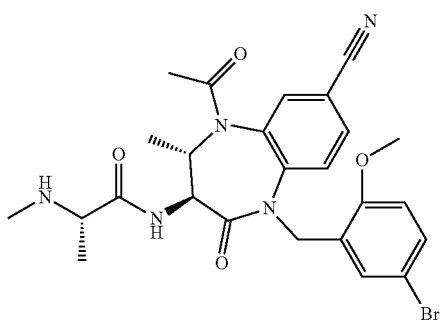 [SMILES: CN[C@@H](C)C(=O)N[C@@H]1C(=O)N(Cc2cc(Br)ccc2OC)c2ccc(C#N)cc2N(C(C)=O)[C@H]1C]

A rt solution of tert-butyl(S)-1-((3S,4S)-5-acetyl-1-(5-bromo-2-methoxybenzyl)-7-cyano-4-methyl-2-oxo-2,3,4,5-tetrahydro-1H-benzo[b][1,4]diazepin-3-ylamino)-1-oxopropan-2-yl(methyl)carbamate (35.5 mg, 55.2 µmol) in 4 M HCl in dioxane (276 µl) was stirred for 1 h. The reaction was diluted with Et2O and the solids were collected by vacuum filtration, taken up in MeCN—H2O, and lyophilized to provide (S)-N-((3S,4S)-5-acetyl-1-(5-bromo-2-methoxybenzyl)-7-cyano-4-methyl-2-oxo-2,3,4,5-tetrahydro-1H-benzo[b][1,4]diazepin-3-yl)-2-(methylamino)propanamide hydrochloride (23.0 mg, 72%) as a white solid. MS m/z 542/544 (MH)+.

Example 37

(S)-N-((3S,4S)-5-Acetyl-7-cyano-1-((4-methoxybiphenyl-3-yl)methyl)-4-methyl-2-oxo-2,3,4,5-tetrahydro-1H-benzo[b][1,4]diazepin-3-yl)-2-(methylamino)propanamide hydrochloride

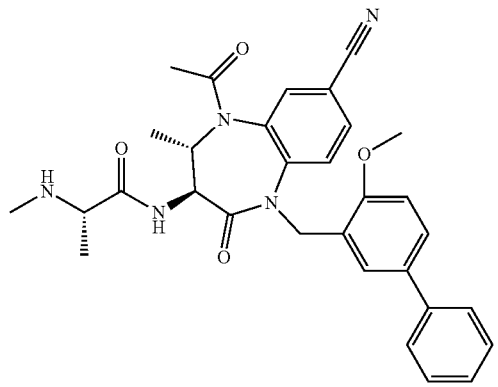 [SMILES: CN[C@@H](C)C(=O)N[C@@H]1C(=O)N(Cc2cc(-c3ccccc3)ccc2OC)c2ccc(C#N)cc2N(C(C)=O)[C@H]1C]

Step 1: A rt suspension of tert-butyl(S)-1-((3S,4S)-5-acetyl-1-(5-bromo-2-methoxybenzyl)-7-cyano-4-methyl-2-oxo-2,3,4,5-tetrahydro-1H-benzo[b][1,4]diazepin-3-ylamino)-1-oxopropan-2-yl(methyl)carbamate (24 mg, 37.4 µmol), phenylboronic acid (6.83 mg, 56.0 µmol), and sodium bicarbonate (7.84 mg, 93.4 µmol) in 1,4-dioxane (280 µl) was sparged with Ar for 5 min, then [1,1'-bis(diphenylphosphino)ferrocene]dichloropalladium(II) dichloromethane complex (3.05 mg, 3.74 µmol) was added. The reaction was sparged with Ar for an additional minute, then sealed and stirred at 80° C. for 2 h, then cooled to rt, diluted with EtOAc, washed with H2O and sat. aq. NaCl, dried over Na2SO4, filtered, and concentrated. The crude material was purified by flash chromatography to provide tert-butyl(S)-1-((3S,4S)-5-acetyl-7-cyano-1-((4-methoxybiphenyl-3-yl)methyl)-4-methyl-2-oxo-2,3,4,5-tetrahydro-1H-benzo[b][1,4]diazepin-3-ylamino)-1-oxopropan-2-yl(methyl)carbamate (18 mg, 75%) as a white solid. MS m/z 662 (MNa)+.

Step 2: A rt solution of tert-butyl(S)-1-((3S,4S)-5-acetyl-7-cyano-1-((4-methoxybiphenyl-3-yl)methyl)-4-methyl-2-oxo-2,3,4,5-tetrahydro-1H-benzo[b][1,4]diazepin-3-ylamino)-1-oxopropan-2-yl(methyl)carbamate (37 mg, 57.8 µmol) in 4 M HCl in dioxane (289 µl) was stirred for 1 h. The reaction was diluted with Et2O and the solids were collected by vacuum filtration, taken up in MeCN—H2O, and lyophilized to provide (S)-N-((3S,4S)-5-acetyl-7-cyano-1-((4-methoxybiphenyl-3-yl)methyl)-4-methyl-2-oxo-2,3,4,5-tetrahydro-1H-benzo[b][1,4]diazepin-3-yl)-2-(methylamino)
propanamide hydrochloride (29.0 mg, 87%) as a white solid.
MS m/z 540 (MH)+.

Example 38

(S)-N-((3S,4S)-5-Acetyl-7-cyano-1-((2'-fluoro-4-
methoxybiphenyl-3-yl)methyl)-4-methyl-2-oxo-2,3,
4,5-tetrahydro-1H-benzo[b][1,4]diazepin-3-yl)-2-
(methylamino)propanamide hydrochloride

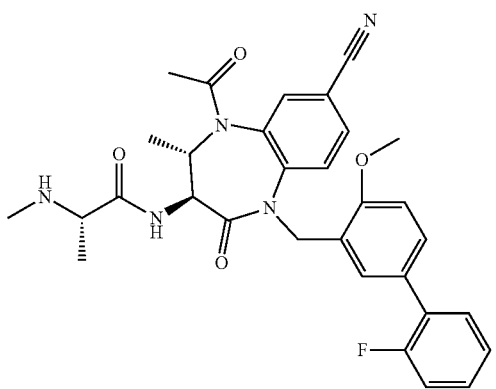 [SMILES: CN[C@@H](C)C(=O)N[C@@H]1C(=O)N(Cc2cc(-c3ccccc3F)ccc2OC)c2ccc(C#N)cc2N(C(C)=O)[C@H]1C]

Step 1: A rt suspension of tert-butyl(S)-1-((3S,4S)-5-acetyl-1-(5-bromo-2-methoxybenzyl)-7-cyano-4-methyl-2-oxo-2,3,4,5-tetrahydro-1H-benzo[b][1,4]diazepin-3-yl amino)-1-oxopropan-2-yl(methyl)carbamate (50.4 mg, 78.4 µmol), 2-fluorophenylboronic acid (16.5 mg, 118 µmol), and sodium bicarbonate (16.5 mg, 196 µmol) in 1,4-dioxane (588 µl) was sparged with Ar for 10 min, then [1,1'-bis(diphenylphosphino)ferrocene]dichloropalladium(II) dichloromethane complex (6.41 mg, 7.84 µmol) was added. The reaction was sparged with Ar for an additional minute, then sealed and stirred at 80° C. for 1.5 h, then cooled to rt, diluted with EtOAc, washed with H2O and sat. aq. NaCl, dried over Na2SO4, filtered, and concentrated. The crude material was purified by flash chromatography to provide tert-butyl(S)-1-((3S,4S)-5-acetyl-7-cyano-1-((2'-fluoro-4-methoxybiphenyl-3-yl)methyl)-4-methyl-2-oxo-2,3,4,5-tetrahydro-1H-benzo[b][1,4]diazepin-3-ylamino)-1-oxopropan-2-ylmethyl)carbamate (39.3 mg, 76%) as an off-white solid. MS m/z 680 (MNa)+.

Step 2: A rt solution of tert-butyl(S)-1-((3S,4S)-5-acetyl-7-cyano-1-((2'-fluoro-4-methoxybiphenyl-3-yl)methyl)-4-methyl-2-oxo-2,3,4,5-tetrahydro-1H-benzo[b][1,4]diazepin-3-ylamino)-1-oxopropan-2-yl(methyl)carbamate (39 mg, 59.3 µmol) in 4 M HCl in dioxane (296 µl) was stirred for 1 h. The reaction was diluted with Et2O and the solids were collected by vacuum filtration, taken up in MeCN—H2O, and lyophilized to provide (S)-N-((3S,4S)-5-acetyl-7-cyano-1-((2'-fluoro-4-methoxybiphenyl-3-yl)methyl)-4-methyl-2-oxo-2,3,4,5-tetrahydro-1H-benzo[b][1,4]diazepin-3-yl)-2-(methylamino)propanamide hydrochloride (23.9 mg, 68%) as a white solid. MS m/z 558 (MH)+.

The compounds listed in Table 1 below were prepared in a similar manner to that described in Example 12, using 1.1-1.2 equivalents of the appropriate alkyl chloride, bromide, or mesylate, 1.2-1.3 equivalents of cesium carbonate, and 1.2-1.3 equivalents of sodium iodide in Step 1. The reaction time for Step 1 ranged from 8-22 h. The reaction time for Step 2 ranged from 1-2.5 h.

TABLE 1

| Example | Final Product | MS m/z (MH)+ |
|---|---|---|
| 39 | (structure) | 528 |
| 40 | (structure) | 589 |
| 41 | (structure) | 606/608 |
| 42 | (structure) | 578 |

TABLE 1-continued

| Example | Final Product | MS m/z (MH)+ |
| --- | --- | --- |
| 43 | (structure) | 551 |

The compounds listed in Table 2 below were prepared in a similar manner to that described in Example 13, using 1.1-1.2 equivalents of the appropriate alkyl chloride, bromide, or mesylate, 1.2-1.3 equivalents of cesium carbonate, and 1.2-1.3 equivalents of sodium iodide in Step 1 (the sodium iodide was omitted in Example 47). The reaction time for Step 1 ranged from 16-20 h. The reaction time for Step 2 ranged from 1-2.5 h.

TABLE 2

| Example | Final Product | MS m/z (MH)+ |
| --- | --- | --- |
| 44 | (structure) | 628 |
| 45 | (structure) | 551 |
| 46 | (structure) | 541 |
| 47 | (structure) | 603 |
| 48 | (structure) | 568 |

The compounds listed in Table 3 below were prepared in a similar manner to that described in Example 17, using the appropriate alkyl chloride in Step 1. The reaction time for Step 1 ranged from 4-16 h. The reaction time for Step 2 ranged from 2-4 h.

TABLE 3

| Example | Final Product | MS m/z (MH)+ |
|---|---|---|
| 49 | | 611/613 |
| 50 | | 533 |

TABLE 4

| Example | Final Product | MS m/z (MH)+ |
|---|---|---|
| 51 | | 576 |
| 52 | | 603 |
| 53 | | 653 |

The compounds listed in Table 4 below were prepared in a similar manner to that described in Example 26, using 1.1-1.2 equivalents of the appropriate alkyl chloride, bromide, or mesylate, 1.2-1.3 equivalents of cesium carbonate, and 1.2 equivalents of sodium iodide in Step 1 (the sodium iodide was omitted in Example 52. The reaction time for Step 1 ranged from 1-4 h. The reaction time for Step 2 ranged from 1-2.5 h.

The compounds listed in Table 5 below were prepared in a similar manner to that described in Example 34, using the appropriate alkyl chloride or mesylate in Step 1. The reaction time for Step 1 ranged from 40 min-1 h. The reaction time for Step 2 ranged from 1-1.5 h. This is an alternate procedure for Example 35.

TABLE 5

| Example | Final Product | MS m/z (MH)+ |
|---|---|---|
| 54 | [structure] | 568 |
| 35 | [structure] | 595 |

Example 55

Biochemical Assays

TR-FRET Assay for BIR2 and BIR3

The ability of a test compound to inhibit the binding of BIR2 and/or BIR3 domains of the XIAP protein to Peptide A (a SMAC-derived peptide described below) evidences that the test compound acts as a SMAC-mimetic resulting in reactivation of a cell's apoptotic pathway.

The peptide AVPIAQKSEK-(ε-biotin)-OH 1:2 TFA ("Peptide A") was identified as a substrate for the TR-FRET assay by screening the 6x Histidine-tagged BIR2 domain and BIR3 domain of XIAP against a set of 29 peptides synthesized based on sequences reported by Sweeny et al. (Biochemistry, 2006, 45, 14740 14748). The peptides were labeled with the fluorescent tags FITC or TAMRA and Kd values were determined by fluorescence polarization assay. The sequence AVPIAQKSEK was identified as optimal for using in an assay. The peptide sequence was derivatized with biotin to provide AVPIAQKSEK-(ε-biotin)-OH 1:2 TFA as the substrate for the TR-FRET assay.

The XIAP protein sequence was obtained from the SWISS-PROT protein sequence database and the BIR2 and BIR3 domains were derived from that. The sequence of the BIR2 domain used for the TR-FRET assay is

MRHHHHHHRDHFALDRPSETHADYLLRTGQVVDISDTIYPRNPAMYSEEA

RLKSFQNWPDYAHLTPRELASAGLYYTGIGDQVQCFACGGKLKNWEPGD

FPNCFFVLGRAWSEHRRHRNLNIRSE.

The sequence of the BIR3 domain used for the TR-FRET assay is

MRHHHHHHRSDAVSSDRNFPNSTNLPRNPSMADYEARIFTFGTWIYSVNK

EQLARAGFYALGEGDKVKCFHCGGGLTDWKPSEDPWEQHAKWYPGCK

YLLEQKGQEYINNIHLTHSLEECLVRTT.

Ten nanomolar of 6x Histidine-tagged BIR2 domain, corresponding to amino acids 124-240 of XIAP, or BIR3 domain, corresponding to amino acids 241-356 of XIAP, was mixed with 20 nM of the peptide AVPIAQKSEK-(ε-biotin)-OH 1:2 TFA, in the presence of 50 mM Tris-Cl, pH 7.5, 100 mM NaCl, 1 mM dithiothreitol (DTT) and 0.1 mg/mL bovine serum albumin (BSA). Following a 45 mM incubation at 37° C., Europium-Streptavidin and Allophycocyanin conjugated anti-Histidine antibody were added to a final concentration of 1.5 nM and 15 nM, respectively. Time-resolved fluorescence resonance energy transfer (TR-FRET) signals were measured 1 hour later at room temperature. Test compound potency was assessed at 10 serially diluted concentrations. Percentage of inhibition at each concentration was determined to generate an IC50 value for each test compound.

These values are listed below in Table 6.

TABLE 6

| Ex. # | Name | BIR2 IC50 (μM) | BIR3 IC50 (μM) |
|---|---|---|---|
| 1 | (S)-N-((2S,3S)-1-(4-acetylbenzoyl)-5-((5-bromo-2-methoxynaphthalen-1-yl)methyl)-2-methyl-4-oxo-2,3,4,5-tetrahydro-1H-benzo[b][1,4]diazepin-3-yl)-2-(methylamino)propanamide hydrochloride | 0.003 | 16.04 |
| 2 | (S)-N-((2S,3S)-1-(4-acetylbenzoyl)-5-((6-bromo-2-methoxynaphthalen-1-yl)methyl)-2-methyl-4-oxo-2,3,4,5-tetrahydro-1H-benzo[b][1,4]diazepin-3-yl)-2-(methylamino)propanamide hydrochloride | 0.006 | 13.3 |
| 3 | (S)-N-((2S,3S)-1-(4-acetylbenzoyl)-5((1-(2-cyanophenyl)-1H-indazol-3-yl)methyl)-2-methyl-4-oxo-2,3,4,5-tetrahydro-1H-benzo[b][1,4]diazepin-3-yl)-2-(methylamino)propanamide hydrochloride | 0.012 | >54.8 |
| 4 | (S)-N-((2S,3S)-1-(4-acetylbenzoyl)-5-((3-cyclopropylquinolin-4-yl)methyl)-2-methyl-4-oxo-2,3,4,5-tetrahydro-1H-benzo[b][1,4]diazepin-3-yl)-2-(methylamino)propanamide dihydrochloride | 0.013 | 15.1 |

TABLE 6-continued

| Ex. # | Name | BIR2 IC50 (μM) | BIR3 IC50 (μM) |
|---|---|---|---|
| 5 | (S)-N-((3S,4S)-1-((6-bromo-2-methoxynaphthalen-1-yl)methyl)-5-(4-cyanobenzoyl)-4-methyl-2-oxo-2,3,4,5-tetrahydro-1H-benzo[b][1,4]diazepin-3-yl)-2-(methylamino)propanamide hydrochloride | 0.006 | 14.71 |
| 6 | (S)-N-((3S,4S)-7-cyano-5-(4-cyanobenzoyl)-1-((1-(2-cyanophenyl)-1H-indazol-3-yl)methyl)-4-methyl-2-oxo-2,3,4,5-tetrahydro-1H-benzo[b][1,4]diazepin-3-yl)-2-(methylamino)propanamide hydrochloride | 0.017 | 45.55 |
| 7 | (S)-N-((3S,4S)-1-((6-bromo-2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride | 0.005 | 10.62 |
| 8 | (S)-N-((3S,4S)-1-((5-bromo-2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride | 0.005 | 30.6 |
| 9 | (S)-N-((3S,4S)-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride | 0.009 | 32.39 |
| 10 | (S)-N-((3S,4S)-1-((6-bromo-2-methoxynaphthalen-1-yl)methyl)-4-methyl-5-(2-(methylsulfonyeacetyl)-2-oxo-2,3,4,5-tetrahydro-1H-benzo[b][1,4]diazepin-3-yl)-2-(methylamino)propanamide hydrochloride | 0.010 | 29.18 |
| 11 | (S)-N-((3S,4S)-1-((5-bromo-2-methoxynaphthalen-1-yl)methyl)-4-methyl-5-(2-(methylsulfonyeacetyl)-2-oxo-2,3,4,5-tetrahydro-1H-benzo[b][1,4]diazepin-3-yl)-2-(methylamino)propanamide hydrochloride | 0.009 | 24.91 |
| 12 | (S)-N-((3S,4S)-1-((7-methoxy-2-oxo-2H-chromen-4-yl)methyl)-4-methyl-5-(2-(methylsulfonyeacetyl)-2-oxo-2,3,4,5-tetrahydro-1H-benzo[b][1,4]diazepin-3-yl)-2-(methylamino)propanamide 2,2,2-trifluoroacetate | 0.406 | >54.8 |
| 13 | (S)-N-((3S,4S)-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride | 0.019 | >54.8 |
| 14 | (S)-N-((2S,3S)-2-methyl-5-((3-methylquinolin-4-yl)methyl)-1-(2-(methylsulfonyl)acetyl)-4-oxo-2,3,4,5-tetrahydro-1H-benzo[b][1,4]diazepin-3-yl)-2-(methylamino)propanamide hydrochloride | 0.054 | >54.8 |
| 15 | (S)-N-((3S,4S)-1-((2-chloro-3-methylquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride | 0.043 | 37.47 |
| 16 | (S)-N-((2S,3S)-2-methyl-1-(2-(methylsulfonyl)acetyl)-4-oxo-5-(quinolin-4-ylmethyl)-2,3,4,5-tetrahydro-1H-benzo[b][1,4]diazepin-3-yl)-2-(methylamino)propanamide hydrochloride | 0.179 | >54.8 |
| 17 | (S)-N-((3S,4S)-1-((6-bromo-2-methoxynaphthalen-1-yl)methyl)-5-(3-methoxypropanoyl)-4-methyl-2-oxo-2,3,4,5-tetrahydro-1H-benzo[b][1,4]diazepin-3-yl)-2-(methylamino)propanamide hydrochloride | 0.011 | 50.26 |
| 18 | (S)-N-((2S,3S)-1-acetyl-5-((3-cyclopropylquinolin-4-yl)methyl)-2-methyl-4-oxo-2,3,4,5-tetrahydro-1H-benzo[b][1,4]diazepin-3-yl)-2-(methylamino)propanamide | 0.030 | 18.09 |
| 19 | (S)-N-((2S,3S)-1-acetyl-5-((1-(2-cyanophenyl)-1H-indazol-3-yl)methyl)-2-methyl-4-oxo-2,3,4,5-tetrahydro-1H-benzo[b][1,4]diazepin-3-yl)-2-(methylamino)propanamide | 0.044 | >54.8 |
| 20 | (S)-N-((2S,3S)-1-acetyl-2-methyl-5-((3-methylquinolin-4-yl)methyl)-4-oxo-2,3,4,5-tetrahydro-1H-benzo[b][1,4]diazepin-3-yl)-2-(methylamino)propanamide dihydrochloride | 0.055 | >54.8 |
| 21 | (S)-N-((2S,3S)-1-acetyl-5-((2-methoxynaphthalen-1-yl)methyl)-2-methyl-4-oxo-2,3,4,5-tetrahydro-1H-benzo[b][1,4]diazepin-3-yl)-2-(methylamino)propanamide hydrochloride | 0.018 | 34.02 |
| 22 | (S)-N-((2S,3S)-1-acetyl-2-methyl-5-((2-methylnaphthalen-1-yl)methyl)-4-oxo-2,3,4,5-tetrahydro-1H-benzo[b][1,4]diazepin-3-yl)-2-(methylamino)propanamide hydrochloride | 0.056 | >54.8 |
| 23 | (S)-N-((3S,4S)-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride | 0.016 | 14.54 |
| 24 | (S)-N-((3S,4S)-1-((1-(2-cyanophenyl)-1H-indazol-3-yl)methyl)-4-methyl-2-oxo-5-(tetrahydro-2H-pyran-4-carbonyl)-2,3,4,5-tetrahydro-1H-benzo[b][1,4]diazepin-3 -yl)-2-(methylamino)propanamide hydrochloride | 0.012 | >54.8 |
| 25 | (S)-N-((2S,3S)-5-((5-bromo-2-methoxynaphthalen-1-yl)methyl)-7-cyano-2-methyl-1-(2-(methylsulfonyl)acetyl)-4-oxo-2,3,4,5- | 0.017 | 25.08 |

TABLE 6-continued

| Ex. # | Name | BIR2 IC50 (μM) | BIR3 IC50 (μM) |
|---|---|---|---|
| | tetrahydro-1H-benzo[b][1,4]diazepin-3-yl)-2-(methylamino)propanamide 2,2,2-trifluoroacetate | | |
| 26 | (S)-N-((3S,4S)-1-((5-bromo-2-methoxynaphthalen-1-yl)methyl)-7-cyano-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate | 0.009 | 16.82 |
| 27 | (S)-N-((3S,4S)-7-cyano-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride | 0.010 | 12.88 |
| 28 | (S)-N-((3S,4S)-7-cyano-4-methyl-1-((2-methylnaphthalen-1-yl)methyl)-5-(2-(methylsulfonyeacetyl)-2-oxo-2,3,4,5-tetrahydro-1H-benzo[b][1,4]diazepin-3-yl)-2-(ethylamino)propanamide hydrochloride | 0.075 | >54.8 |
| 29 | (S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)butanamide hydrochloride | 0.023 | 12.15 |
| 30 | (S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)butanamide hydrochloride | 0.034 | 27.19 |
| 31 | (S)-N-((3S,4S)-5-acetyl-7-cyano-1-((2-methoxynaphthalen-1-yl)methyl)-4-methyl-2-oxo-2,3,4,5-tetrahydro-1H-benzo[b][1,4]diazepin-3-yl)-2-(methylamino)propanamide hydrochloride | 0.022 | 23.24 |
| 32 | (S)-N-((3S,4S)-5-acetyl-7-cyano-4-methyl-1-((2-methylnaphthalen-1-yl)methyl)-2-oxo-2,3,4,5-tetrahydro-1H-benzo[b][1,4]diazepin-3-yl)-2-(methylamino)propanamide hydrochloride | 0.046 | 28.935 |
| 33 | (S)-N-((3S,4S)-5-acetyl-7-cyano-1-((3-cyclopropylquinolin-4-yl)methyl)-4-methyl-2-oxo-2,3,4,5-tetrahydro-1H-benzo[b][1,4]diazepin-3-yl)-2-(methylamino)propanamide dihydrochloride | 0.028 | 10.76 |
| 34 | (S)-N-((3S,4S)-7-cyano-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride | 0.010 | 15.45 |
| 35 | (S)-N-((3S,4S)-7-cyano-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide dihydrochloride | 0.015 | 12.37 |
| 36 | (S)-N-((3S,4S)-5-acetyl-1-(5-bromo-2-methoxybenzyl)-7-cyano-4-methyl-2-oxo-2,3,4,5-tetrahydro-1H-benzo[b][1,4]diazepin-3-yl)-2-(methylamino)propanamide hydrochloride | 0.120 | 53.05 |
| 37 | (S)-N-((3S,4S)-5-acetyl-7-cyano-1-((4-methoxybiphenyl-3-yl)methyl)-4-methyl-2-oxo-2,3,4,5-tetrahydro-1H-benzo[b][1,4]diazepin-3-yl)-2-(methylamino)propanamide hydrochloride | 0.189 | 5.524 |
| 38 | (S)-N-((3S,4S)-5-acetyl-7-cyano-1-((2'-fluoro-4-methoxybiphenyl-3-yl)methyl)-4-methyl-2-oxo-2,3,4,5-tetrahydro-1H-benzo[b][1,4]diazepin-3-yl)-2-(methylamino)propanamide hydrochloride | 0.234 | 16.38 |
| 39 | (S)-N-((3S,4S)-1-(benzo[d]isoxazol-3-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate | 0.182 | >54.8 |
| 40 | (S)-N-((3S,4S)-1-((7-chloro-2-oxo-2H-chromen-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate | 0.354 | >54.8 |
| 41 | (S)-N-((3S,4S)-1-((6-bromobenzo[d]isoxazol-3-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate | 0.416 | >54.8 |
| 42 | (S)-N-((3S,4S)-1-((3-cyclopropylquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate | 0.029 | 34.245 |
| 43 | (S)-N-((3S,4S)-1-(5-chloro-2-methoxybenzyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate | 0.125 | >54.8 |
| 44 | (S)-N-((3S,4S)-1-((1-(2-cyanophenyl)-1H-indazol-3-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride | 0.032 | >54.8 |

TABLE 6-continued

| Ex. # | Name | BIR2 IC50 (μM) | BIR3 IC50 (μM) |
|---|---|---|---|
| 45 | (S)-N-((2S,3S)-2-methyl-5-((2-methylnaphthalen-1-yl)methyl)-1-(2-(methylsulfonyl)acetyl)-4-oxo-2,3,4,5-tetrahydro-1H-benzo[b][1,4]diazepin-3-yl)-2-(methylamino)propanamide hydrochloride | 0.058 | >54.8 |
| 46 | (S)-N-((2S,3S)-2-methyl-5((1-methyl-1H-indazol-3-yl)methyl)-1-(2-(methylsulfonyl)acetyl)-4-oxo-2,3,4,5-tetrahydro-1H-benzo[b][1,4]diazepin-3-yl)-2-(methylamino)propanamide hydrochloride | 0.083 | >54.8 |
| 47 | (S)-N-((3S,4S)-1-((2-(difluoromethoxy)naphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride | 0.043 | 40.87 |
| 48 | (S)-N-((3S,4S)-1((3-methoxyquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride | 0.013 | 31.59 |
| 49 | (S)-N-((3S,4S)-1-((5-bromo-2-methoxynaphthalen-1-yl)methyl)-5-(3-methoxypropanoyl)-4-methyl-2-oxo-2,3,4,5-tetrahydro-1H-benzo[b][1,4]diazepin-3-yl)-2-(methylamino)propanamide 2,2,2-trifluoroacetate | 0.010 | 38.05 |
| 50 | (S)-N-((3S,4S)-1-((2-methoxynaphthalen-1-yl)methyl)-5-(3-methoxypropanoyl)-4-methyl-2-oxo-2,3,4,5-tetrahydro-1H-benzo[b][1,4]diazepin-3-yl)-2-(methylamino)propanamide hydrochloride | 0.012 | 26.61 |
| 51 | (S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate | 0.027 | 34.74 |
| 52 | (S)-N-((3S,4S)-7-cyano-1-((3-cyclopropylquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate | 0.023 | 16.95 |
| 53 | (S)-N-((3S,4S)-7-cyano-1-((1-(2-cyanophenyl)-1H-indazol-3-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate | 0.033 | >54.8 |
| 54 | (S)-N-((3S,4S)-7-cyano-4-methyl-1-((2-methylnaphthalen-1-yl)methyl)-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride | 0.023 | 37.08 |

The invention claimed is:
1. A compound of Formula I

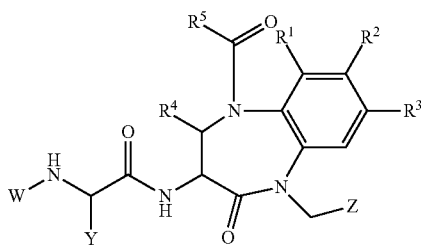

wherein
W is selected from H and $C_{1-6}$-alkyl that optionally may be substituted with 1-3 deuterium atoms;
Y is $C_{1-6}$-alkyl that optionally may be substituted with OR6,
R1, R2 and R3 are the same or different and each is independently selected from H and cyano;
R4 is $C_{1-6}$-alkyl;
R5 is selected from the group
 a) $C_{1-6}$-alkyl that optionally may be substituted with $SO_2R6$ and OR6,
 b) heterocyclyl, and
 c) aryl that optionally may be substituted with C(O)R7, halo and cyano;
Z is selected from the group
 a) aryl that optionally may be substituted with $C_{1-6}$-alkyl, OR6, halogen and aryl that optionally may be substituted with halogen,
 b) heteroaryl that optionally may be substituted with $C_{1-6}$-alkyl, $C_{3-7}$-cycloalkyl, OR6, halogen, oxo and aryl that optionally may substituted with cyano, and
 c) aryl fused with heterocyclyl, wherein the aryl optionally may be substituted with OR6 and halogen, and the heterocyclyl optionally may be substituted with oxo, and
 d) heterocyclyl;
R6 is selected from H and $C_{1-6}$-alkyl that optionally may be substituted with halogen and deuterium; and
R7 is $C_{1-6}$-alkyl;
or a pharmaceutically acceptable salt thereof.

2. The compound of claim 1 wherein W is $C_{1-6}$-alkyl, or a pharmaceutically acceptable salt thereof.

3. The compound of claim 2 wherein W is methyl.

4. The compound according to claim 1 wherein Y is $C_{1-6}$-alkyl, or a pharmaceutically acceptable salt thereof.

5. The compound of claim 4 wherein Y methyl or ethyl, or a pharmaceutically acceptable salt thereof.

6. The compound according to claim 1 wherein R1, R2 and R3 are H, or a pharmaceutically acceptable salt thereof.

7. The compound according to claim 1 wherein R1 is H and either R2 or R3 is cyano and other is H, or a pharmaceutically acceptable salt thereof.

8. The compound according to claim 1 wherein R4 is methyl, or a pharmaceutically acceptable salt thereof.

9. The compound according to claim 1 wherein R5 is $C_{1-6}$-alkyl that optionally may be substituted with $SO_2R6$ or OR6 and R6 is methyl, or a pharmaceutically acceptable salt thereof.

10. The compound according to claim 1 wherein R5 is heterocyclyl, or a pharmaceutically acceptable salt thereof.

11. The compound of claim 10 wherein R5 is tetrahydropyran.

12. The compound according to claim 1 wherein R5 is aryl that optionally may be substituted with C(O)R7, halogen and cyano, or a pharmaceutically acceptable salt thereof.

13. The compound of claim 12 wherein R5 is phenyl that optionally may be substituted with $C(O)CH_3$ and cyano.

14. The compound according to claim 1 wherein Z is aryl, or a pharmaceutically acceptable salt thereof.

15. The compound of claim 14 wherein Z is phenyl that optionally may be substituted with $OCH_3$, halogen and phenyl that optionally may be substituted with halogen.

16. The compound of claim 14 wherein Z is naphthalenyl that optionally may be substituted with $OCH_3$, halogen, $CH_3$ and $OCHF_2$.

17. The compound according to claim 1 wherein Z is heteroaryl, or a pharmaceutically acceptable salt thereof.

18. The compound of claim 17 wherein Z is selected from quinolinyl, indazolyl, chromenyl and bensoisoxazolyl.

19. The compound of claim 1 wherein Z is aryl fused with heterocyclyl, or a pharmaceutically acceptable salt thereof.

20. The compound according to claim 1 wherein R6 is methyl, or a pharmaceutically acceptable salt thereof.

21. The compound according to claim 1 wherein R7 is methyl, or a pharmaceutically acceptable salt thereof.

22. The compound of claim 1 wherein W and Y are each methyl, R1 is H, R2 and R3 are each independently H or cyano, R4 is methyl and R5 is aryl, or a pharmaceutically acceptable salt thereof.

23. The compound of claim 1 wherein W and Y are each methyl, R1 is H, R2 and R3 are each independently H or cyano, R4 is methyl, R5 is $C_{1-6}$-alkyl that optionally may be substituted with $OCH_3$ or $SO_2CH_3$, or a pharmaceutically acceptable salt thereof.

24. The compound of claim 1 wherein W and Y are each methyl, R1 is H, R2 and R3 are each independently H or cyano, R4 is methyl and R5 is heterocyclyl, or a pharmaceutically acceptable salt thereof.

25. The compound of claim 1 wherein W and Y are each methyl, R1 is H, R2 and R3 are each independently H or cyano, R4 is methyl, R5 is $C_{1-6}$-alkyl that optionally may be substituted with $SO_2CH_3$ or $OCH_3$ and Z is aryl, or a pharmaceutically acceptable salt thereof.

26. The compound of claim 1 wherein W and Y are each methyl, R1 is H, R2 and R3 are each independently H or cyano, R4 is methyl, R5 is $C_{1-6}$-alkyl that optionally may be substituted with $SO_2CH_3$ or $OCH_3$ and Z heteroaryl, or a pharmaceutically acceptable salt thereof.

27. The compound of claim 1 wherein W and Y are each methyl, R1 is H, R2 and R3 are each independently H or cyano, R4 is methyl, R5 is heterocyclyl and Z is aryl, or a pharmaceutically acceptable salt thereof.

28. The compound of claim 1 wherein W and Y are each methyl, R1 is H, R2 and R3 are each independently H or cyano, R4 is methyl, R5 is aryl and Z is aryl or heteroaryl, or a pharmaceutically acceptable salt thereof.

29. The compound of claim 1 wherein W and Y are each methyl, R1 is H, R2 and R3 are each independently H or cyano, R4 is methyl, R5 is $C_{1-6}$-alkyl and Z is aryl fused with heterocyclyl, or a pharmaceutically acceptable salt thereof.

30. The compound of claim 1 wherein said compound is:
- (S)-N-((3S,4S)-1-((6-bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride;
- (S)-N-((3S,4S)-1-((5-bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride;
- (S)-N-((3S,4S)-1-((7-methoxy-2-oxo-2H-chromen-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate;
- (S)-N-((3S,4S)-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride;
- (S)-N-((2S,3S)-2-methyl-5-((3-methylquinolin-4-yl)methyl)-1-(2-(methyl sulfonyl)acetyl)-4-oxo-2,3,4,5-tetrahydro-1H-benzo[b][1,4]diazepin-3-yl)-2-(methylamino)propanamide hydrochloride;
- (S)-N-((3S,4S)-1-((2-chloro-3-methylquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride;
- (S)-N-((2S,3S)-2-methyl-1-(2-(methylsulfonyl)acetyl)-4-oxo-5-(quinolin-4-ylmethyl)-2,3,4,5-tetrahydro-1H-benzo[b][1,4]diazepin-3-yl)-2-(methylamino)propanamide hydrochloride;
- (S)-N-((3S,4S)-1-((6-bromo-2-methoxynaphthalen-1-yl)methyl)-5-(3-methoxypropanoyl)-4-methyl-2-oxo-2,3,4,5-tetrahydro-1H-benzo[b][1,4]diazepin-3-yl)-2-(methylamino)propanamide hydrochloride;
- (S)-N-((2S,3S)-1-acetyl-5-((3-cyclopropylquinolin-4-yl)methyl)-2-methyl-4-oxo-2,3,4,5-tetrahydro-1H-benzo[b][1,4]diazepin-3-yl)-2-(methylamino)propanamide;
- (S)-N-((2S,3S)-1-acetyl-5-((1-(2-cyanophenyl)-1H-indazol-3-yl(methyl)-2-methyl-4-oxo-2,3,4,5-tetrahydro-1H-benzo[b][1,4]diazepin-3-yl)-2-(methylamino)propanamide;
- (S)-N-((2S,3S)-1-acetyl-2-methyl-5-((3-methylquinolin-4-yl)methyl)-4-oxo-2,3,4,5-tetrahydro-1H-benzo[b][1,4]diazepin-3-yl)-2-(methylamino)propanamide dihydrochloride;
- (S)-N-((2S,3S)-1-acetyl-5-((2-methoxynaphthalen-1-yl)methyl)-2-methyl-4-oxo-2,3,4,5-tetrahydro-1H-benzo[b][1,4]diazepin-3-yl)-2-(methylamino)propanamide hydrochloride;
- (S)-N-((2S,3S)-1-acetyl-2-methyl-5-((2-methylnaphthalen-1-yl)methyl)-4-oxo-2,3,4,5-tetrahydro-1H-benzo[b][1,4]diazepin-3-yl)-2-(methylamino)propanamide hydrochloride;
- (S)-N-((2S,3S)-5-((5-bromo-2-methoxynaphthalen-1-yl)methyl)-7-cyano-2-methyl-1-(2-(methylsulfonyl)acetyl)-4-oxo-2,3,4,5-tetrahydro-1H-benzo[b][1,4]diazepin-3-yl)-2-(methylamino)propanamide 2,2,2-trifluoroacetate;
- (S)-N-((3S,4S)-1-((5-bromo-2-methoxynaphthalen-1-yl)methyl)-7-cyano-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate;
- (S)-N-((3S,4S)-7-cyano-1-((2-methoxynaphthalen-1-yl)methyl)-4-methyl-5-(2-(methylsulfonyl)acetyl)-2-oxo- 2,3,4,5-tetrahydro-1H-benzo[b][1,4]diazepin-3-yl)-2-(methylamino)propanamide hydrochloride;
(S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)propanamide hydrochloride;
(S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)butanamide hydrochloride;
(S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)butanamide hydrochloride;
(S)-N-((3S,4S)-5-acetyl-7-cyano-1-((2-methoxynaphthalen-1-yl)methyl)-4-methyl-2-oxo-2,3,4,5-tetrahydro-1H-benzo[b][1,4]diazepin-3-yl)-2-(methylamino)propanamide hydrochloride;
(S)-N-((3S,4S)-5-acetyl-7-cyano-4-methyl-1-((2-methylnaphthalen-1-yl)methyl)-2-oxo-2,3,4,5-tetrahydro-1H-benzo[b][1,4]diazepin-3-yl)-2-(methylamino)propanamide hydrochloride;
(S)-N-((3S,4S)-5-acetyl-7-cyano-1-cyclopropylquinolin-4-yl)methyl)-4-methyl-2-oxo-2,3,4,5-tetrahydro-1H-benzo[b][1,4]diazepin-3-yl)-2-(methylamino)propanamide dihydrochloride;
(S)-N-((3S,4S)-5-acetyl-1-(5-bromo-2-methoxybenzyl)-7-cyano-4-methyl-2-oxo-2,3,4,5-tetrahydro-1H-benzo[b][1,4]diazepin-3-yl)-2-(methylamino)propanamide hydrochloride;
(S)-N-((3S,4S)-5-acetyl-7-cyano-1-((4-methoxybiphenyl-3-yl)methyl)-4-methyl-2-oxo-2,3,4,5-tetrahydro-1H-benzo[b][1,4]diazepin-3-yl)-2-(methylamino)propanamide hydrochloride;
(S)-N-((3S,4S)-5-acetyl-7-cyano-1-((2'-fluoro-4-methoxybiphenyl-3-yl)methyl)-4-methyl-2-oxo-2,3,4,5-tetrahydro-1H-benzo[b][1,4]diazepin-3-yl)-2-(methylamino)propanamide hydrochloride;
(S)-N-((3S,4S)-1-(benzo[d]isoxazol-3-ylmethyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate;
(S)-N-((3S,4S)-1-((7-chloro-2-oxo-2H-chromen-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate;
(S)-N-((3S,4S)-1-((6-bromobenzo[d]isoxazol-3-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate;
(S)-N-((3S,4S)-1-((3-cyclopropylquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate;
(S)-N-((3S,4S)-1-(5-chloro-2-methoxybenzyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate;
(S)-N-((3S,4S)-1-((1-(2-cyanophenyl)-1H-indazol-3-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride;
(S)-N-((2S,3S)-2-methyl-5-(2-methylnaphthalen-1-yl)methyl)-1-(2-(methylsulfonyl)acetyl)-4-oxo-2,3,4,5-tetrahydro-1H-benzo[b][1,4]diazepin-3-yl)-2-(methylamino)propanamide hydrochloride;
(S)-N-((2S,3S)-2-methyl-5-((1-methyl-1H-indazol-3-yl)methyl)-1-(2-(methylsulfonyl)acetyl)-4-oxo-2,3,4,5-tetrahydro-1H-benzo[b][1,4]diazepin-3-yl)-2-(methylamino)propanamide hydrochloride;
(S)-N-((3S,4S)-1-((2-(difluoromethoxy)naphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride;
(S)-N-((3S,4S)-1-((3-methoxyquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride;
(S)-N-((3S,4S)-1-((5-bromo-2-methoxynaphthalen-1-yl)methyl)-5-(3-methoxypropanoyl)-4-methyl-2-oxo-2,3,4,5-tetrahydro-1H-benzo[b][1,4]diazepin-3-yl)-2-(methylamino)propanamide 2,2,2-trifluoroacetate;
(S)-N-((3S,4S)-1-((2-methoxynaphthalen-1-yl)methyl)-5-(3-methoxypropanoyl)-4-methyl-2-oxo-2,3,4,5-tetrahydro-1H-benzo[b][1,4]diazepin-3-yl)-2-(methylamino)propanamide hydrochloride;
(S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate;
(S)-N-((3S,4S)-7-cyano-1-((3-cyclopropylquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate; and
(S)-N-((3S,4S)-7-cyano-1-((1-(2-cyanophenyl)-1H-indazol-3-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate;
or a pharmaceutically acceptable salt of any of the foregoing compounds.

31. The compound of claim 1 wherein said compound is:
(S)-N-((2S,3S)-1-(4-acetylbenzoyl)-5-((5-bromo-2-methoxynaphthalen-1-yl)methyl)-2-methyl-4-oxo-2,3,4,5-tetrahydro-1H-benzo[b][1,4]diazepin-3-yl)-2-(methylamino)propanamide hydrochloride;
(S)-N-((2S,3S)-1-(4-acetylbenzoyl)-5-((6-bromo-2-methoxynaphthalen-1-yl)methyl)-2-methyl-4-oxo-2,3,4,5-tetrahydro-1H-benzo[b][1,4]diazepin-3-yl)-2-(methylamino)propanamide hydrochloride;
(S)-N-((2S,3S)-1-(4-acetylbenzoyl)-5-((1-(2-cyanophenyl)-1H-indazol-3-yl)methyl)-2-methyl-4-oxo-2,3,4,5-tetrahydro-1H-benzo[b][1,4]diazepin-3-yl)-2-(methylamino)propanamide hydrochloride;
(S)-N-((2S,3S)-1-(4-acetylbenzoyl)-5-(3-cyclopropylquinolin-4-yl)methyl)-2-methyl-4-oxo-2,3,4,5-tetrahydro-1H-benzo[b][1,4]diazepin-3-yl)-2-(methylamino)propanamide dihydrochloride;
(S)-N-((3S,4S)-1-((6-bromo-2-methoxynaphthalen-1-yl)methyl)-5-(4-cyanobenzoyl)-4-methyl-2-oxo-2,3,4,5-tetrahydro-1H-benzo[b][1,4]diazepin-3-yl)-2-(methylamino)propanamide hydrochloride; and
(S)-N-((3S,4S)-7-cyano-5-(4-cyanobenzoyl)-1-((1-(2-cyanophenyl)-1H-indazol-3-yl)methyl)-4-methyl-2-oxo-2,3,4,5-tetrahydro-1H-benzo[b][1,4]diazepin-3-yl)-2-(methylamino)propanamide hydrochloride;
or a pharmaceutically acceptable salt of any of the foregoing compounds.

32. The compound of claim 1 wherein said compound is:
(S)-N-((3S,4S)-1-((6-bromo-2-methoxynaphthalen-1-yl)methyl)-4-methyl-2-oxo-5-(tetrahydro-2H-pyran-4- carbonyl)-2,3,4,5-tetrahydro-1H-benzo[b][1,4]diazepin-3-yl)-2-(methylamino)propanamide hydrochloride;

(S)-N-((3S,4S)-1-((5-bromo-2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride;

(S)-N-((3S,4S)-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride;

(S)-N-((3S,4S)-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride;

(S)-N-((3S,4S)-1-((1-(2-cyanophenyl)-1H-indazol-3-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride;

(S)-N-((3S,4S)-7-cyano-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride;

(S)-N-((3S,4S)-7-cyano-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide dihydrochloride; and (S)-N-((3S,4S)-7-cyano-4-methyl-1-((2-methylnaphthalen-1-yl)methyl)-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride; or a pharmaceutically acceptable salt thereof.

33. The compound of claim 1, wherein said compound is:
(S)-N-((3S,4S)-1-((6-bromo-2-methoxynaphthalen-1-yl)methyl)-4-methyl-5-(2-methylsulfonyl)acetyl)-2-oxo-2,3,4,5-tetrahydro-1H-benzo[b][1,4]diazepin-3-yl)-2-(methylamino)propanamide hydrochloride;

(S)-N-((3S,4S)-1-((5-bromo-2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride;

(S)-N-((3S,4S)-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride;

(S)-N-((3S,4S)-7-cyano-1-((2-methoxynaphthalen-1-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride;

(S)-N-((3S,4S)-5-acetyl-7-cyano-1-((2-methoxynaphthalen-1-yl)methyl)-4-methyl-2-oxo-2,3,4,5-tetrahydro-1H-benzo[b][1,4]diazepin-3-yl)-2-(methylamino)propanamide hydrochloride;

(S)-N-((3S,4S)-5-acetyl-7-cyano-4-methyl-1-((2-methylnaphthalen-1-yl)methyl)-2-oxo-2,3,4,5-tetrahydro-1H-benzo[b][1,4]diazepin-3-yl)-2-(methylamino)propanamide hydrochloride;

(S)-N-((3S,4S)-5-acetyl-7-cyano-1-((3-cyclopropylquinolin-4-yl)methyl)-4-methyl-2-oxo-2,3,4,5-tetrahydro-1H-benzo[b][1,4]diazepin-3-yl)-2-(methylamino)propanamide dihydrochloride;

(S)-N-((3S,4S)-7-cyano-1-((2-methoxynaphthalen-1-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride;

(S)-N—R3S,4S)-7-cyano-1-((3-cyclopropylquinolin-4-yl)methyl)-4-methyl-2-oxo-5-(tetrahydro-2H-pyran-4-carbonyl)-2,3,4,5-tetrahydro-1H-benzo[b][1,4]diazepin-3-yl)-2-(methylamino)propanamide dihydrochloride;

(S)-N-((3S,4S)-1-(benzo[d]isoxazol-3-ylmethyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate;

(S)-N-((3S,4S)-1-((3-cyclopropylquinolin-4-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide 2,2,2-trifluoroacetate;

(S)-N-((3S,4S)-1-((1-(2-cyanophenyl)-1H-indazol-3-yl)methyl)-4-methyl-5-(2-(methylsulfonyl)acetyl)-2-oxo-2,3,4,5-tetrahydro-1H-benzo[b][1,4]diazepin-3-yl)-2-(methylamino)propanamide hydrochloride;

(S)-N-((2S,3S)-2-methyl-5-((2-methylnaphthalen-1-yl)methyl)-1-(2-(methylsulfonyl)acetyl)-4-oxo-2,3,4,5-tetrahydro-1H-benzo[b][1,4]diazepin-3-yl)-2-(methylamino)propanamide hydrochloride;

(S)-N-((3S,4S)-7-cyano-4-methyl-1-((2-methylnaphthalen-1-yl)methyl)-5-(2-(methylsulfonyl)acetyl)-2-oxo-2,3,4,5-tetrahydro-1H-benzo[1)][1,4]diazepin-3-yl)-2-(methylamino)propanamide 2,2,2-trifluoroacetate; and (S)-N-((3S,4S)-7-cyano-4-methyl-1-((2-methylnaphthalen-1-yl)methyl)-2-oxo-5-(tetrahydro-2H-pyran-4-carbonyl)-2,3,4,5-tetrahydro-1H-benzo[13][1,4]diazepin-3-yl)-2-(methylamino)propanamide hydrochloride; or a pharmaceutically acceptable salt of the foregoing compounds.

34. A pharmaceutical composition comprising a therapeutically effective amount of a compound according to claim 1, or a pharmaceutically acceptable salt thereof, as an active ingredient together with a pharmaceutically acceptable carrier or excipient.

* * * * *